US010919954B2

(12) United States Patent
Brige et al.

(10) Patent No.: US 10,919,954 B2
(45) Date of Patent: *Feb. 16, 2021

(54) ANTIGEN BINDING DIMER-COMPLEXES, METHODS OF MAKING/AVOIDING AND USES THEREOF

(71) Applicant: Ablynx N.V., Ghent-Zwijnaarde (BE)

(72) Inventors: Ann Brige, Ertvelde (BE); Christine Labeur, Bruges (BE); Marc Jozef Lauwereys, Haaltert (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 60 days.

This patent is subject to a terminal disclaimer.

(21) Appl. No.: 15/976,928

(22) Filed: May 11, 2018

(65) Prior Publication Data
US 2018/0362617 A1    Dec. 20, 2018

Related U.S. Application Data

(63) Continuation of application No. 13/254,266, filed as application No. PCT/EP2010/052600 on Mar. 2, 2010, now Pat. No. 10,005,830.

(60) Provisional application No. 61/284,502, filed on Dec. 18, 2009, provisional application No. 61/275,816, filed on Sep. 3, 2009, provisional application No. 61/157,688, filed on Mar. 5, 2009.

(51) Int. Cl.
| | |
|---|---|
| *A61K 39/395* | (2006.01) |
| *C07K 16/00* | (2006.01) |
| *C07K 16/18* | (2006.01) |
| *C07K 16/24* | (2006.01) |
| *C07K 16/28* | (2006.01) |
| *C07K 16/36* | (2006.01) |
| *A61K 9/00* | (2006.01) |
| *A61K 47/02* | (2006.01) |
| *A61K 47/14* | (2017.01) |
| *A61K 47/18* | (2017.01) |
| *A61K 47/26* | (2006.01) |

(52) U.S. Cl.
CPC ............ *C07K 16/00* (2013.01); *A61K 9/0019* (2013.01); *A61K 47/02* (2013.01); *A61K 47/14* (2013.01); *A61K 47/183* (2013.01); *A61K 47/26* (2013.01); *C07K 16/18* (2013.01); *C07K 16/24* (2013.01); *C07K 16/2866* (2013.01); *C07K 16/2875* (2013.01); *C07K 16/36* (2013.01); *C07K 2317/22* (2013.01); *C07K 2317/31* (2013.01); *C07K 2317/569* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| | | |
|---|---|---|
| 6,171,586 B1 | 1/2001 | Lam et al. |
| 7,807,162 B2 | 10/2010 | Silence |
| 8,188,233 B2 | 5/2012 | Condra |
| 8,623,361 B2 | 1/2014 | Beirnaert et al. |
| 8,703,131 B2 | 4/2014 | Beirnaert |
| 9,265,834 B2 | 2/2016 | Brige et al. |
| 9,884,117 B2 | 2/2018 | Brige et al. |
| 10,005,830 B2 | 6/2018 | Brige et al. |
| 2003/0113316 A1 | 6/2003 | Kaisheva et al. |
| 2003/0138417 A1 | 7/2003 | Kaisheva et al. |
| 2003/0181527 A1 | 9/2003 | Andersson et al. |
| 2003/0202972 A1 | 10/2003 | Andya et al. |
| 2006/0088523 A1 | 4/2006 | Andya et al. |
| 2006/0115470 A1 | 6/2006 | Silence et al. |
| 2006/0149041 A1 | 7/2006 | Silence |
| 2007/0086979 A1 | 4/2007 | Chevrier et al. |
| 2007/0172479 A1 | 7/2007 | Warne et al. |
| 2008/0292640 A1 | 11/2008 | Solinger et al. |
| 2009/0226530 A1 | 9/2009 | Lassner et al. |
| 2009/0280129 A1 | 11/2009 | Liu et al. |
| 2010/0137213 A1 | 6/2010 | Fernandez et al. |
| 2011/0311515 A1 | 12/2011 | Bouche et al. |
| 2012/0034212 A1 | 2/2012 | Bowen et al. |

(Continued)

FOREIGN PATENT DOCUMENTS

| | | |
|---|---|---|
| WO | WO 2002/30463 A2 | 4/2002 |
| WO | WO 2004/041863 A2 | 5/2004 |

(Continued)

OTHER PUBLICATIONS

U.S. Appl. No. 15/042,207, filed Feb. 12, 2016, Brige et al.
PCT/EP2010/052600, dated Jun. 30, 2010, International Search Report and Written Opinion.
PCT/EP2010/052600, dated Sep. 15, 2011, International Preliminary Report on Patentability.
PCT/EP2010/062972, dated Oct. 27, 2010, International Search Report and Written Opinion.

(Continued)

*Primary Examiner* — Yunsoo Kim
(74) *Attorney, Agent, or Firm* — Wolf, Greenfield & Sacks, P.C.

(57) ABSTRACT

In a broad aspect the present invention generally relates to novel dimer-complexes (herein called "non-fused-dimers" or NFDs) comprising single variable domains, methods of making these complexes and uses thereof. These non-covalently bound dimer-complexes consist of two identical monomers that each comprises of one or more single variable domains (homodimers) or of two different monomers that each comprises on or more single variable domains (heterodimers). The subject NFDs have typically altered e.g. improved binding characteristics over their monomeric counterpart. The NFDs of the invention may further be engineered through linkage by a flexible peptide or cysteines in order to improve the stability. This invention also describes conditions under which such NFDs are formed and conditions under which the formation of such dimers can be avoided.

9 Claims, 40 Drawing Sheets

Specification includes a Sequence Listing.

(56) References Cited

U.S. PATENT DOCUMENTS

| | | |
|---|---|---|
| 2012/0093839 A1 | 4/2012 | Brige et al. |
| 2012/0201812 A1 | 8/2012 | Brige et al. |
| 2012/0244158 A1 | 9/2012 | Brige et al. |
| 2014/0178383 A1 | 6/2014 | Brige et al. |
| 2016/0279242 A1 | 9/2016 | Brige et al. |

FOREIGN PATENT DOCUMENTS

| | | |
|---|---|---|
| WO | WO 2004/062551 A2 | 7/2004 |
| WO | WO 2005/044858 A1 | 5/2005 |
| WO | WO 2005/072772 A1 | 8/2005 |
| WO | WO 2006/020935 A2 | 2/2006 |
| WO | WO 2006/040153 A2 | 4/2006 |
| WO | WO 2006/074947 A2 | 7/2006 |
| WO | WO 2006/122786 A2 | 11/2006 |
| WO | WO 2006/122825 A2 | 11/2006 |
| WO | WO 2007/002261 A2 | 1/2007 |
| WO | WO 2007/042289 A2 | 4/2007 |
| WO | WO 2007/086797 A1 | 8/2007 |
| WO | WO 2007/092772 A2 | 8/2007 |
| WO | WO 2007/104529 A2 | 9/2007 |
| WO | WO 2008/020079 A1 | 2/2008 |
| WO | WO 2008/039761 A2 | 4/2008 |
| WO | WO 2008/049897 A1 | 5/2008 |
| WO | WO 2008/070721 A2 | 6/2008 |
| WO | WO 2008/071447 A2 | 6/2008 |
| WO | WO 2008/071685 A1 | 6/2008 |
| WO | WO 2008/074839 A2 | 6/2008 |
| WO | WO 2008/074840 A2 | 6/2008 |
| WO | WO 2008/074867 A2 | 6/2008 |
| WO | WO 2008/074868 A1 | 6/2008 |
| WO | WO 2008/077945 A2 | 7/2008 |
| WO | WO 2008/079290 A2 | 7/2008 |
| WO | WO 2008/101985 A2 | 8/2008 |
| WO | WO 2008/142164 A2 | 11/2008 |
| WO | WO 2008/142165 A1 | 11/2008 |
| WO | WO 2009/068625 A2 | 6/2009 |
| WO | WO 2009/068627 A2 | 6/2009 |
| WO | WO 2009/095235 A1 | 8/2009 |
| WO | WO 2009/099641 A2 | 8/2009 |
| WO | WO 2009/109635 A2 | 9/2009 |
| WO | WO 2009/115614 A2 | 9/2009 |
| WO | WO 2010/060768 A1 | 6/2010 |
| WO | WO 2010/077422 A2 | 7/2010 |

OTHER PUBLICATIONS

PCT/EP2010/062972, dated Mar. 15, 2012, International Preliminary Report on Patentability.
PCT/EP2010/062975, dated Nov. 2, 2010, International Search Report and Written Opinion.
PCT/EP2010/062975, dated Mar. 15, 2012, International Preliminary Report on Patentability.
[No Author Listed] Glycine (aminozuur). Wikipedia. Last accessed at http://nl.wikipedia.org/wiki/glycine_(aminozuur) on Oct. 30, 2009.
[No Author Listed] Koolhydraat. Wikipedia. Last accessed at http://nl.wikipedia.org/wiki/koolhydraat on Oct. 30, 2009.
[No Author Listed] Mannitol, a polypol (or sugar alcohol). Polyols Information Source. Last accessed at http://www.polyol.org/fap/fap_mannitol.html on Oct. 30, 2009.
[No Author Listed] Mannitol. Wikipedia. Last accessed at http://nl.wikipedia.org/wiki/mannitol on Oct. 30, 2009.
[No Author Listed] Polyol. Wikipedia. Last accessed at http://nl.wikipedia.org/wiki/polyol on Oct. 30, 2009.
[No Author Listed] Sacharose. Wikipedia. Last accessed at http://nl.wikipedia.org/wiki/sucrose on Oct. 30, 2009.
[No Author Listed] Scientific Discussion. EMEA 2005. 29 pages.
Barthelemy et al., Comprehensive analysis of the factors contributing to the stability and solubility of autonomous human VH domains. J Biol Chem. Feb. 8, 2008;283(6):3639-54. Epub Nov. 28, 2007.
Bork, Powers and pitfalls in sequence analysis: the 70% hurdle. Genome Res. Apr. 2000;10(4):398-400.
Bowie et al., Deciphering the message in protein sequences: tolerance to amino acid substitutions. Science. Mar. 16, 1990;247(4948):1306-10.
Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Chang et al., Practical approaches to protein formulation development. Amgen, Inc. 2002. 1-25.
Cleland et al., The development of stable protein formulations: a close look at protein aggregation, deamidation, and oxidation. Crit Rev Ther Drug Carrier Syst. 1993;10(4):307-77.
Dottorini et al., Crystal structure of a human VH: requirements for maintaining a monomeric fragment. Biochemistry. Jan. 27, 2004;43(3):622-8. Epub Dec. 25, 2003.
Jorgensen et al., Recent trends in stabilising peptides and proteins in pharmaceutical formulation—considerations in the choice of excipients. Expert Opin Drug Deliv. Nov. 2009;6(11):1219-30. doi:10.1517/17425240903199143.
Katayama et al., Effect of buffer species on the thermally induced aggregation of interferon-tau. J Pharm Sci. Jun. 2006;95(6):1212-26.
Labeur, Development of a high concentration Nanobody® formulation. Ablynx. Presentation. Sep. 9, 2009.
Lazar et al., Transforming growth factor alpha: mutation of aspartic acid 47 and leucine 48 results in different biological activities. Mol Cell Biol. Mar. 1998;8(3):1247-52.
Riechmann et al., Single domain antibodies: comparison of camel VH and camelised human VH domains. J Immunol Methods. Dec. 10, 1999;231(1-2):25-38.
Sarciaux et al., Effects of buffer composition and processing conditions on aggregation of bovine IgG during freeze-drying. J. Pharm. Sci. Dec. 1999;88(12):1354-61.
Sepúlveda et al., Binders based on dimerised immunoglobulin VH domains. J Mol Biol. Oct. 17, 2003;333(2):355-65.
Spinelli et al., Domain swapping of a llama VHH domain builds a crystal-wide beta-sheet structure. FEBS Lett. Apr. 23, 2004;564(1-2):35-40. Epub Mar. 29, 2004.
Trevino et al., Amino acid contribution to protein solubility: Asp, Glu, and Ser contribute more favorably than the other hydrophilic amino acids in RNase Sa. J Mol Biol. Feb. 16, 2007;366(2):449-60. Epub Oct. 13, 2006.
Trevino et al., Measuring and increasing protein solubility. J Pharm Sci. Oct. 2008;97(10):4155-66. doi: 10.1002/jps.21327.

FIG. 1

| Position | Human $V_H3$ | Hallmark Residues |
|---|---|---|
| 11 | L, V; predominantly L | L, M, S, V, W; preferably L |
| 37 | V, I, F; usually V | $F^{(1)}$, Y, H, I, L or V, preferably $F^{(1)}$ or Y |
| $44^{(8)}$ | G | $G^{(2)}$, $E^{(3)}$, A, D, Q, R, S, L; preferably $G^{(2)}$, $E^{(3)}$ or Q; most preferably $G^{(2)}$ or $E^{(3)}$. |
| $45^{(8)}$ | L | $L^{(2)}$, $R^{(3)}$, C, I, L, P, Q, V; preferably $L^{(2)}$ or $R^{(3)}$ |
| $47^{(8)}$ | W, Y | $W^{(2)}$, $L^{(1)}$ or $F^{(1)}$, A, G, I, M, R, S, V or Y; preferably $W^{(2)}$, $L^{(1)}$, $F^{(1)}$ or R |
| 83 | R or K; usually R | R, $K^{(5)}$, N, $E^{(5)}$, G, I, M, Q or T; preferably K or R; most preferably K |
| 84 | A, T, D; predominantly A | $P^{(5)}$, A, L, R, S, T, D, V; preferably P |
| 103 | W | $W^{(4)}$, $P^{(6)}$, $R^{(6)}$, S; preferably W |
| 104 | G | G or D; preferably G |
| 108 | L, M or T; predominantly L | Q, $L^{(7)}$ or R; preferably Q or $L^{(7)}$ |

Notes:
(1) In particular, but not exclusively, in combination with KERE or KQRE at positions 43-46.
(2) Usually as GLEW at positions 44-47.
(3) Usually as KERE or KQRE at positions 43-46, e.g. as KEREL, KEREF, KQREL, KQREF or KEREG at positions 43-47. Alternatively, also sequences such as TERE (for example TEREL), KECE (for example KECEL or KECER), RERE (for example REREG), QERE (for example QEREG), KGRE (for example KGREG), KDRE (for example KDREV) are possible. Some other possible, but less preferred sequences include for example DECKL and NVCEL.
(4) With both GLEW at positions 44-47 and KERE or KQRE at positions 43-46.
(5) Often as KP or EP at positions 83-84 of naturally occurring $V_{HH}$ domains.
(6) In particular, but not exclusively, in combination with GLEW at positions 44-47.
(7) With the proviso that when positions 44-47 are GLEW, position 108 is always Q in (non-humanized) $V_{HH}$ sequences that also contain a W at 103.
(8) The GLEW group also contains GLEW-like sequences at positions 44-47, such as for example GVEW, EPEW, GLER, DQEW, DLEW, GIEW, ELEW, GPEW, EWLP, and GPER.

| Building blocks | Monovalent | Bivalent | Trivalent |
|---|---|---|---|
| Non-fused dimers (NFDs) | NFD-Mo | NFD-Di | NFD-Tri |
| Linked-NFDs | Linked NFD-Mo | Linked NFD-Di | Linked NFD-Tri |
| Genetically Fused Polypeptides (corresponding to the NFDs in the same column above) | bivalent | tetravalent | hexavalent |

FIG. 17
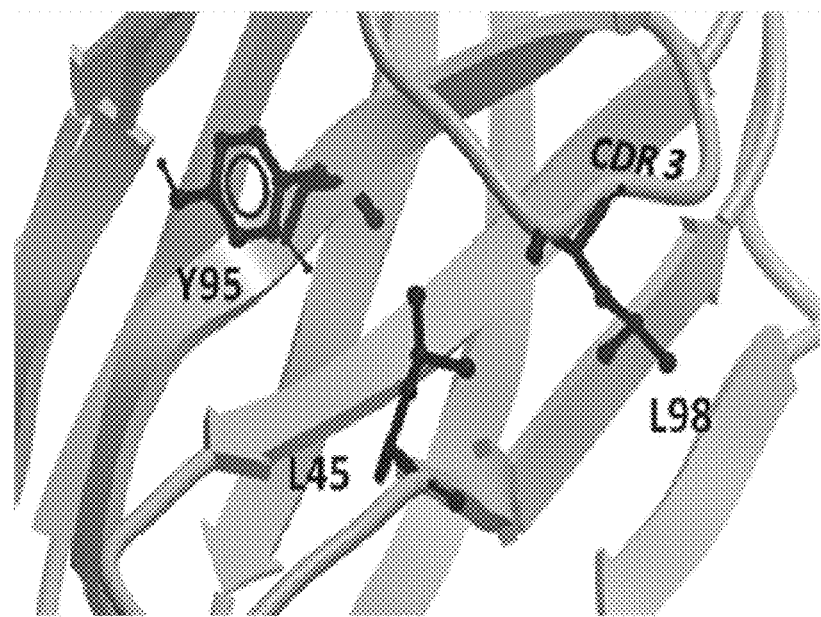
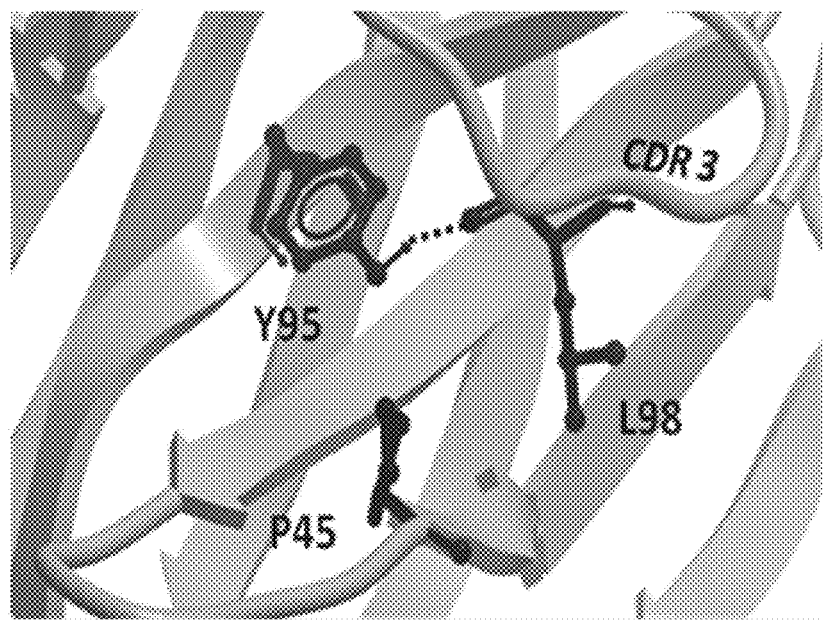

SEQUENCE LISTING

<160> NUMBER OF SEQ ID NOS: 47

<210> SEQ ID NO 1
<211> LENGTH: 259
<212> TYPE: PRT
<213> ORGANISM: Artificial Sequence
<220> FEATURE:
<223> OTHER INFORMATION: Nanobody sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Asp Ser Val Glu Gly Arg Phe Thr Ile Ser Arg Asp Asn Ala Lys Arg
        195                 200                 205

Met Val Tyr Leu Gln Met Asn Ser Leu Arg Ala Glu Asp Thr Ala Val
    210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser

<210> SEQ ID NO 2
<211> LENGTH: 115
<212> TYPE: PRT
<213> ORGANISM: Artificial Sequence
<220> FEATURE:
<223> OTHER INFORMATION: Nanobody sequence

<400> SEQUENCE: 2

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val

```
                35                  40                  45
Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 3
<211> LENGTH: 387
<212> TYPE: PRT
<213> ORGANISM: Artificial Sequence
<220> FEATURE:
<223> OTHER INFORMATION: Nanobody sequence

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser Gly
        115                 120                 125

Gly Gly Gly Ser Gly Gly Ser Glu Val Gln Leu Val Glu Ser Gly
        130                 135                 140

Gly Leu Val Gln Pro Gly Asn Ser Leu Arg Leu Ser Cys Ala Ala
145                 150                 155                 160

Ser Gly Phe Thr Phe Ser Ser Phe Gly Met Ser Trp Val Arg Gln Ala
                165                 170                 175

Pro Gly Lys Gly Leu Glu Trp Val Ser Ser Ile Ser Gly Ser Gly Ser
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Arg Pro
    210                 215                 220

Glu Asp Thr Ala Val Tyr Tyr Cys Thr Ile Gly Gly Ser Leu Ser Arg
225                 230                 235                 240

Ser Ser Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Gly Ser Leu Arg Leu Ser Cys Ala Ala Ser Gly Phe Thr
```

```
                275                 280                 285
Phe Ser Asp Tyr Asp Ile Gly Trp Phe Arg Gln Ala Pro Gly Lys Gly
    290                 295                 300

Arg Glu Gly Val Ser Gly Ile Ser Ser Ser Asp Gly Asn Thr Tyr Tyr
305                 310                 315                 320

Ala Asp Ser Val Lys Gly Arg Phe Thr Ile Ser Arg Asp Asn Ala Lys
                325                 330                 335

Asn Thr Leu Tyr Leu Gln Met Asn Ser Leu Arg Pro Glu Asp Thr Ala
                340                 345                 350

Val Tyr Tyr Cys Ala Ala Glu Pro Pro Asp Ser Ser Trp Tyr Leu Asp
                355                 360                 365

Gly Ser Pro Glu Phe Phe Lys Tyr Trp Gly Gln Gly Thr Leu Val Thr
    370                 375                 380

Val Ser Ser
385

<210> SEQ ID NO 4
<211> LENGTH: 712
<212> TYPE: PRT
<213> ORGANISM: Artificial Sequence
<220> FEATURE:
<223> OTHER INFORMATION: Nanobody sequence

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser Asp
        115                 120                 125

Ala His Lys Ser Glu Val Ala His Arg Phe Lys Asp Leu Gly Glu Glu
    130                 135                 140

Asn Phe Lys Ala Leu Val Leu Ile Ala Phe Ala Gln Tyr Leu Gln Gln
145                 150                 155                 160

Cys Pro Phe Glu Asp His Val Lys Leu Val Asn Glu Val Thr Glu Phe
                165                 170                 175

Ala Lys Thr Cys Val Ala Asp Glu Ser Ala Glu Asn Cys Asp Lys Ser
            180                 185                 190

Leu His Thr Leu Phe Gly Asp Lys Leu Cys Thr Val Ala Thr Leu Arg
        195                 200                 205

Glu Thr Tyr Gly Glu Met Ala Asp Cys Cys Ala Lys Gln Glu Pro Glu
    210                 215                 220

Arg Asn Glu Cys Phe Leu Gln His Lys Asp Asp Asn Pro Asn Leu Pro
225                 230                 235                 240

Arg Leu Val Arg Pro Glu Val Asp Val Met Cys Thr Ala Phe His Asp
```

```
                  245                 250                 255
Asn Glu Glu Thr Phe Leu Lys Lys Tyr Leu Tyr Glu Ile Ala Arg Arg
            260                 265                 270

His Pro Tyr Phe Tyr Ala Pro Glu Leu Leu Phe Phe Ala Lys Arg Tyr
            275                 280                 285

Lys Ala Ala Phe Thr Glu Cys Cys Gln Ala Ala Asp Lys Ala Ala Cys
            290                 295                 300

Leu Leu Pro Lys Leu Asp Glu Leu Arg Asp Glu Gly Lys Ala Ser Ser
305                 310                 315                 320

Ala Lys Gln Arg Leu Lys Cys Ala Ser Leu Gln Lys Phe Gly Glu Arg
                325                 330                 335

Ala Phe Lys Ala Trp Ala Val Ala Arg Leu Ser Gln Arg Phe Pro Lys
                340                 345                 350

Ala Glu Phe Ala Glu Val Ser Lys Leu Val Thr Asp Leu Thr Lys Val
                355                 360                 365

His Thr Glu Cys Cys His Gly Asp Leu Leu Glu Cys Ala Asp Asp Arg
            370                 375                 380

Ala Asp Leu Ala Lys Tyr Ile Cys Glu Asn Gln Asp Ser Ile Ser Ser
385                 390                 395                 400

Lys Leu Lys Glu Cys Cys Glu Lys Pro Leu Leu Glu Lys Ser His Cys
                405                 410                 415

Ile Ala Glu Val Glu Asn Asp Glu Met Pro Ala Asp Leu Pro Ser Leu
                420                 425                 430

Ala Ala Asp Phe Val Glu Ser Lys Asp Val Cys Lys Asn Tyr Ala Glu
                435                 440                 445

Ala Lys Asp Val Phe Leu Gly Met Phe Leu Tyr Glu Tyr Ala Arg Arg
            450                 455                 460

His Pro Asp Tyr Ser Val Val Leu Leu Leu Arg Leu Ala Lys Thr Tyr
465                 470                 475                 480

Glu Thr Thr Leu Glu Lys Cys Cys Ala Ala Ala Asp Pro His Glu Cys
                485                 490                 495

Tyr Ala Lys Val Phe Asp Glu Phe Lys Pro Leu Val Glu Glu Pro Gln
                500                 505                 510

Asn Leu Ile Lys Gln Asn Cys Glu Leu Phe Glu Gln Leu Gly Glu Tyr
            515                 520                 525

Lys Phe Gln Asn Ala Leu Leu Val Arg Tyr Thr Lys Lys Val Pro Gln
            530                 535                 540

Val Ser Thr Pro Thr Leu Val Glu Val Ser Arg Asn Leu Gly Lys Val
545                 550                 555                 560

Gly Ser Lys Cys Cys Lys His Pro Glu Ala Lys Arg Met Pro Cys Ala
                565                 570                 575

Glu Asp Tyr Leu Ser Val Val Leu Asn Gln Leu Cys Val Leu His Glu
            580                 585                 590

Lys Thr Pro Val Ser Asp Arg Val Thr Lys Cys Cys Thr Glu Ser Leu
            595                 600                 605

Val Asn Arg Arg Pro Cys Phe Ser Ala Leu Glu Val Asp Glu Thr Tyr
            610                 615                 620

Val Pro Lys Glu Phe Asn Ala Glu Thr Phe Thr Phe His Ala Asp Ile
625                 630                 635                 640

Cys Thr Leu Ser Glu Lys Glu Arg Gln Ile Lys Lys Gln Thr Ala Leu
                645                 650                 655

Val Glu Leu Val Lys His Lys Pro Lys Ala Thr Lys Glu Gln Leu Lys
                660                 665                 670
```

```
Ala Val Met Asp Asp Phe Ala Ala Phe Val Glu Lys Cys Cys Lys Ala
            675                 680                 685

Asp Asp Lys Glu Thr Cys Phe Ala Glu Glu Gly Lys Lys Leu Val Ala
    690                 695                 700

Ala Ser Gln Ala Ala Leu Gly Leu
705                 710
```

<210> SEQ ID NO 5
<211> LENGTH: 251
<212> TYPE: PRT
<213> ORGANISM: Artificial Sequence
<220> FEATURE:
<223> OTHER INFORMATION: Nanobody sequence

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser Gly
        115                 120                 125

Gly Gly Gly Ser Gly Gly Gly Ser Glu Val Gln Leu Val Glu Ser Gly
    130                 135                 140

Gly Gly Leu Val Gln Pro Gly Asn Ser Leu Arg Leu Ser Cys Ala Ala
145                 150                 155                 160

Ser Gly Phe Thr Phe Ser Ser Phe Gly Met Ser Trp Val Arg Gln Ala
                165                 170                 175

Pro Gly Lys Gly Leu Glu Trp Val Ser Ser Ile Ser Gly Ser Gly Ser
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Arg Pro
    210                 215                 220

Glu Asp Thr Ala Val Tyr Tyr Cys Thr Ile Gly Gly Ser Leu Ser Arg
225                 230                 235                 240

Ser Ser Gln Gly Thr Leu Val Thr Val Ser Ser
                245                 250
```

<210> SEQ ID NO 6
<211> LENGTH: 115
<212> TYPE: PRT
<213> ORGANISM: Artificial Sequence
<220> FEATURE:
<223> OTHER INFORMATION: Nanobody sequence

<400> SEQUENCE: 6

Ala Val Gln Leu Val Glu Ser Gly Gly Gly Leu Val Gln Pro Gly Asn

```
                1               5                   10                  15
            Ser Leu Arg Leu Ser Cys Ala Ala Ser Gly Phe Thr Phe Arg Ser Phe
                            20                  25                  30

Gly Met Ser Trp Val Arg Gln Ala Pro Gly Lys Glu Pro Glu Trp Val
                        35                  40                  45

Ser Ser Ile Ser Gly Ser Gly Ser Asp Thr Leu Tyr Ala Asp Ser Val
                50                  55                  60

Lys Gly Arg Phe Thr Ile Ser Arg Asp Asn Ala Lys Thr Thr Leu Tyr
             65                  70                  75                  80

Leu Gln Met Asn Ser Leu Lys Pro Glu Asp Thr Ala Val Tyr Tyr Cys
                            85                  90                  95

Thr Ile Gly Gly Ser Leu Ser Arg Ser Ser Gln Gly Thr Gln Val Thr
                        100                 105                 110

Val Ser Ser
                    115

<210> SEQ ID NO 7
<211> LENGTH: 214
<212> TYPE: PRT
<213> ORGANISM: Artificial Sequence
<220> FEATURE:
<223> OTHER INFORMATION: A3 domain of vWF

<400> SEQUENCE: 7

Asp Ile Ser Glu Pro Pro Leu His Asp Phe Tyr Cys Ser Arg Leu Leu
             1               5                   10                  15

Asp Leu Val Phe Leu Leu Asp Gly Ser Ser Arg Leu Ser Glu Ala Glu
                            20                  25                  30

Phe Glu Val Leu Lys Ala Phe Val Val Asp Met Met Glu Arg Leu Arg
                        35                  40                  45

Ile Ser Gln Lys Trp Val Arg Val Ala Val Val Glu Tyr His Asp Gly
                50                  55                  60

Ser His Ala Tyr Ile Gly Leu Lys Asp Arg Lys Arg Pro Ser Glu Leu
             65                  70                  75                  80

Arg Arg Ile Ala Ser Gln Val Lys Tyr Ala Gly Ser Gln Val Ala Ser
                            85                  90                  95

Thr Ser Glu Val Leu Lys Tyr Thr Leu Phe Gln Ile Phe Ser Lys Ile
                        100                 105                 110

Asp Arg Pro Glu Ala Ser Arg Ile Ala Leu Leu Leu Met Ala Ser Gln
                        115                 120                 125

Glu Pro Gln Arg Met Ser Arg Asn Phe Val Arg Tyr Val Gln Gly Leu
                        130                 135                 140

Lys Lys Lys Lys Val Ile Val Ile Pro Val Gly Ile Gly Pro His Ala
            145                 150                 155                 160

Asn Leu Lys Gln Ile Arg Leu Ile Glu Lys Gln Ala Pro Glu Asn Lys
                            165                 170                 175

Ala Phe Val Leu Ser Ser Val Asp Glu Leu Glu Gln Gln Arg Asp Glu
                        180                 185                 190

Ile Val Ser Tyr Leu Cys Asp Leu Ala Pro Glu Ala Pro Pro Pro Thr
                        195                 200                 205

His His His His His His
                        210

<210> SEQ ID NO 8
<211> LENGTH: 17
<212> TYPE: PRT
```

<213> ORGANISM: Artificial Sequence
<220> FEATURE:
<223> OTHER INFORMATION: CDR3 and FR4 sequence

<400> SEQUENCE: 8

Gly Gly Ser Leu Ser Arg Ser Ser Gln Gly Thr Leu Val Thr Val Ser
1               5                   10                  15

Ser

<210> SEQ ID NO 9
<211> LENGTH: 115
<212> TYPE: PRT
<213> ORGANISM: Artificial Sequence
<220> FEATURE:
<223> OTHER INFORMATION: Nanobody sequence

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 10
<211> LENGTH: 115
<212> TYPE: PRT
<213> ORGANISM: Artificial Sequence
<220> FEATURE:
<223> OTHER INFORMATION: Nanobody sequence

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 11
<211> LENGTH: 385
<212> TYPE: PRT
<213> ORGANISM: Artificial Sequence
<220> FEATURE:
<223> OTHER INFORMATION: Nanobody sequence

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Gly Trp Phe Arg Gln Ala Pro Gly Lys Gly Arg Glu Phe Val
        35                  40                  45

Ser Ser Ile Thr Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Tyr Ile Arg Pro Asp Thr Tyr Leu Ser Arg Asp Tyr Arg Lys
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Glu Val Gln Leu Val Glu Ser Gly Gly
    130                 135                 140

Gly Leu Val Gln Pro Gly Asn Ser Leu Arg Leu Ser Cys Ala Ala Ser
145                 150                 155                 160

Gly Phe Thr Phe Ser Ser Phe Gly Met Ser Trp Val Arg Gln Ala Pro
                165                 170                 175

Gly Lys Gly Leu Glu Trp Val Ser Ser Ile Ser Gly Ser Gly Ser Asp
            180                 185                 190

Thr Leu Tyr Ala Asp Ser Val Lys Gly Arg Phe Thr Ile Ser Arg Asp
        195                 200                 205

Asn Ala Lys Thr Thr Leu Tyr Leu Gln Met Asn Ser Leu Arg Pro Glu
    210                 215                 220

Asp Thr Ala Val Tyr Tyr Cys Thr Ile Gly Gly Ser Leu Ser Arg Ser
225                 230                 235                 240

Ser Gln Gly Thr Leu Val Thr Val Ser Ser Gly Gly Gly Gly Ser Gly
                245                 250                 255

Gly Gly Ser Glu Val Gln Leu Val Glu Ser Gly Gly Gly Leu Val Gln
            260                 265                 270

Pro Gly Gly Ser Leu Arg Leu Ser Cys Ala Ala Ser Gly Phe Thr Phe
        275                 280                 285

Ser Ser Tyr Pro Met Gly Trp Phe Arg Gln Ala Pro Gly Lys Gly Arg
    290                 295                 300

Glu Phe Val Ser Ser Ile Thr Gly Ser Gly Gly Ser Thr Tyr Tyr Ala
305                 310                 315                 320

Asp Ser Val Lys Gly Arg Phe Thr Ile Ser Arg Asp Asn Ala Lys Asn
                325                 330                 335

Thr Leu Tyr Leu Gln Met Asn Ser Leu Arg Pro Glu Asp Thr Ala Val
            340                 345                 350

Tyr Tyr Cys Ala Ala Tyr Ile Arg Pro Asp Thr Tyr Leu Ser Arg Asp
        355                 360                 365
```

```
Tyr Arg Lys Tyr Asp Tyr Trp Gly Gln Gly Thr Leu Val Thr Val Ser
        370             375                 380

Ser
385

<210> SEQ ID NO 12
<211> LENGTH: 245
<212> TYPE: PRT
<213> ORGANISM: Artificial Sequence
<220> FEATURE:
<223> OTHER INFORMATION: Nanobody sequence

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser Gly Gly Gly Ser Gly Gly
        115                 120                 125

Gly Ser Glu Val Gln Leu Val Glu Ser Gly Gly Gly Leu Val Gln Pro
    130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Arg Ser Ser Gln Gly Thr Leu
225                 230                 235                 240

Val Thr Val Ser Ser
                245

<210> SEQ ID NO 13
<211> LENGTH: 375
<212> TYPE: PRT
<213> ORGANISM: Artificial Sequence
<220> FEATURE:
<223> OTHER INFORMATION: Nanobody sequence

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30
```

Val Met Ala Trp Tyr Arg Gln Ala Pro Gly Lys Gly Arg Glu Leu Val
          35                  40                  45

Ala Gly Ile Ile Ser Gly Gly Ser Thr Ser Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Ile Thr Thr Glu Ser Asp Tyr Asp Leu Gly Arg Arg Tyr Trp Gly
             100                 105                 110

Gln Gly Thr Leu Val Thr Val Ser Ser Gly Gly Gly Ser Gly Gly
         115                 120                 125

Gly Ser Glu Val Gln Leu Val Glu Ser Gly Gly Gly Leu Val Gln Pro
     130                 135                 140

Gly Gly Ser Leu Arg Leu Ser Cys Ala Ala Ser Gly Ser Val Phe Lys
145                 150                 155                 160

Ile Asn Val Met Ala Trp Tyr Arg Gln Ala Pro Gly Lys Gly Arg Glu
                 165                 170                 175

Leu Val Ala Gly Ile Ile Ser Gly Gly Ser Thr Ser Tyr Ala Asp Ser
             180                 185                 190

Val Lys Gly Arg Phe Thr Ile Ser Arg Asp Asn Ala Lys Asn Thr Leu
         195                 200                 205

Tyr Leu Gln Met Asn Ser Leu Arg Pro Glu Asp Thr Ala Val Tyr Tyr
     210                 215                 220

Cys Ala Phe Ile Thr Thr Glu Ser Asp Tyr Asp Leu Gly Arg Arg Tyr
225                 230                 235                 240

Trp Gly Gln Gly Thr Leu Val Thr Val Ser Ser Gly Gly Gly Gly Ser
                 245                 250                 255

Gly Gly Gly Ser Glu Val Gln Leu Val Glu Ser Gly Gly Gly Leu Val
             260                 265                 270

Gln Pro Gly Asn Ser Leu Arg Leu Ser Cys Ala Ala Ser Gly Phe Thr
         275                 280                 285

Phe Ser Ser Phe Gly Met Ser Trp Val Arg Gln Ala Pro Gly Lys Gly
     290                 295                 300

Leu Glu Trp Val Ser Ser Ile Ser Gly Ser Gly Ser Asp Thr Leu Tyr
305                 310                 315                 320

Ala Asp Ser Val Lys Gly Arg Phe Thr Ile Ser Arg Asp Asn Ala Lys
                 325                 330                 335

Thr Thr Leu Tyr Leu Gln Met Asn Ser Leu Arg Pro Glu Asp Thr Ala
             340                 345                 350

Val Tyr Tyr Cys Thr Ile Gly Gly Ser Leu Ser Arg Ser Ser Gln Gly
         355                 360                 365

Thr Leu Val Thr Val Ser Ser
    370                 375

<210> SEQ ID NO 14
<211> LENGTH: 375
<212> TYPE: PRT
<213> ORGANISM: Artificial Sequence
<220> FEATURE:
<223> OTHER INFORMATION: Nanobody sequence

<400> SEQUENCE: 14

Glu Val Gln Leu Val Glu Ser Gly Gly Gly Leu Val Gln Pro Gly Gly
 1               5                   10                  15

```
Ser Leu Arg Leu Ser Cys Ala Ala Ser Gly Ser Val Phe Lys Ile Asn
             20                  25                  30

Val Met Ala Trp Tyr Arg Gln Ala Pro Gly Lys Gly Arg Glu Leu Val
         35                  40                  45

Ala Gly Ile Ile Ser Gly Gly Ser Thr Ser Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser Gly Gly Gly Ser Gly Gly
            115                 120                 125

Gly Ser Glu Val Gln Leu Val Glu Ser Gly Gly Gly Leu Val Gln Pro
130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
                180                 185                 190

Ser Val Lys Gly Arg Phe Thr Ile Ser Arg Asp Asn Ala Lys Thr Thr
                195                 200                 205

Leu Tyr Leu Gln Met Asn Ser Leu Arg Pro Glu Asp Thr Ala Val Tyr
            210                 215                 220

Tyr Cys Thr Ile Gly Gly Ser Leu Ser Arg Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Arg Leu Ser Cys Ala Ala Ser Gly Ser Val Phe Lys Ile Asn Val Met
            275                 280                 285

Ala Trp Tyr Arg Gln Ala Pro Gly Lys Gly Arg Glu Leu Val Ala Gly
        290                 295                 300

Ile Ile Ser Gly Gly Ser Thr Ser Tyr Ala Asp Ser Val Lys Gly Arg
305                 310                 315                 320

Phe Thr Ile Ser Arg Asp Asn Ala Lys Asn Thr Leu Tyr Leu Gln Met
                325                 330                 335

Asn Ser Leu Arg Pro Glu Asp Thr Ala Val Tyr Tyr Cys Ala Phe Ile
            340                 345                 350

Thr Thr Glu Ser Asp Tyr Asp Leu Gly Arg Arg Tyr Trp Gly Gln Gly
            355                 360                 365

Thr Leu Val Thr Val Ser Ser
            370                 375

<210> SEQ ID NO 15
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 15
```

```
Lys Glu Arg Glu
1

<210> SEQ ID NO 16
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 16

Lys Gln Arg Glu
1

<210> SEQ ID NO 17
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 17

Gly Leu Glu Trp
1

<210> SEQ ID NO 18
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 18

Lys Glu Arg Glu Leu
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 19

Lys Glu Arg Glu Phe
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 20

Lys Gln Arg Glu Leu
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 21
```

Lys Gln Arg Glu Phe
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 22

Lys Glu Arg Glu Gly
1               5

<210> SEQ ID NO 23
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 23

Thr Glu Arg Glu
1

<210> SEQ ID NO 24
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 24

Thr Glu Arg Glu Leu
1               5

<210> SEQ ID NO 25
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 25

Lys Glu Cys Glu
1

<210> SEQ ID NO 26
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 26

Lys Glu Cys Glu Leu
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 27

Lys Glu Cys Glu Arg

```
1               5

<210> SEQ ID NO 28
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 28

Arg Glu Arg Glu
1

<210> SEQ ID NO 29
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 29

Arg Glu Arg Glu Gly
1               5

<210> SEQ ID NO 30
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 30

Gln Glu Arg Glu
1

<210> SEQ ID NO 31
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 31

Gln Glu Arg Glu Gly
1               5

<210> SEQ ID NO 32
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 32

Lys Gly Arg Glu
1

<210> SEQ ID NO 33
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 33

Lys Gly Arg Glu Gly
1               5
```

```
<210> SEQ ID NO 34
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 34

Lys Asp Arg Glu
1

<210> SEQ ID NO 35
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 35

Lys Asp Arg Glu Val
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 36

Asp Glu Cys Lys Leu
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 37

Asn Val Cys Glu Leu
1               5

<210> SEQ ID NO 38
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 38

Gly Val Glu Trp
1

<210> SEQ ID NO 39
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 39

Glu Pro Glu Trp
1
```

```
<210> SEQ ID NO 40
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 40

Gly Lys Glu Arg
1

<210> SEQ ID NO 41
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 41

Asp Gln Glu Trp
1

<210> SEQ ID NO 42
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 42

Asp Lys Glu Trp
1

<210> SEQ ID NO 43
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 43

Gly Ile Glu Trp
1

<210> SEQ ID NO 44
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 44

Glu Leu Glu Trp
1

<210> SEQ ID NO 45
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 45

Gly Pro Glu Trp
1
```

```
<210> SEQ ID NO 46
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 46

Glu Trp Leu Pro
1

<210> SEQ ID NO 47
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 47

Gly Pro Glu Arg
1
```

ANTIGEN BINDING DIMER-COMPLEXES, METHODS OF MAKING/AVOIDING AND USES THEREOF

RELATED APPLICATIONS

This application is a continuation of U.S. patent application Ser. No. 13/254,266, filed Dec. 9, 2011, which is a national stage filing under 35 U.S.C. § 371 of international application PCT/EP2010/052600, filed Mar. 2, 2010, which was published under PCT Article 21(2) in English, and claims the benefit under 35 U.S.C. § 119(e) of U.S. provisional application Ser. No. 61/157,688, filed Mar. 5, 2009, U.S. provisional application Ser. No. 61/275,816, filed Sep. 3, 2009, and of U.S. provisional application Ser. No. 61/284,502, filed Dec. 18, 2009, the disclosures of which are incorporated by reference herein in their entireties. incorporated by reference herein in their entireties.

FIELD OF THE INVENTION

In a broad aspect the present invention generally relates to novel dimer-complexes (herein called "non-fused-dimers" or NFDs) comprising single variable domains such as e.g. Nanobodies®, methods of making these complexes and uses thereof. These non-covalently bound dimer-complexes consist of two identical monomers that each comprises one or more single variable domains (homodimers) or of two different monomers that each comprises on or more single variable domains (heterodimers). The subject NFDs have typically altered e.g. improved or decreased binding characteristics over their monomeric counterpart. The NFDs of the invention may further be engineered through linkage by a flexible peptide or cysteines in order to improve the stability.

This invention also describes conditions under which such NFDs are formed and conditions under which the formation of such dimers can be avoided. E.g., the present invention also provides methods for suppressing NFDs such as the dimerization of (human serum) albumin-binding Nanobodies® by adding to a formulation one or more excipients that increase the melting temperature of the singe variable domain such as e.g. by adding mannitol, other polyols or reducing sugars to a liquid formulation.

The present invention also provides formulations of single variable domains wherein the formation of NFDs is suppressed. The formulations of the invention are suitable for administration to human subjects. The invention further relates to containers and pharmaceutical units comprising such formulations and to prophylactic and therapeutic uses of the formulations and pharmaceutical units of the invention.

Other aspects, embodiments, advantages and applications of the invention will become clear from the further description herein.

BACKGROUND OF THE INVENTION

The antigen binding sites of conventional antibodies are formed primarily by the hypervariable loops from both the heavy and the light chain variable domains. Functional antigen binding sites can however also be formed by heavy chain variable domains (VH) alone. In vivo, such binding sites have evolved in camels and camelids as part of heavy chain antibodies, which consist only of two heavy chains and lack light chains. Furthermore, analysis of the differences in amino acid sequence between the VHs of these camel heavy chain-only antibodies (also referred to as VHH) and VH domains from conventional human antibodies helped to design altered human VH domains (Lutz Riechmann and Serge Muyldermans, J. of Immunological Methods, Vol. 231, Issues 1 to 2, 1999, 25-38).

Similarly, it has been shown that by mutation studies of the interface residues as well as of the CDR3 on the VH of the anti-Her2 antibody 4D5 in parallel with the anti-hCG VHH H14, some mutations were found to promote autonomous VH domain behaviour (i.e. beneficial solubility and reversible refolding) (Barthelemy P A et al., 2008, J. of Biol. Chemistry, Vol 283, No 6, pp 3639-3654). It was also found that increasing the hydrophilicity of the former light chain interface by replacing exposed hydrophobic residues by more hydrophilic residues improves the autonomous VH domain behaviour. These engineered VHs were shown to be predominantly monomeric at high concentration, however low quantities of dimers and other aggregates of said engineered VHs were also found that presumably form relative weak interaction similar to those described in the art for VL-VH pair interactions. Similarly, a camelized VH, called cVH-E2, is claimed to form dimers in solution in a concentration dependent manner i.e. at concentrations above 7 mg/ml (but note that data has not been shown in study; Dottorini et al., Biochemistry, 2004, 43, 622-628). Below this concentration, the dimer likely dissociates into monomers and it remains unclear whether these dimers were active (i.e. binding antigen).

Furthermore, it has recently been reported that a truncated llama derived VHH (the first seven amino acids are cleaved off) with a very short CDR3 (only 6 residues) called forms a domain swapped dimer in the crystal structure. Since VHH-R9 has been shown to be functional in solution (low Kd against hapten) and to consist of a monomer only, it is likely that dimerization occurred during the very slow crystallization process (4 to 5 weeks) and that elements such as N-terminal cleavage, high concentration conditions and short CDR3 could lead or contribute to the "condensation" phenomena (see in particular also conclusion part of Spinelli et al., FEBS Letter 564, 2004, 35-40). Sepulveda et al. (J. Mol. Biol. (2003) 333, 355-365) has found that spontaneous formation of VH dimers (VHD) is in many cases permissive, producing molecules with antigen binding specificity. However, based on the reported spontaneous formation (versus the dimers formed by PIA reported herein) and the lack of stability data on the non-fused dimers, it is likely that these are weakly interacting dimers similar to the ones described by Barthelemy (supra).

Taken together, the literature describes the formation of dimers of single variable domains and fragments thereof that a) are interacting primarily on relatively weak hydrophobic interaction (which are e.g. depending on the concentration, reversible), and/or b) occur in another occasion only in the crystallisation process (e.g. as a result of crystal packing forces). Moreover, it has been described that these dimers were not binding antigens anymore (as in Spinelli (supra)) or it is unclear whether these dimers were binding dimers (as in Dottorini (supra) and Barthelemy (supra)).

It has been found (see e.g. WO 09/109635) that stable dimer-complexes can be formed in solution with polypeptides comprising at least one single variable VHH domain. These dimer-complexes are also herein referred to as non-fused-dimers.

SUMMARY OF THE INVENTION

The present invention provides methods and formulations that avoid the formation of dimer-complexes of single variable domains. In one aspect the present invention provides a formulation (also referred to herein as "formulation of the invention"), such as a pharmaceutical formulation, comprising i) a polypeptide that comprises at least one single variable domain, and ii) an excipient, preferably selected from a polyol, a non-reducing sugar and/or a dissaccharide. Preferred excipients for use in the formulation of the invention include sorbitol, mannitol, xylitol, ribitol, trehalose, sucrose and/or erythritol. The excipient is preferably present at a concentration of 1% to 20%, 2.5% to 15%, preferably 5% to 10%, such as 5%, 7.5%, 8% or 10%.

The present inventors have shown that the addition of such an excipient in a formulation can drastically reduce the formation of non-fused dimers of single variable domains. The formulation of the invention is therefore particularly suitable for use with polypeptides comprising at least one single variable domain, wherein said single variable domain is susceptible to dimerization.

As indicated in the background art, it has been found (see e.g. WO 09/109635) that stable dimer-complexes can be formed in solution for polypeptides comprising at least one single variable VHH domain, preferably for polypeptides comprising at least one single variable VHH domain that forms dimers using the methods described herein (i.e. process-induced association, introduction of CDR3/framework region 4 destabilizing residues and/or storage at high temperature and high concentration), more preferably for polypeptides comprising at least one single variable VHH domain with sequences SEQ ID NO: 1 to 6 and 11-14 and/or variants thereof, e.g. single variable VHH domain with sequences that are 70% and more identical to SEQ ID NO: 1 to 6 and 11-14. Some of these stable dimer-complexes (also herein referred to as non-fused-dimers or NFDs; non-fused-dimer or NFD) can retain binding functionality to at least 50% or can even have increased binding affinity compared to their monomeric building blocks, others have decreased or no binding functionality anymore. These NFDs are much more stable compared to the 'transient' concentration-dependent dimers described e.g. in Barthelemy (supra) and are once formed stable in a wide range of concentrations. These NFDs may be formed by swapping framework 4 region between the monomeric building blocks whereby both said monomeric building blocks interlock (see experimental part of the crystal structure of polypeptide B NFD). These dimers are typically formed upon process-induced association (PIA) using methods described herein and/or storage at relative high temperature over weeks (such as e.g. 37° C. over 4 weeks) and high concentration (such as e.g. higher than 50 mg/ml, e.g. 65 mg/ml).

As indicated above, the invention teaches methods and formulations that avoid the formation of such dimer-complexes in i) e.g. an up-scaled production or purification process of said polypeptides comprising single variable domain(s) under non-stress condition (i.e. condition that do not favour unfolding of immunoglobulins), ii) by an adequate formulation with excipients increasing the melting temperature of the single variable domain(s), e.g. by having mannitol in the formulation and/or iii) by increasing the stability of the CDR3 and/or framework 4 region conformation.

Accordingly, in one aspect, the present invention relates to a formulation that comprises a polypeptide comprising one or more single variable domains, said formulation being formulated for administration to a human subject, and further comprising an excipient at a concentration of 1% to 20% (w:v). Preferred excipients for use in the formulation of the present invention are saccharides and/or polyols.

Accordingly, in another aspect, the formulation of the invention comprises a saccharide and/or polyol. Formulations comprising one or more saccharides and/or polyols have shown increased stability (i.e. less tendency to form dimers and/or oligomers and/or or to lose potency) at different stress storage conditions (such as e.g. during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)) and/or an improved melting temperature of the polypeptides present in the formulation. In a specific aspect of the invention, the excipient present in the formulation of the invention is a non-reducing sugar. In another specific aspect, the excipient present in the formulation of the invention is a disaccharide. In another specific aspect, the excipient present in the formulation of the invention is selected from sucrose, trehalose, sorbitol and mannitol. The saccharide and/or polyol is preferably present in the formulation of the invention at a concentration of about 1% to 20%, preferably about 2.5% to 15%, more preferably about 5% to 10%, such as around 5%, around 7.5%, around 8% or around 10%.

The stability of the formulations of the present invention can be demonstrated by the fact that they show only low to undetectable levels of dimer and/or oligomer formation (e.g. as assessed by SE-HPLC) even during storage under one or more stress conditions, such as at a temperature of 37±5° C. and/or 5±5° C. for up to at least 2 weeks (preferably at least 3 weeks, at least 5 weeks, at least 8 weeks, at least 10 weeks, at least 3 months, at least 6 months, at least 1 year, 1.5 year or even 2 years or more). The stability of the formulations of the present invention can also be demonstrated by the fact that they show very little to no loss of the biological activities (e.g. as assessed by ELISA and/or Biacore) even during storage under one or more stress conditions, such as at a temperature of 37±5° C. for up to at least 2 weeks (preferably at least 3 weeks, at least 5 weeks, at least 8 weeks, at least 10 weeks, at least 3 months, at least 6 months, at least 1 year, 1.5 year or even 2 years or more).

More specifically, in the formulations of the present invention at least 80% (preferably at least 90%, more preferably at least 95% or even at least 99%) of the polypeptides retains its binding activity to at least one (preferably to all) of its targets (e.g. as assessed by ELISA and/or Biacore) after storage under one or more of the above stress conditions compared to the binding activity prior to storage. In a specific aspect, at least 80% (preferably at least 90%, more preferably at least 95% or even at least 99%) of the polypeptides retains its binding activity (e.g. as assessed by ELISA and/or Biacore) to at least one (preferably to all) of its targets after storage at 37±5° C. for up to at least 2 weeks (preferably at least 3 weeks, at least 5 weeks, at least 2 months, at least 6 months, at least 1 year, 1.5 year or even 2 years or more) compared to the binding activity prior to storage.

Accordingly the present invention provides stable formulations of polypeptides comprising one or more single variable domains, wherein:
  less than 10% of the polypeptides forms dimers (e.g. as assessed by SE-HPLC) during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more);
  at least 80% of the polypeptides retain its binding activity (e.g. as assessed by ELISA and/or Biacore) to at least one (preferably to all) of its targets after storage at 37±5° C. up to 2 weeks (preferably at least 3 weeks, at least 5 weeks, at least 2 months, at least 6 months, at least 1 year, 1.5 year or even 2 years or more) compared to the binding activity prior to storage; and/or The present invention further provides methods for preparing the stable formulations of the invention. The methods of the invention may comprise the steps of concentrating a polypeptide comprising one or more single variable domains and exchanging it with the preferred buffer and/or excipient.

Also provided are containers, kits and pharmaceutical unit dosages comprising the formulations of the invention for use by, e.g., a healthcare professional. In specific embodiments, the kits or pharmaceutical unit dosages comprising the stable formulations of the invention are formulated for parenteral administration (e.g., intradermally, intramuscularly, intraperitoneally, intravenously and/or subcutaneously) of the polypeptide of the invention to a human subject. The formulations, containers, pharmaceutical unit dosages and/or kits can be used in prophylaxis and/or therapy. In a specific aspect, the formulations, containers, pharmaceutical unit dosages and/or kits are used for the prevention and/or treatment of one or more diseases and/or disorders such as vascular diseases and/or disorders (such as e.g. acute coronary syndrome (ACS), myocardial infarction, thrombotic thrombocytopenic purpura (TIP) or Moschcowitz syndrome, vascular surgery, stroke), bone diseases and/or disorders (such as e.g. osteoporosis, cancer-related bone diseases, and/or bone loss associated with autoimmunity and/or viral infection) or autoimmune diseases (such as e.g. rheumatoid arthritis).

BRIEF DESCRIPTION OF THE FIGURES

FIG. 1: Hallmark Residues in single variable domains. SEQ IDs are as follows: KERE, SEQ ID NO: 15; KQRE, SEQ ID NO: 16; GLEW, SEQ ID NO: 17; KEREL, SEQ ID NO: 18; KEREF, SEQ ID NO: 19; KQREL, SEQ ID NO: 20; KQREF, SEQ ID NO: 21; KEREG, SEQ ID NO: 22; TERE, SEQ ID NO: 23; TEREL, SEQ ID NO: 24; KECE, SEQ ID NO: 25; KECEL, SEQ ID NO: 26; KECER, SEQ ID NO: 27; RERE, SEQ ID NO: 28; REREG, SEQ ID NO: 29; QERE, SEQ ID NO: 30; QEREG, SEQ ID NO: 31; KGRE, SEQ ID NO: 32; KGREG, SEQ ID NO: 33; KDRE, SEQ ID NO: 34; KDREV, SEQ ID NO: 35; DECKL, SEQ ID NO: 36; NVCEL, SEQ ID NO: 37; GVEW, SEQ ID NO: 38; EPEW, SEQ ID NO: 39; GLER, SEQ ID NO: 40; DQEW, SEQ ID NO: 41; DLEW, SEQ ID NO: 42; GIEW, SEQ ID NO: 43; ELEW, SEQ ID NO: 44; GPEW, SEQ ID NO: 45; EWLP, SEQ ID NO: 46; and GPER, SEQ ID NO: 47.

FIG. 17: Polypeptide B (top) and polypeptide F with Pro at position 45 (bottom).

DETAILED DESCRIPTION OF THE INVENTION

Definitions

Figure 2A:
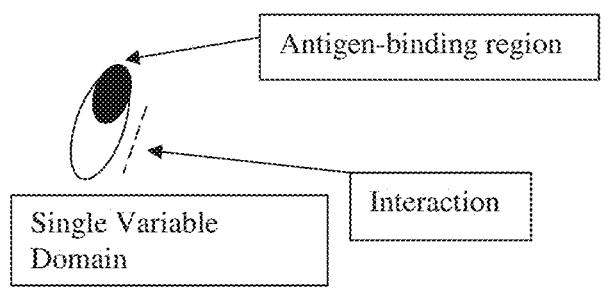
FIGS. 2A-2B: Illustration of various non-fused dimers (i.e. NFDs) and comparison with the conventional genetically fused molecules. Single Variable Domains in each construct or NFD may be different (FIG. 2B) or identical (FIG. 2A). The dashed line is a schematic interaction between the 2 VH domains that confer the NFD its stability (indicated here are surface interactions but these can also be other interaction as described in the invention herein).

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10$^{th}$ Ed. Blackwell Publishing, UK (2001); and Janeway et al., "Immunobiology" (6th Ed.), Garland Science Publishing/Churchill Livingstone, N.Y. (2005), as well as to the general background art cited herein;

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

Amino acid residues will be indicated according to the standard three-letter or one-letter amino acid code, as mentioned in Table A-2.

TABLE A-2

| one-letter and three-letter amino acid code | | | |
|---|---|---|---|
| Nonpolar, uncharged (at pH 6.0-7.0)[3] | Alanine | Ala | A |
| | Valine | Val | V |
| | Leucine | Leu | L |
| | Isoleucine | Ile | I |
| | Phenylalanine | Phe | F |

TABLE A-2-continued one-letter and three-letter amino acid code

|  | Methionine[1] | Met | M |
|---|---|---|---|
|  | Tryptophan | Trp | W |
|  | Proline | Pro | P |
| Polar, uncharged | Glycine[2] | Gly | G |
| (at pH 6.0-7.0) | Serine | Ser | S |
|  | Threonine | Thr | T |
|  | Cysteine | Cys | C |
|  | Asparagine | Asn | N |
|  | Glutamine | Gln | Q |
|  | Tyrosine | Tyr | Y |
| Polar, charged | Lysine | Lys | K |
| (at pH 6.0-7.0) | Arginine | Arg | R |
|  | Histidine[4] | His | H |
|  | Aspartate | Asp | D |
|  | Glutamate | Glu | E |

Notes:
[1]Sometimes also considered to be a polar uncharged amino acid.
[2]Sometimes also considered to be a nonpolar uncharged amino acid.
[3]As will be clear to the skilled person, the fact that an amino acid residue is referred to in this Table as being either charged or uncharged at pH 6.0 to 7.0 does not reflect in any way on the charge said amino acid residue may have at a pH lower than 6.0 and/or at a pH higher than 7.0; the amino acid residues mentioned in the Table can be either charged and/or uncharged at such a higher or lower pH, as will be clear to the skilled person.
[4]As is known in the art, the charge of a His residue is greatly dependant upon even small shifts in pH, but a His residue can generally be considered essentially uncharged at a pH of about 6.5.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position).

Alternatively, the degree of sequence identity between two or more nucleotide sequences may be calculated using a known computer algorithm for sequence alignment such as NCBI Blast v2.0, using standard settings.

Some other techniques, computer algorithms and settings for determining the degree of sequence identity are for example described in WO 04/037999, EP 0 967 284, EP 1 085 089, WO 00/55318, WO 00/78972, WO 98/49185 and GB 2 357 768-A.

Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein.

Alternatively, the degree of sequence identity between two amino acid sequences may be calculated using a known computer algorithm, such as those mentioned above for determining the degree of sequence identity for nucleotide sequences, again using standard settings.

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB-A-3 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gin; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu: Cys into Ser; Gin into Asn; Glu into Asp; Gly into Ala or into Pro; His into Asn or into Gln; Ile into Leu or into Val; Leu into Ile or into Val; Lys into Arg, into Gin or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81: 140-144, 1984; Kyte & Doolittle; J Molec. Biol. 157: 105-132, 198 1, and Goldman et al., Ann. Rev. Biophys. Chem. 15: 321-353, 1986, all incorporated herein in their entirety by reference. Information on the primary, secondary and tertiary structure of Nanobodies® is given in the description herein and in the general background art cited above. Also, for this purpose, the crystal structure of a $V_{HH}$ domain from a llama is for example given by Desmyter et al., Nature Structural Biology, Vol. 3, 9. 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

Amino acid sequences and nucleic acid sequences are said to be "exactly the same" if they have 100% sequence identity (as defined herein) over their entire length.

When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a Nanobody® of the invention is said to comprise a CDR sequence, this may mean that said CDR sequence has been incorporated into the Nanobody® of the invention, but more usually this generally means that the Nanobody® of the invention contains within its sequence a stretch of amino acid residues with the same amino acid sequence as said CDR sequence, irrespective of how said Nanobody® of the invention has been generated or obtained. It should also be noted that when the latter amino acid sequence has a specific biological or structural function, it preferably has essentially the same, a similar or an equivalent biological or structural function in the first mentioned amino acid sequence (in other words, the first mentioned amino acid sequence is preferably such that the latter sequence is capable of performing essentially the same, a similar or an equivalent biological or structural function). For example, when a Nanobody® of the invention is said to comprise a CDR sequence or framework sequence, respectively, the CDR sequence and framework are preferably capable, in said Nanobody®, of functioning as a CDR sequence or framework sequence, respectively. Also, when a nucleotide sequence is said to comprise another nucleotide sequence, the first mentioned nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleotide sequence).

A nucleic acid sequence or amino acid sequence is considered to be "(in) essentially isolated (form)"—for example, compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatographical technique, such as polyacrylamide-gel electrophoresis.

The term "domain" as used herein generally refers to a globular region of an amino acid sequence (such as an antibody chain, and in particular to a globular region of a heavy chain antibody), or to a polypeptide that essentially consists of such a globular region. Usually, such a domain will comprise peptide loops (for example 3 or 4 peptide loops) stabilized, for example, as a sheet or by disulfide bonds. The term "binding domain" refers to such a domain that is directed against an antigenic determinant (as defined herein).

The term "antigenic determinant" refers to the epitope on the antigen recognized by the antigen-binding molecule (such as a Nanobody® or a polypeptide of the invention) and more in particular by the antigen-binding site of said molecule. The terms "antigenic determinant" and "epitope" may also be used interchangeably herein.

As further described in paragraph m) on page 53 of WO 08/020079, an amino acid sequence (such as a Nanobody, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

The term "specificity" refers to the number of different types of antigens or antigenic determinants to which a particular antigen-binding molecule or antigen-binding protein (such as a Nanobody® or a polypeptide of the invention) molecule can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as a Nanobody® or polypeptide of the invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as the amino acid sequences, Nanobodies® and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ M$^{-1}$) liters/mol is generally considered to indicate non-specific binding. Preferably, a monovalent immunoglobulin sequence of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more then $10^{-4}$ moles/liter or $10^{-3}$ moles/liter (e.g. of $10^{-2}$ moles/liter). Optionally, as will also be clear to the skilled person, the (actual or apparent) dissociation constant may be calculated on the basis of the (actual or apparent) association constant ($K_A$), by means of the relationship [$K_D=1/K_A$].

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of (mol/liter)$^{-1}$ (or M$^{-1}$). In the present specification, the stability of the interaction between two molecules (such as an amino acid sequence, Nanobody® or polypeptide of the invention and its intended target) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well known relation DG=RT·ln($K_D$) (equivalently DG=RT·ln($K_A$)), where R equals the gas constant, T equals the absolute temperature and ln denotes the natural logarithm. The $K_D$ for biological interactions which are considered meaningful (e.g. specific) are typically in the range of $10^{-10}$M (0.1 nM) to $10^{-5}$M (10000 nM). The stronger an interaction is, the lower is its $K_D$. The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units s$^{-1}$ (where s is the SI unit notation of second). The on-rate $k_{on}$ has units M$^{-1}$s$^{-1}$. The on-rate may vary between $10^2$ M$^{-1}$s$^{-1}$ to about $10^7$ M$^{-1}$s$^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^{-6}$ s$^{-1}$ (near irreversible complex with a $t_{1/2}$ of multiple days) to 1 s$^{-1}$ ($t_{1/2}=0.69$ s).

The affinity of a molecular interaction between two molecules can be measured via different techniques known per se, such as the well known surface plasmon resonance (SPR) biosensor technique (see for example Ober et al., Intern. Immunology, 13, 1551-1559, 2001) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE instruments.

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol. Methods, 77, 305-19, 1985). This method establishes a solution phase binding equilibrium measurement and avoids possible artefacts relating to adsorption of one of the molecules on a support such as plastic.

However, the accurate measurement of $K_D$ may be quite labor-intensive and as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D=IC_{50}/(1+c_{ref}/K_{D\ ref})$. Note that if $c_{ref}\ll K_{D\ ref}$, $K_D\approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

The half-life of an amino acid sequence, compound or polypeptide of the invention can generally be defined as the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally involve the steps of suitably administering to a warm-blooded animal (i.e. to a human or to another suitable mammal, such as a mouse, rabbit, rat, pig, dog or a primate, for example monkeys from the genus *Macaca* (such as, and in particular, cynomolgus monkeys (*Macaca fascicularis*) and/or rhesus monkeys (*Macaca mulatta*)) and baboon (*Papio ursinus*)) a suitable dose of the amino acid sequence, compound or polypeptide of the invention; collecting blood samples or other samples from said animal; determining the level or concentration of the amino acid sequence, compound or polypeptide of the invention in said blood sample; and calculating, from (a plot of) the data thus obtained, the time until the level or concentration of the amino acid sequence, compound or polypeptide of the invention has been reduced by 50% compared to the initial level upon dosing. Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982).

As will also be clear to the skilled person (see for example pages 6 and 7 of WO 04/003019 and in the further references cited therein), the half-life can be expressed using parameters such as the t1/2-alpha, t1/2-beta and the area under the curve (AUC). In the present specification, an "increase in half-life" refers to an increase in any one of these parameters, such as any two of these parameters, or essentially all three these parameters. As used herein "increase in half-life" or "increased half-life" in particular refers to an increase in the t1/2-beta, either with or without an increase in the t1/2-alpha and/or the AUC or both.

In the context of the present invention, "modulating" or "to modulate" generally means either reducing or inhibiting the activity of, or alternatively increasing the activity of, a target or antigen, as measured using a suitable in vitro, cellular or in vivo assay. In particular, "modulating" or "to modulate" may mean either reducing or inhibiting the activity of, or alternatively increasing a (relevant or intended) biological activity of, a target or antigen, as measured using a suitable in vitro, cellular or in vivo assay (which will usually depend on the target or antigen involved), by at least 1%, preferably at least 5%, such as at least 10% or at least 25%, for example by at least 50%, at least 60%, at least 70%, at least 80%, or 90% or more, compared to activity of the target or antigen in the same assay under the same conditions but without the presence of the construct of the invention.

As will be clear to the skilled person, "modulating" may also involve effecting a change (which may either be an increase or a decrease) in affinity, avidity, specificity and/or selectivity of a target or antigen for one or more of its ligands, binding partners, partners for association into a homomultimeric or heteromultimeric form, or substrates; and/or effecting a change (which may either be an increase or a decrease) in the sensitivity of the target or antigen for one or more conditions the medium or surroundings in which the target or antigen is present (such as pH, ion strength, the presence of co-factors, etc.), compared to the same conditions but without the presence of the construct of the invention. As will be clear to the skilled person, this may again be determined in any suitable manner and/or using any suitable assay known per se, depending on the target or antigen involved.

"Modulating" may also mean effecting a change (i.e. an activity as an agonist, as an antagonist or as a reverse agonist, respectively, depending on the target or antigen and the desired biological or physiological effect) with respect to one or more biological or physiological mechanisms, effects, responses, functions, pathways or activities in which the target or antigen (or in which its substrate(s), ligand(s) or pathway(s) are involved, such as its signalling pathway or metabolic pathway and their associated biological or physiological effects) is involved. Again, as will be clear to the skilled person, such an action as an agonist or an antagonist may be determined in any suitable manner and/or using any suitable (in vitro and usually cellular or in assay) assay known per se, depending on the target or antigen involved. In particular, an action as an agonist or antagonist may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the construct of the invention.

Modulating may for example also involve allosteric modulation of the target or antigen; and/or reducing or inhibiting the binding of the target or antigen to one of its substrates or ligands and/or competing with a natural ligand, substrate for binding to the target or antigen. Modulating may also involve activating the target or antigen or the mechanism or pathway in which it is involved. Modulating may for example also involve effecting a change in respect of the folding or confirmation of the target or antigen, or in respect of the ability of the target or antigen to fold, to change its confirmation (for example, upon binding of a ligand), to associate with other (sub)units, or to disassociate. Modulating may for example also involve effecting a change in the ability of the target or antigen to transport other compounds or to serve as a channel for other compounds (such as ions).

Modulating may be reversible or irreversible, but for pharmaceutical and pharmacological purposes will usually be in a reversible manner.

In respect of a target or antigen, the term "interaction she" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerization (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, signalling, biological mechanism or biological effect in which the target or antigen is involved) is modulated (as defined herein).

An amino acid sequence or polypeptide is said to be "specific for" a first target or antigen compared to a second target or antigen when is binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10,000 times or more better than the affinity with which said amino acid sequence or polypeptide binds to the second target or polypeptide. For example, the first antigen may bind to the target or antigen with a $K_D$ value that is at least 10 times less, such as at least 100 times less, and preferably at least 1000 times less, such as 10,000 times less or even less than that, than the $K_D$ with which said amino acid sequence or polypeptide binds to the second target or polypeptide. Preferably, when an amino acid sequence or polypeptide is "specific for" a first target or antigen compared to a second target or antigen, it is directed against (as defined herein) said first target or antigen, but not directed against said second target or antigen.

The terms "cross-block", "cross-blocked" and "cross-blocking" are used interchangeably herein to mean the ability of an amino acid sequence or other binding agents (such as a polypeptide of the invention) to interfere with the binding of other amino acid sequences or binding agents of the invention to a given target. The extend to which an amino acid sequence or other binding agents of the invention is able to interfere with the binding of another to a target, and therefore whether it can be said to cross-block according to the invention, can be determined using competition binding assays. One particularly suitable quantitative assay uses a Biacore machine which can measure the extent of interactions using surface plasmon resonance technology. Another suitable quantitative cross-blocking assay uses an ELISA-based approach to measure competition between amino acid sequence or another binding agents in terms of their binding to the target.

The following generally describes a suitable Biacore assay for determining whether an amino acid sequence or other binding agent cross-blocks or is capable of cross-blocking according to the invention. It will be appreciated that the assay can be used with any of the amino acid sequence or other binding agents described herein. The Biacore machine (for example the Biacore 3000) is operated in line with the manufacturer's recommendations. Thus in one cross-blocking assay, the target protein is coupled to a CM5 Biacore chip using standard amine coupling chemistry to generate a surface that is coated with the target. Typically 200-800 resonance units of the target would be coupled to the chip (an amount that gives easily measurable levels of binding but that is readily saturable by the concentrations of test reagent being used). Two test amino acid sequences (termed A* and B*) to be assessed for their ability to cross-block each other are mixed at a one to one molar ratio of binding sites in a suitable buffer to create the test mixture. When calculating the concentrations on a binding site basis the molecular weight of an amino acid sequence is assumed to be the total molecular weight of the amino acid sequence divided by the number of target binding sites on that amino acid sequence. The concentration of each amino acid sequence in the test mix should be high enough to readily saturate the binding sites for that amino acid sequence on the target molecules captured on the Biacore chip. The amino acid sequences in the mixture are at the same molar concentration (on a binding basis) and that concentration would typically be between 1.00 and 1.5 micromolar (on a binding site basis). Separate solutions containing A* alone and B* alone are also prepared A* and B* in these solutions should be the same buffer and at the same concentration as in the test mix. The test mixture is passed over the target-coated Biacore chip and the total amount of binding recorded. The chip is then treated in such a way as to remove the bound amino acid sequences without damaging the chip-bound target. Typically this is done by treating the chip with 30 mM HCl for 60 seconds. The solution of A* alone is then passed over the target-coated surface and the amount of binding recorded. The chip is again treated to remove all of the bound amino acid sequences without damaging the chip-bound target. The solution of B* alone is then passed over the target-coated surface and the amount of binding recorded. The maximum theoretical binding of the mixture of A* and B* is next calculated, and is the sum of the binding of each amino acid sequence when passed over the target surface alone. If the actual recorded binding of the mixture is less than this theoretical maximum then the two amino acid sequences are cross-blocking each other. Thus, in general, a cross-blocking amino acid sequence or other binding agent according to the invention is one which will bind to the target in the above Biacore cross-blocking assay such that during the assay and in the presence of a second amino acid sequence or other binding agent of the invention the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two amino acid sequences or binding agents in combination. The Biacore assay described above is a primary assay used to determine if amino acid sequences or other binding agents cross-block each other according to the invention. On rare occasions particular amino acid sequences or other binding agents may not bind to target coupled via amine chemistry to a CM5 Biacore chip (this usually occurs when the relevant binding site on target is masked or destroyed by the coupling to the chip). In such cases cross-blocking can be determined using a tagged version of the target, for example a N-terminal His-tagged version. In this particular format, an anti-His amino acid sequence would be coupled to the Biacore chip and then the His-tagged target would be passed over the surface of the chip and captured by the anti-His amino acid sequence. The cross blocking analysis would be carried out essentially as described above, except that after each chip regeneration cycle, new His-tagged target would be loaded back onto the anti-His amino acid sequence coated surface. In addition to the example given using N-terminal His-tagged target, C-terminal His-tagged target could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

The following generally describes an ELISA assay for determining whether an amino acid sequence or other binding agent directed against a target cross-blocks or is capable of cross-blocking as defined herein. It will be appreciated that the assay can be used with any of the amino acid sequences (or other binding agents such as polypeptides of the invention) described herein. The general principal of the assay is to have an amino acid sequence or binding agent that is directed against the target coated onto the wells of an ELISA plate. An excess amount of a second, potentially cross-blocking, anti-target amino acid sequence is added in solution (i.e. not bound to the ELISA plate). A limited amount of the target is then added to the wells. The coated amino acid sequence and the amino acid sequence in solution compete for binding of the limited number of target molecules. The plate is washed to remove excess target that has not been bound by the coated amino acid sequence and to also remove the second, solution phase amino acid sequence as well as any complexes formed between the second, solution phase amino acid sequence and target. The amount of bound target is then measured using a reagent that is appropriate to detect the target. An amino acid sequence in solution that is able to cross-block the coated amino acid sequence will be able to cause a decrease in the number of target molecules that the coated amino acid sequence can bind relative to the number of target molecules that the coated amino acid sequence can bind in the absence of the second, solution phase, amino acid sequence. In the instance where the first amino acid sequence, e.g. an Ab-X, is chosen to be the immobilized amino acid sequence, it is coated onto the wells of the ELISA plate, after which the plates are blocked with a suitable blocking solution to minimize non-specific binding of reagents that are subsequently added. An excess amount of the second amino acid sequence, i.e. Ab-Y, is then added to the ELISA plate such that the moles of Ab-Y target binding sites per well are at least 10 fold higher than the moles of Ab-X target binding sites that were used, per well, during the coating of the ELISA plate. Target is then added such that the moles of target added per well are at least 25-fold lower than the moles of Ab-X target binding sites that were used for coating each well. Following a suitable incubation period the ELISA plate is washed and a reagent for detecting the target is added to measure the amount of target specifically bound by the coated anti-target amino acid sequence (in this case Ab-X). The background signal for the assay is defined as the signal obtained in wells with the coated amino acid sequence (in this case Ab-X), second solution phase amino acid sequence (in this case Ab-Y), target buffer only (i.e. without target) and target detection reagents. The positive control signal for the assay is defined as the signal obtained in wells with the coated amino acid sequence (in this case Ab-X), second solution phase amino acid sequence buffer only (i.e. without second solution phase amino acid sequence), target and target detection reagents. The ELISA assay may be run in such a manner so as to have the positive control signal be at least 6 times the background signal. To avoid any artefacts (e.g. significantly different affinities between Ab-X and Ab-Y for the target) resulting from the choice of which amino acid sequence to use as the coating amino acid sequence and which to use as the second (competitor) amino acid sequence, the cross-blocking assay may be run in two formats: 1) format 1 is where Ab-X is the amino acid sequence that is coated onto the ELISA plate and Ab-Y is the competitor amino acid sequence that is in solution and 2) format 2 is where Ab-Y is the amino acid sequence that is coated onto the ELISA plate and Ab-X is the competitor amino acid sequence that is in solution. Ab-X and Ab-Y are defined as cross-blocking if, either in format 1 or in format 2, the solution phase anti-target amino acid sequence is able to cause a reduction of between 60% and 100%, specifically between 70% and 100%, and more specifically between 80% and 100%, of the target detection signal {i.e. the amount of target bound by the coated amino acid sequence) as compared to the target detection signal obtained in the absence of the solution phase anti-target amino acid sequence (i.e. the positive control wells).

The amino acid residues of a Nanobody® are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, J. Immunol. Methods 2000 Jun. 23; 240 (1-2): 185-195 (see for example FIGS. 2A-2B of this publication); or referred to herein. According to this numbering, FR1 of a Nanobody® comprises the amino acid residues at positions 1-30, CDR1 of a Nanobody® comprises the amino acid residues at positions 31-35, FR2 of a Nanobody® comprises the amino acids at positions 36-49, CDR2 of a Nanobody® comprises the amino acid residues at positions 50-65, FR3 of a Nanobody® comprises the amino acid residues at positions 66-94, CDR3 of a Nanobody® comprises the amino acid residues at positions 95-102, and FR4 of a Nanobody® comprises the amino acid residues at positions 103-113. [In this respect, it should be noted that as is well known in the art for $V_H$ domains and for $V_{HH}$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.]. Alternative methods for numbering the amino acid residues of $V_H$ domains, which methods can also be applied in an analogous manner to $V_{HH}$ domains from Camelids and to Nanobodies®, are the method described by Chothia et al. (Nature 342, 877-883 (1989)), the so-called "AbM definition" and the so-called "contact definition". However, in the present description, claims and figures, the numbering according to Kabat as applied to $V_{HH}$ domains by Riechmann and Muyldermans will be followed, unless indicated otherwise.

By the term "target molecule" or "target molecules" or "target" is meant a protein with a biological function in an organism including bacteria and virus, preferably animal, more preferably mammal most preferred human, wherein said biological function may be involved in the initiation or progression or maintenance of a disease.

The terms "stability" and "stable" as used herein in the context of a formulation comprising a polypeptide comprising one or more single variable domains refer to the resistance of the polypeptide in the formulation to aggregation (and particularly dimerization and/or oligomerization) under given storage conditions. Apart from this and/or in addition, the "stable" formulations of the invention retain biological activity under given storage conditions. The stability of said polypeptide can be assessed by degrees of aggregation (and particularly dimerization and/or oligomerization as measured e.g. by SE-HPLC), and/or by % of biological activity (as measured e.g. by ELISA, Biacore, etc.) compared to a reference formulation. For example, a reference formulation may be a reference standard frozen at −2° C. or <−65° C. (such as e.g. −80° C.) consisting of the same polypeptide at the same concentration in D-PBS or consisting of the same polypeptide at the same concentration and in the same buffer as the stressed samples but without applying the stress conditions, which reference formulation regularly gives a single peak by SE-HPLC and/or keeps its biological activity in Biacore and/or ELISA.

The term "very little to no loss of the biological activities" as used herein refers to single variable domain activities, including but not limited to, specific binding abilities of the single variable domain to the target of interest as measured by various immunological assays, including, but not limited to ELISAs and/or by Surface Plasmon Resonance (Biacore).

In one embodiment, the single variable domains of the formulations of the invention retain at least 50%, preferably at least 55%, 60%, 65%, 70%, 75%, 80%, 85%, 90%, 95%, 98% or even 99% or more of the ability to specifically bind to an antigen as compared to a reference formulation, as measured by an immunological assay known to one of skill in the art or described herein. For example, an ELISA based assay (e.g. as described in the Example section) may be used to compare the ability of the single variable domain to specifically bind to its target. A "reference formulation" as used herein refers to a formulation that is frozen at a temperature of −20±5° C. or at <−64° C. (such as e.g. at −80° C.) consisting of the same single variable domain at the same concentration in D-PBS or consisting of the same single variable domains at the same concentration in the same buffer/excipients as the stressed samples but without applying the stress conditions, which reference formulation regularly gives a single peak by SE-HPLC and/or keeps its biological activity in Biacore and/or ELISA.

The phrase "pharmaceutically acceptable" as used herein means approved by a regulatory agency of the Federal or a state government, or listed in the U.S. Pharmacopeia, European Pharmacopoeia or other generally recognized pharmacopeia for use in animals, and more particularly in humans. In this sense, it should be compatible with the other ingredients of the formulation and not eliciting an unacceptable deleterious effect in the subject.

As used herein, the term "effective amount" refers to the amount of an agent (e.g. a prophylactic or therapeutic agent) which is sufficient to reduce and/or ameliorate the severity and/or duration of one or more diseases and/or disorders.

The term "polyol" as used herein refers to sugars that contains many hydroxyl (—OH) groups compared to a normal saccharide. Polyols include alcohols and carbohydrates such as mannitol, sorbitol, maltitol, xylitol, isomalt, erythritol, lactitol, sucrose, glucose, galactose, fructose, fucose, ribose, lactose, maltose and cellubiose.

As used herein, the terms "therapeutic agent" and "therapeutic agents" refer to any agent(s) which can be used in the prevention, treatment and/or management of one ore more diseases and/or disorders. In the context of the present invention, the term "therapeutic agent" refers to a polypeptide comprising one or more single variable domains. In certain other embodiments, the term "therapeutic agent" refers to an agent other than the polypeptide of the invention which might be used in the formulation.

As used herein, the term "therapeutically effective amount" refers to the amount of a therapeutic agent (e.g. a polypeptide comprising one or more single variable domains), that is sufficient to reduce the severity of one or more diseases and/or disorders.

The term "excipient" as used herein refers to an inert substance which is commonly used as a diluent, vehicle, preservative, binder or stabilizing agent for drugs which imparts a beneficial physical property to a formulation, such as increased protein stability, increased protein solubility, and/or decreased viscosity. Examples of excipients include, but are not limited to, proteins (e.g., serum albumin), amino acids (e.g., aspartic acid, glutamic acid, lysine, arginine, glycine), surfactants (e.g., SDS, Tween 20, Tween 80, poloxamers, polysorbate and nonionic surfactants), saccharides (e.g., glucose, sucrose, maltose and trehalose), polyols (e.g., mannitol and sorbitol), fatty acids and phospholipids (e.g., alkyl sulfonates and caprylate). For additional information regarding excipients, see Remington's Pharmaceutical Sciences (by Joseph P. Remington, 18th ed., Mack Publishing Co., Easton, Pa.), which is incorporated herein in its entirety.

The term "variable domain" refers to the part or domain of an immunoglobulin molecule or antibody which is partially or fully responsible for antigen binding. The term "single variable domain" or "immunoglobulin single variable domain" (used interchangeably), defines molecules wherein the antigen binding site is present on, and formed by, a single immunoglobulin domain. This sets single variable domains apart from "conventional" immunoglobulins or their fragments, wherein two immunoglobulin domains, in particular two "variable domains" interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of a single variable domain is formed by a single VH or VL domain. Hence, the antigen binding site of a single variable domain is formed by no more than three CDRs. The term "single variable domain" does comprise fragments of conventional immunoglobulins wherein the antigen binding site is formed by a single variable domain.

The single variable domains that are present in the constructs of the invention may be any variable domain that forms a single antigen binding unit. Generally, such single variable domains will be amino acid sequences that essentially consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's, as further described herein). Such single variable domains and fragments are most preferably such that they comprise an immunoglobulin fold or are capable for forming, under suitable conditions, an immunoglobulin fold. As such, the single variable domain may for example comprise a light chain variable domain sequence (e.g. a $V_L$-sequence) or a suitable fragment thereof; or a heavy chain variable domain sequence (e.g. a $V_H$-sequence or $V_{HH}$ sequence) or a suitable fragment thereof; as long as it is capable of forming a single antigen binding unit (i.e. a functional antigen binding unit that essentially consists of the single variable domain, such that the single antigen binding domain does not need to interact with another variable domain to form a functional antigen binding unit, as is for example the case for the variable domains that are present in for example conventional antibodies and ScFv fragments that need to interact with another variable domain—e.g. through a $V_H/V_L$ interaction—to form a functional antigen binding domain).

In one aspect of the invention, the single variable domains are light chain variable domain sequences (e.g. a $V_L$-sequence), or heavy chain variable domain sequences (e.g. a $V_H$-sequence); more specifically, the single variable domains can be heavy chain variable domain sequences that are derived from a conventional four-chain antibody or heavy chain variable domain sequences that are derived from a heavy chain antibody.

For example, the single variable domain may be a domain antibody (or an amino acid sequence that is suitable for use as a domain antibody), a single domain antibody (or an amino acid sequence that is suitable for use as a single domain antibody), a "dAb" or dAb (or an amino acid sequence that is suitable for use as a dAb) or a Nanobody® (as defined herein, and including but not limited to a $V_{HH}$ sequence); other single variable domains, or any suitable fragment of any one thereof. For a general description of (single) domain antibodies, reference is also made to the prior art cited above, as well as to EP 0 368 684. For the term "dAb's", reference is for example made to Ward et al. (Nature 1989 Oct. 12; 341 (6242): 544-6), to Holt et al., Trends Biotechnol., 2003, 21(11):484-490; as well as to for example WO 04/068820, WO 06/030220, WO 06/003388 and other published patent applications of Domantis Ltd. It should also be noted that, although less preferred in the context of the present invention because they are not of mammalian origin, single domain antibodies or single variable domains can be derived from certain species of shark (for example, the so-called "IgNAR domains", see for example WO 05/18629).

In particular, the amino acid sequence of the invention may be a Nanobody® or a suitable fragment thereof. [Note: Nanobody®, Nanobodies® and Nanoclone® are trademarks of Ablynx N.V.] For a further description of $V_{HH}$'s and Nanobodies®, reference is made to the review article by Muyldermans in Reviews in Molecular Biotechnology 74(2001), 277-302; as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies® (in particular $V_{HH}$ sequences and partially humanized Nanobodies®) can in particular be characterized by the presence of one or more "Hallmark residues" in one or more of the framework sequences. A further description of the Nanobodies®, including humanization and/or camelization of Nanobodies®, as well as other modifications, parts or fragments, derivatives or "Nanobody® fusions", multivalent constructs (including some non-limiting examples of linker sequences) and different modifications to increase the half-life of the Nanobodies® and their preparations can be found e.g. in WO07/104529, WO 08/101985 and WO 08/142164.

The total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein.

Thus, in the meaning of the present invention, the term "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as previously described.

In a specific aspect, the "single variable domain" is a "single variable VHH domain". The term "single variable VHH domain" indicates that the "single variable domain" is derived from a heavy chain antibody, preferably a camelid heavy chain antibody.

The term "single variable domain" also encompasses variable domains of different origin, comprising mouse, rat, rabbit, donkey, human and camelid variable domains; as well as fully human, humanized or chimeric variable domains. For example, the invention comprises camelid variable domains and humanized camelid variable domains, or camelized variable domains, e.g. camelized dAb as described by Ward et al (see for example WO 94/04678 and Davies and Riechmann (1994, FEBS Lett. 339(3): 285-290) and (1996, Protein Eng. 9(6): 531-537)). Moreover, the invention comprises fused variable domains, e.g. multivalent and/or multispecific constructs (for multivalent and multispecific polypeptides containing one or more $V_{HH}$ domains and their preparation, reference is also made to Conrath et al. 2001 (J. Biol. Chem. 276: 7346-7350) as well as to for example WO 96/34103 and WO 99/23221).

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). The terms antigen-binding molecules or antigen-binding protein are used interchangeably with immunoglobulin sequence, and include Nanobodies.

The single variable domains provided by the invention are preferably in essentially isolated form (as defined herein), or form part of a polypeptide of the invention (as defined herein), which may comprise or essentially consist of one or more single variable domains and which may optionally further comprise one or more further amino acid sequences (all optionally linked via one or more suitable linkers). For example, and without limitation, the one or more single variable domains may be used as a binding unit in such a polypeptide, which may optionally contain one or more further amino acid sequences that can serve as a binding unit (i.e. against one or more other targets), so as to provide a monovalent, multivalent or multispecific polypeptide of the invention, respectively as e.g. described in WO 08/101985, WO 08/142164, WO 09/068625, WO 09/068627 and WO 08/020079. Such a protein or polypeptide may also be in essentially isolated form (as defined herein) and the methods of the present invention for the expression and/or production of single variable domains equally apply to polypeptides comprising one or more single variable domains.

According to the invention, the term "single variable domain" may comprise constructs comprising two or more antigen binding units in the form of single variable domain, as outlined above. For example, two (or more) variable domains with the same or different antigen specificity can be linked to form e.g. a bivalent, trivalent or multivalent construct. By combining variable domains of two or more specificities, bispecific, trispecific etc. constructs can be formed. For example, a variable domain according to the invention may comprise two variable domains directed against target A, and one variable domain against target B.

Such constructs and modifications thereof, which the skilled person can readily envisage, are all encompassed by the term variable domain as used herein and are also referred to as "polypeptide of the invention" or "polypeptides of the invention".

The polypeptide comprising one or more single variable domains for use in the formulation of the invention may be therapeutic or prophylactic, and may be useful in the treatment and/or management of one or more diseases. In one specific aspect, the polypeptide has at least one single variable domain. In another specific aspect, the polypeptide has at least two single variable domains. In yet another specific aspect, the polypeptide has at least three single variable domains. Preferably, the polypeptide comprises at least one single variable domain directed against HSA. In another specific aspect, the polypeptide comprises at least a single variable domain against RANKL. In another specific aspect, the polypeptide comprises at least a single variable domain against IL-6R. More preferably, the polypeptide is directed against and/or specifically binds HSA as well as another target such as RANKL or IL-6R. In yet another aspect, polypeptide comprises at least a single variable domain against RANKL and at least a single variable domain against HSA. In yet another aspect, polypeptide comprises at least a single variable domain against IL-6R and at least a single variable domain against HSA. In yet another aspect, polypeptide comprises at least two single variable domains against one target and at least a single variable domain against HSA. In yet another aspect, polypeptide comprises at least two single variable domains against RANKL and at least a single variable domain against HSA. In yet another aspect, polypeptide comprises at least two single variable domains against IL-6R and at least a single variable domain against HSA. In a preferred aspect, the single variable domains used in the polypeptide of the invention are selected from WO 08/142164 (such as e.g. SEQ ID NO's: 745 and/or 791 of WO 08/142164), WO 08/020079, WO 09/068627 (such as e.g. SEQ NO's 2578, 2584 and/or 2585 of WO 09/068627), U.S. provisional application No. 61/168,379 by Ablynx N.V., U.S. provisional application No. 61/168,410 by Ablynx N.V. (such as e.g. SEQ ID NO's: 77 and/or 109 of U.S. 61/168,410) and WO 08/028977 (such as e.g. SEQ ID NO: 62 of WO 08/028977). Preferred polypeptides of the invention are selected from SEQ ID NO's: 1 to 6 and 11 to 14.

The term "non-fused" in the context of 'non-fused dimers' means every stable linkage (or also more specific conditions herein mentioned as "stable") existing under normal (e.g. storage and/or physiological) conditions which is not obtained via a direct genetic linkage or via a dedicated dimerization sequence as known in the literature (e.g. Jun-Fos interaction, interaction of CH2-CH3 domains of heavy-chains etc). Such linkage may be due to for example through chemical forces such as Van der Waal's forces, hydrogen bonds, and/or forces between peptides bearing opposite charges of amino acid residues. Furthermore, additional components such as structural changes may play a role. Such structural changes may e.g. be an exchange of framework regions, e.g. exchange of framework region 4 (a phenomenon also called "domain swapping pattern") beta strands derived from framework regions and may be prevented by stabilizing CDR3-FR4 region in the monomeric structure conformation. In contrast in a genetically linked or -fused construct, the fusion is forcing two entities to be expressed as a fusion protein, and the linkage is of a covalent nature (e.g. using peptide linkers between the two entities, linking the C-terminus of one with the N-terminus of the other protein domain). The term "stable" in the context of "stable dimer" or "stable NFD" ("stable NFDs") means that 50%, more preferably 60%, more preferably 70%, more preferably 80%, even more preferably 90%, even more preferably 95%, most preferred 99% are in the form of NFDs at the time point of measurement; wherein 100% represents the amount (e.g. molar amount per volume or weight per volume amount) of NFD and its corresponding monomer. Measurement of stability as defined herein, i.e. with regards to its dimeric nature, may be done by using size exclusion chromatography (using standard laboratory conditions such as PBS buffer at room temperature) and if required a pre-concentration step of the sample to be tested. The area under the peak in the size exclusion chromatogram of the identified dimeric and monomeric peak represents the relative amounts of the monomer and dimer, i.e. the NFD, NFD and/or NFDs are used herein interchangeably, thus wherever NFD is used NFDs are meant as well and vice versa.

A polypeptide or single variable domain that is "susceptible to dimerization", as used in the present invention, means that the respective polypeptide or single variable domain, under the specified conditions described in the present application (e.g. In a process called process-induced association and/or e.g. under stressful storage conditions, such as relative high temperature (e.g. 37° C.) over weeks (such as e.g. 4 weeks)), converts its otherwise stable monomeric single variable domains into stable dimeric molecules (i.e. NFDs as described herein).

Non-Fused-Dimers (NFDs)

Certain conditions or amino acid sequence alterations can convert otherwise stable monomeric single variable domains into stable dimeric and in certain instances multimeric molecules. Key in this process is to provide conditions in which two single variable domains are able to display an increased non-covalent interaction. NFDs are made e.g. in a process called process-induced association (hereinafter also "PIA"). This dimerization is among others a concentration driven event and can e.g. be enhanced by combining high protein concentrations (e.g. higher than 50 mg protein/ml), rapid pH shifts (e.g. pH shift of 2 units within 1 column volume) and/or rapid salt exchanges (e.g. salt exchange with 1 column volume) in the preparation process. The high concentration will enhance the likelihood of interactions of individual monomeric molecules while the pH and salt changes can induce transiently (partial) unfolding and/or promote hydrophobic interactions and/or rearrangement of the protein structure. Because these NFDs may ultimately be used in or as a therapeutic or prognostic agent, the term "NFD" or "NFDs" are meant to mean (or to be interchanged) that the NFD is in solution, e.g. in a physiological preparation, e.g. physiological buffer, comprising NFD or NFDs (unless the condition, e.g. a condition of special sorts, e.g. storage condition for up to 2.5 years for which a NFD is stable, is specifically described). Alternatively, NFDs can also be made under stressful storage conditions e.g. such as relative high temperature (e.g. 37° C.) over weeks such as e.g. 4 weeks. Furthermore, NFDs can be made (even with improved, i.e. faster, kinetics) by introducing destabilizing amino acid residues in the vicinity of the CDR3 and/or the framework region 4 of the single variable domain susceptible to dimerize (see experimental part, polypeptide F (=mutated polypeptide B) is forming NFDs more quickly than polypeptide B under the same conditions).

Attaining a high concentration of the components that have to dimerize can be obtained with a variety of procedures that include conditions that partially unfold the immunoglobulinic structure of the single variable domains, e.g.

Nanobodies®, e.g. via chromatography (e.g. affinity chromatography such as Protein A, ion exchange, immobilized metal affinity chromatography or IMAC and Hydrophobic Interaction Chromatography or HIC), temperature exposure close to the Tm of the single variable domain, and solvents that are unfolding peptides such as 1 to 2 M Guanidinium Hydrochloride. E.g. for chromatography—during the process of elution of the proteins off the column using e.g. a pH shift or salt gradient (as explained later), the NFDs can be formed. Usually the required concentration and/or exact method to form NFDs has to be determined for each polypeptide of the invention and may not be possible for each polypeptide of the invention. It is our experience that there are certain single variable domains either alone (e.g. polypeptides B and F) and/or in a construct (e.g. polypeptides A, C, E, F) that form a NFD. Critical for dimerization may be a relative short CDR3 (e.g. 3 to 8 amino acids, more preferably 4 to 7 amino acids, even more preferably 5 to 6 amino acids, e.g. 6 amino acids) and destabilizing factors in the vicinity of the CDR3 and/or FR4. Furthermore, high concentration such as e.g. the maximum solubility of the polypeptides comprising single variable domain(s) at the concentration used (e.g. 5 mg polypeptide A per ml protein A resin—see experimental part), or storage at high temperature over weeks (e.g. 37° C. over 4 weeks), low pH (e.g. pH below pH 6), high concentration (higher than 50 mg/ml, e.g. 65 mg/ml) may be required to obtain a reasonable yield of NFD formation.

Next to column chromatography working at e.g. maximum column load, similar required high concentration to obtain NFDs can be achieved by concentration methods such as ultrafiltration and/or diafiltration, e.g. ultrafiltration in low ionic strength buffer.

The process is not linked to a specific number of single variable domains, as the formation of NFDs was observed with monovalent, bivalent and trivalent monomeric building blocks (=polypeptides comprising single variable domain (s)) and even with single variable domain-HSA fusions. In case the polypeptides comprises 2 different single variable domains, NFDs may form via only the identical or different (preferably the identical) single variable domain and usually only via one of the single variable domain(s), e.g. the one identified as susceptible to form NFDs (e.g. polypeptide B) (see also FIG. 2B).

Figure 2B:
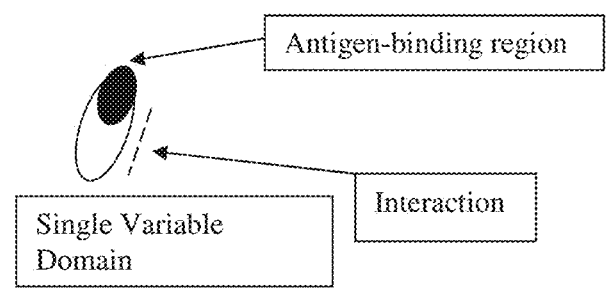

It is an object of the present invention to provide soluble and stable (e.g. stable within a certain concentration range, buffer and/or temperature conditions) dimer-complexes called NFDs that may be used to target molecules and/or thus inhibit or promote cell responses. Herein described are NFDs comprising monomeric building blocks such as single variable domain—also called NFDs-Mo; NFDs comprising dimeric building blocks such as two covalently linked single variable domains—also called NFDs-Di; NFDs comprising trimeric building blocks such as three covalently linked single variable domains—also called NFDs-Tri; NFDs comprising tetrameric building blocks such as four covalently linked single variable domains—also called NFDs-Te; and NFDs comprising more than four (=multimeric) building blocks such as multimeric covalently linked single variable domains—also called NFDs-Mu (see FIGS. 2A-2B for schematic overview of such structures). The NFDs may contain identical single variable domains or different single variable domains (FIG. 2B). If the building blocks (polypeptide) consist of different single variable domains, e.g. Nanobodies®, it is our experience that preferably only one of the single variable domain in the polypeptide will dimerize. E.g. the dimerizing unit (single variable domain, e.g. Nanobody® such as e.g. polypeptide B or F) of a trivalent polypeptide (see FIG. 2B) may be in the middle, at the C-terminus or at the N-terminus of the construct.

It is another object of the invention to provide methods of making and uses of said NFDs.

It is still another object of the present invention to provide information on how to avoid such NFDs.

These above and other objectives are provided for by the present invention which, in a broad sense, is directed to methods, kits, non-fused-dimers that may be used in the treatment of neoplastic, immune or other disorders. To that end, the present invention provides for stable NFDs comprising a single variable domain or single variable domains such as e.g. Nanobody® or Nanobodies® (e.g. polypeptide B) that may be used to treat patients suffering from a variety of disorders. In this respect, the NFDs of the present invention have been surprisingly found to exhibit biochemical characteristics that make them particularly useful for the treatment of patients, for the diagnostic assessment of a disease in patients and/or disease monitoring assessment in patients in need thereof. More specifically, it was unexpectedly found that certain single variable domains, subgroups thereof (including humanized VHHs or truly camelized human VHs) and formatted versions thereof (and indeed this is also feasible for human VH and derivatives thereof), can be made to form stable dimers (i.e. NFD-Mo, NFD-Di, NFD-Tri, NFD-Te or NFD-Mu) that have beneficial properties with regard e.g. to manufacturability and efficacy. Single variable domains are known to not denature upon for example temperature shift but they reversibly refold upon cooling without aggregation (Ewert et al Biochemistry 2002, 41:3628-36), a hallmark which could contribute to efficient formation of antigen-binding dimers.

NFDs are of particular advantage in many applications. In therapeutic applications, NFDs-Mu, e.g. NFD-Di, binders may be advantageous in situation where oligomerization of the targeted receptors is needed such as e.g. for the death receptors (also referred to as TRAIL, receptor). E.g. a NFD-Di due to their close interaction of the respective building blocks are assumed to have a different spatial alignment than "conventional" covalently linked corresponding tetramers and thus may provide positive or negative effect on the antigen-binding (see FIGS. 2A-2B for a schematic illustration of certain NFDs). Furthermore, a NFDs, e.g. a NFD-Mo, may bind a multimeric target molecule more effectively than a conventional covalently linked single variable domain dimer. Moreover, heteromeric NFDs may comprise target specific binders and binders to serum proteins, e.g. human serum albumin, with long half life. In addition, "conventional" covalently linked dimers (via e.g. amino acid sequence linkers) may have expression problems (by not having enough tRNA available for certain repetitive codons) and thus it may be advantageous to make the monomers first and than convert the monomers to a NFD in a post-expression process, e.g. by a process described herein. This may give yields that are higher for the NFD compared to the covalently linked dimer. Similarly, it may be expected that e.g. the overall yield of a NFD-Di or NFD-Tri will be higher compared to the relevant covalently linked tetramer or hexamer. The overall higher expression level may be the overriding factor in e.g. cost determination to select the NFD approach. E.g. it is reported that expression yields and secretion efficiency of recombinant proteins are a function of chain size (Skerry & Pluckthun, 1991, Protein Eng. 4, 971). Moreover, less linker regions could mean less protease susceptible linker regions on the overall protein. It could also be useful to test in vitro and/or in vivo the impact of multimerization of a single variable domain according to the methods described herein. All in all, it is expected that the finding of this invention may provide additional effective solutions in the drug development using formatted single variable domains as the underlying scaffold structure than with the hitherto known approaches, i.e. mainly covalently linked single variable domain formats.

The NFDs of the present invention can be stable in a desirable range of biological relevant conditions such as a wide range of concentration (i.e. usually low nM range), temperature (37 degrees Celsius), time (weeks, e.g. 3 to 4 weeks) and pH (neutral, pH5, pH6 or in stomach pH such as pH 1). In a further embodiment, NFDs of the present invention can be stable (at a rate of e.g. 95% wherein 100% is the amount of monomeric and dimeric form) in vivo, e.g. in a human body, over a prolonged period of time, e.g. 1 to 4 weeks or 1 to 3 months, and up to 6 to 12 months. Furthermore, the NFDs of the present invention can also be stable in a desirable range of storage relevant conditions such as a wide range of concentration (high concentration such as e.g. mg per ml range), temperature (−20 degrees Celsius, 4 degrees Celsius, 20 or 25 degrees Celsius), time (months, years), resistance to organic solvents and detergents (in formulations, processes of obtaining formulations). Furthermore, it has been surprisingly found that denaturation with guanidine HCl (GdnHCl) needs about 1 M more GdnHCl to denature the polypeptide B dimer than the polypeptide B monomer in otherwise same conditions (see experimental part). Additionally, the surprising finding that FR4 in the polypeptide B NFD-Mo is swapped (and possibly similarly for other NFDs according to the invention) indicates that indeed this dimers form stable complexes and can further stabilize single variable domain or Nanobody® structures. Furthermore, there is evidence that one of the humanisation sites (see experimental part: polypeptide E vs. polypeptide B) may have caused a weaker CDR3 interaction with the framework and thus a more extendable CDR3 is available that is more likely to trigger dimerization.

Thus, preferred NFDs of the invention are stable (with regards to the dimeric nature) within the following ranges (and wherein said ranges may further be combined, e.g. 2, 3, 4 or more ranges combined as described below, to form other useful embodiments):

Preferred embodiments of NFDs are stable (with regards to the dimeric nature) under physiological temperature conditions, i.e. temperature around 37 degrees Celsius, over a prolonged time period, e.g. a time up to 1 day, more preferably 1 week, more preferably 2 weeks, even more preferably 3 weeks, most preferred 4 weeks from the time point of delivery of the drug to the patient in need;

Preferred embodiments of NFDs are stable (with regards to the dimeric nature) under various storage temperature conditions, i.e. temperatures such as −20 degrees Celsius, more preferably 4 degrees Celsius, more preferably 20 degrees Celsius, most preferably 25 degrees Celsius, over a prolonged time period, e.g. up to 6 months, more preferably 1 year, most preferred 2 years;

Preferred embodiments of NFDs are stable (with regards to the dimeric nature) under various physiological pH conditions, i.e. pH ranges such as pH 6 to 8, more preferably pH 5 to 8, most preferred pH 1 to 8, over a prolonged time period, e.g. a time up to 1 week, more preferably 2 weeks, even more preferably 3 weeks, most preferred 4 weeks from the time point of delivery of the drug to the patient in need;

Preferred embodiments of NFDs are stable (with regards to the dimeric nature) under various physiological concentration conditions, i.e. concentration of NFDs below 200 ng NFD/ml solvents, e.g. in pH 7 buffer such as phosphate buffered solution and/or e.g. also serum, e.g. human serum; more preferably below 100 ng NFD/ml solvents, even preferably below 50 ng NFD/ml solvents, most preferred 10 ng NFD/ml solvents; in a further preferred embodiment NFDs are stable in above concentrations at 37 degrees Celsius up to 1 day and more, e.g. 1 week, more preferably 2 weeks, more preferably 3 weeks, and most preferred up to 4 weeks;

Preferred embodiments of NFDs are stable (with regards to the dimeric nature) under various physiological concentration conditions, i.e. concentration of NFDs of about 1 mg/ml, more preferably 5 mg/ml, more preferably 10 mg/ml, more preferably 15 mg/ml, more preferably 20 mg/ml, more preferably 30 mg/ml, more preferably 40 mg/ml, more preferably 50 mg/ml, more preferably 60 mg/ml, more preferably 70 mg/ml, and at temperature around 37 degrees Celsius, over a prolonged time period, e.g. a time up to 1 day, more preferably 1 week, more preferably 2 weeks, even more preferably 3 weeks, most preferred 4 weeks from the time point of delivery of the drug to the patient in need;

Preferred embodiments of NFDs are stable (with regards to the dimeric nature) under various storage concentration conditions, i.e. concentration of NFDs above 0.1 mg NFD/ml solvents, e.g. in pH 7 buffer such as phosphate buffered solution; more preferably above 1 mg NFD/ml solvents; more preferably above 5 mg NFD/ml solvents; more preferably above 10 mg NFD/ml solvents, and most preferred above 20 mg NFD/ml solvents; in a further preferred embodiment NFDs are stable in above concentrations at −20 degree Celsius up to 6 months and more, e.g. 1 year, more preferably 2 years, more preferably 3 years, and most preferred up to 4 years; in a further preferred embodiment NFDs are stable in above concentrations at 4 degrees Celsius up to 6 months and more, e.g. 1 year, more preferably 2 years, more preferably 3 years, and most preferred up to 4 years; in a further preferred embodiment NFDs are stable in above concentrations at 25 degrees Celsius up to 6 months and more, e.g. 1 year, more preferably 2 years, more preferably 3 years, and most preferred up to 4 years;

Preferred embodiments of NFDs are stable (with regards to the dimeric nature) mixtures (e.g. pharmaceutical formulations or process intermediates) with organic solvents, e.g. alcohols such as ethanol, isopropyl alcohol, hexanol and/or others wherein alcohol (preferably ethanol) can be added up to 5%, more preferably 10%, even more preferably 15%, even more preferably 20%, most preferably 30%, for prolonged period of time at a particular temperature, e.g. over long storages, such as at −20 degrees Celsius up to 6 months and more, e.g. 1 year, more preferably 2 years, more preferably 3 years, and most preferred up to 4 years; in a further preferred embodiment NFDs are stable in above mixtures at 4 degrees Celsius up to 6 months and more, e.g. 1 year, more preferably 2 years, more preferably 3 years, and most preferred up to 4 years; in a further preferred embodiment. NFDs are stable in above mixtures at 25 degrees Celsius up to 6 months and more, e.g. 1 year, more preferably 2 years, more preferably 3 years, and most preferred up to 4 years, wherein organic solvents such as e.g. alcohol (preferably ethanol) can be added up to 5%, more preferably 10%, even more preferably 15%, even more preferably 20%, most preferably 30%;

Preferred embodiments of NFDs are stable (with regards to the dimeric nature) in mixtures (e.g. pharmaceutical formulations or process intermediates) with detergents, e.g. non-ionic detergents such as e.g. Triton-X, up to 0.01%, more preferably 0.1%, most preferably 1%, for prolonged period of time at a particular temperature, e.g. over long storages, such as at −20 degrees Celsius up to 6 months and more, e.g. 1 year, more preferably 2 years, more preferably 3 years, and most preferred up to 4 years; in a further preferred embodiment NFDs are stable in above mixtures at 4 degrees Celsius up to 6 months and more, e.g. 1 year, more preferably 2 years, more preferably 3 years, and most preferred up to 4 years; in a further preferred embodiment NFDs are stable in above mixtures at 25 degrees Celsius up to 6 months and more, e.g. 1 year, more preferably 2 years, more preferably 3 years, and most preferred up to 4 years.

Another embodiment of the current invention is that the NFDs retain the binding affinity of at least one of the two components compared to the monomers, e.g. said affinity of the NFDs may be not less than 10%, more preferably not less than 50%, more preferably not less than 60%, more preferably not less than 70%, more preferably not less than 80%, or even more preferably not less than 90% of the binding affinity of the original monomeric polypeptide; or it has multiple functional binding components, with apparent affinity improved compared to the monomer, e.g. it may have a 2 fold, 3, 4, 5, 6, 7, 8, 9 or 10 fold, more preferably 50 fold, more preferably 100 fold more preferably 1000 fold improved affinity compared to the original monomeric polypeptide.

Another embodiment of the current invention is that the NFDs partially or fully lose the binding affinity of at least one of the two components compared to the monomers, e.g. said affinity of the NFDs may be not less than 90%, more preferably not less than 80%, more preferably not less than 70%, more preferably not less than 60%, more preferably not less than 50%, even more preferably not less than 30%, even more preferably not less than 20%, even more preferably not less than 10%, or even more preferably not less than 1% of the binding affinity of the original monomeric polypeptide or most preferred the binding affinity may not be detectable at all; or it has multiple functional binding components, with apparent affinity compared to the monomer that is decreased, e.g. it may have a 2 fold, 3, 4, 5, 6, 7, 8, 9 or 10 fold, more preferably 50 fold, more preferably 100 fold more preferably 1000 fold decreased affinity compared to the original monomeric polypeptide.

Furthermore, an embodiment of the current invention is a preparation comprising NFDs and their monomeric building blocks, e.g. preparations comprising more than 30% NFDs (e.g. the 2 identical monomeric building blocks that form said NFD), e.g. more preferably preparations comprising more than 35% NFDs, even more preferably preparations comprising more than 40% NFDs, even more preferably preparations comprising more than 50% NFDs, even more preferably preparations comprising more than 60% NFDs, even more preferably preparations comprising more than 70% NFDs, even more preferably preparations comprising more than 80% NFDs, even more preferably preparations comprising more than 90% NFDs, even more preferably preparations comprising more than 95% NFDs, and/or most preferred preparations comprising more than 99% NFDs (wherein 100% represents the total amount of NFDs and its corresponding monomeric unit). In a preferred embodiment, said ratios in a preparation can be determined as e.g. described herein for NFDs.

Moreover, another embodiment of the current invention is a pharmaceutical composition comprising NFDs, more preferably comprising more than 30% NFDs (e.g. the 2 identical monomeric building blocks form said NFD), e.g. more preferably a pharmaceutical composition comprising more than 35% NFDs, even more preferably a pharmaceutical composition comprising more than 40% NFDs, even more preferably a pharmaceutical composition comprising more than 50% NFDs, even more preferably a pharmaceutical composition comprising more than 60% NFDs, even more preferably a pharmaceutical composition comprising more than 70% NFDs, even more preferably a pharmaceutical composition comprising more than 80% NFDs, even more preferably a pharmaceutical composition comprising more than 90% NFDs, even more preferably a pharmaceutical composition comprising more than 95% NFDs, and/or most preferred a pharmaceutical composition comprising more than 99% NFDs (wherein 100% represents the total amount of NFDs and its corresponding monomeric unit).

Another embodiment of the present invention is a mixture comprising polypeptides in monomeric and dimeric form, i.e. the NFDs, wherein said preparation is stable for 1 months at 4 degrees Celsius in a neutral pH buffer in a 1 mM, more preferably 0.1 mM, more preferably 0.01 mM, more preferably 0.001 mM, or most preferably 100 nM overall concentration (=concentration of monomeric and dimeric form), and wherein said preparation comprises more than 25%, more preferably 30%, more preferably 40%, more preferably 50%, more preferably 60%, more preferably 70%, more preferably 80% or more preferably 90% dimer, i.e. NFD.

While the methodology described here is or may be in principle applicable to dimerize or multimerize either Fab fragments, Fv fragments, scFv fragments or single variable domains, it is the latter for which their use is most advantageous. In this case dimeric fragments, i.e. the NFDs, can be constructed that are stable, well defined and extend the applicability of said single variable domains beyond the current horizon. In a preferred embodiment, the NFDs are obtainable from naturally derived VHH, e.g. from llamas or camels, according to the methods described herein or from humanized versions thereof, or humanized versions wherein one or more of the so called hallmark residues, e.g. the ones forming the former light chain interface residues, also e.g. described in WO 2006/122825, or in FIG. 1 herein, are not changed and stay as derived from the naturally obtained single variable domains. In a further preferred embodiment, the NFDs are obtainable from polypeptides comprising at least a single domain antibody (or Nanobody®) with similar CDR3 and FR4 amino acid residues (SEQ ID NO: 8) as polypeptide B, e.g. NFDs obtainable from polypeptides comprising at least a Nanobody® having a CDR3 and FR4 region that has a 80%, more preferably 90%, even more preferably 95%, 96%, 97%, 98%, 99% sequence identity to SEQ ID NO: 8.

Previously, increasing the number of binding sites based on single variable domains meant the preparation of covalently linked domains at the genetic level or via other interaction domains (e.g. via fusion to Fc, Jun-Fos, CH2/CH3 constant domain of heavy chain interaction, VL-VH antibody domain interactions etc), whereas now it is possible to alternatively form such entities later, at the protein level. These non-fused dimers combine three main features: (a) possibility to combine one or more single variable domains of one or more specificities (e.g. against a target molecule and against a serum protein with long half life) into NFDs by biochemical methods (vs. genetic methods), (b) controlled dimeric interaction that retains or abolishes antigen binding (vs. "uncontrolled" aggregation), and (c) stability sufficient e.g. for long term storage (for practical and economic reasons) and application in vivo, i.e. for application over prolonged time at e.g. 37 degrees Celsius (important requirement for the commercial use of these NFDs).

Thus, it is a further object of the invention to create new individual and stable NFDs with bi- or even multifunctional binding sites. It has been found that antibody fragment fusion proteins containing single variable domains could be produced by biochemical methods which e.g. show the specified and improved properties as described herein. For example, a particular embodiment of the present invention is a NFD or NFDs comprising a first polypeptide comprising single variable domain(s), e.g. a Nanobody® or Nanobodies®, against a target molecule and a second polypeptide comprising single variable domain(s), e.g. a Nanobody® or Nanobodies®, against a serum protein, e.g. human serum albumin (see e.g. polypeptide C and E (each binding a receptor target and human serum albumin) in the experimental part, see also FIGS. 2A-2B). Other examples of using bispecificity can be found in Kufer et al, Trends in Immunology 22:238 (2004). In the case in which two different antigen-binding single variable domains are used, the procedure to produce NFDs may be tweaked to promote the formation of heterodimers versus homodimers, or alternatively be followed by a procedure to separate these forms.

Moreover, it is an object of the invention, therefore, to provide (or select) in a first step a monomeric polypeptide essentially consisting of a single variable domain, wherein said polypeptide is capable to dimerize with itself by process-induced association (PIA) or other alternative methods described herein.

More specifically, we describe in this invention NFDs obtainable by e.g. a method that comprises the step of screening for preparations comprising antibody fragments or polypeptides comprising single variable domain(s) that form dimers by the processes as described herein. Hence said screening method comprising identifying said polypeptides may be a first step in the generation of NFDs. Multiple 'PIA' methods described herein can be used to force dimer formation in a starting preparation comprising its monomeric building block(s). An indication that dinners may be formed under suitable conditions, e.g. the process induced association (PIA) as described herein, is sufficient at this time and may simply mean that a small amount of e.g. the protein A purified fraction in the size exclusion chromatography is eluting as a presumable dimer in the standard purification protocol. Once the dimerization is suggested and later confirmed (e.g. by analytical SEC, dynamic light scattering and/or analytical ultracentrifugation) further improvement in order to favour dimerization (e.g. by higher column load, conditions favouring partial unfolding, conditions favouring hydrophobic interactions, high temperature such as e.g. 37° C. exposure of some time, e.g. weeks such as e.g. 4 weeks, introduction of CDR3 destabilizing amino acid residues etc) r in order to minimize dimerization (opposite strategy) can be initiated (in order to e.g. increase the yield).

The invention relates, furthermore, to a process of selection of a monomeric polypeptide that comprises at least one single variable domain, preferably at least one Nanobody®, capable of forming a NFD according to the invention and as defined herein, characterized in that the NFD is stable and preferably has a similar or better apparent affinity to the target molecule than the monomeric polypeptide showing that the binding site is active or at least is partially active. Said affinity may be not less than 10%, more preferably 50%, more preferably not less than 60%, more preferably not less than 70%, more preferably not less than 80%, or even more preferably not less than 90% of the binding affinity of the original monomeric polypeptide, e.g. may have a 2 fold, 3, 4, 5, 6, 7, 8, 9 or 10 fold, more preferably 50 fold, more preferably 100 fold more preferably 1000 fold improved apparent affinity compared to original monomeric polypeptide. Said affinity may be expressed by features known in the art, e.g. by dissociation constants, i.e. Kd, affinity constants, i.e. Ka, koff and/or kon values—these and others can reasonably describe the binding strength of a NFD to its target molecule.

Moreover, the invention relates, furthermore, to a process of selection of a monomeric polypeptide that comprises at least one single variable domain, preferably at least one Nanobody®, capable of forming a NFD according to the invention and as defined herein, characterized in that the NFD is stable and preferably has no apparent affinity to the target molecule, e.g. human serum albumin.

Said selection may comprise the step of concentrating the preparation comprising the monomeric starting material, i.e. the polypeptide comprising or essentially consisting of at least one single variable domain, to high concentration, e.g. concentration above 5 mg/ml resin, by methods known by the skilled person in the art, e.g. by loading said polypeptide to a column, e.g. protein A column, to the near overload of the column capacity (e.g. up to 2 to 5 mg polypeptide per ml resin protein A) and then optionally eluting said polypeptide with a "steep" pH shift ("steep" meaning e.g. a particular pH shift or change (e.g. a decrease or increase of 10, more preferably 100 or more preferably 1000 fold of the H+ concentration) one step (i.e. immediate buffer change) or within one, two or three (more preferably one or immediate buffer change) column volume(s)). Furthermore, the "steep" pH shift may be combined with a selected pH change, i.e. the pH can start above or below the pI of polypeptide and then change into a pH below or above the pI of said polypeptide. Alternatively, concentration of said polypeptides leading to NFD formation is obtainable by other means such as e.g. immobilized metal ion affinity chromatography (IMAC), or ultra-filtration. Preferably conditions are used wherein the polypeptides of the invention are likely to unfold (extremes in pH and high temperature) and/or combinations of conditions favouring hydrophobic interaction such as e.g. pH changes around the pI of the polypeptide and low salt concentration. Furthermore, the conditions used to drive these dimers apart may be also useful to explore when determining further methods for producing these dimers, i.e. combining these procedures (e.g. 15 minutes of exposure to a temperature of about 70 degrees Celsius for Polypeptide A with a high polypeptide concentration and subsequent cooling).

Examples of methods to obtain NFDs are further described in a non limiting manner in the experimental part of this invention.

Another object of the invention is the process to obtain a NFD characterized in that the genes coding for the complete monomeric polypeptide comprising at least one single variable domain (e.g. one, two, three or four single variable domain(s)) or functional parts of the single variable domain (s) (e.g. as obtained by the screening method described herein) are cloned at least into one expression plasmid, a host cell is transformed with said expression plasmid(s) and cultivated in a nutrient solution, and said monomeric polypeptide is expressed in the cell or into the medium, and in the case that only parts of the fusion proteins were cloned, protein engineering steps are additionally performed according to standard techniques.

Furthermore, another object of the invention is the process of associating two monomeric identical polypeptides comprising at least one single variable domain (e.g. one, two, three or four single variable domain(s)) or functional parts of the single variable domain(s) to form a NFD, wherein said process comprises the step of creating an environment where hydrophobic interactions and/or partial refolding of said polypeptides are favoured e.g. by up-concentrating a preparation comprising the monomeric polypeptides, salting-out, adding detergents or organic solvents, neutralizing the overall charge of said polypeptide (i.e. pH of polypeptide solution around the pI of said polypeptide or polypeptides) and/or high temperature close to the melting temperature of the polypeptide or the single variable domain susceptible to dimerization, e.g. at temperature around 37° C. or higher e.g. 40° C., 45° C. or 50° C. or higher over a prolonged time, e.g. weeks such as e.g. 1, 2 3, 4 or more weeks, preferably 4 weeks during dimerization process thus allowing close interaction between the polypeptides. Interestingly and surprisingly said conditions do not have to be upheld in order to stabilize the NFDs once the dimer is formed, i.e. the NFDs in solution are surprisingly stable in a wide range of biological relevant conditions such as mentioned herein.

The NFDs according to the invention may show a high avidity against corresponding antigens and a satisfying stability. These novel NFD structures can e.g. easily be prepared during the purification process from the mixture of polypeptides and other proteins and/or peptides obtained by the genetically modified prokaryotic or eukaryotic host cell such as e.g. *E. coli* and *Pichia pastoris*.

Furthermore, the monomeric building blocks capable of forming NFDs may be pre-selected before doing a process for selection or screening as above and further herein described by taking into consideration primary amino acid sequences and crystal structure information if available. Moreover, in order to understand the potential interactions in these non-fused protein domains, it may be advisable to analyze different X-ray or NMR structures of non-fused single variable domains, i.e. NFDs. This then exemplifies how possibly in solution interactions in NFDs can occur but this is by no means then a complete explanation for the likely area of interaction between the NFD components.

Furthermore, further stabilization of the dimer may be beneficial and may be done by suitable linker linking the ends of the polypeptides and/or cysteines at the interaction sites. E.g. a covalent attachment of the two domains may be possible by introducing 2 cysteines in each of the two building blocks at spatially opposite positions to force formation of a disulphide bridge at the new site of interaction, or at N- or C-terminal region of the NH) as has e.g. been done with diabodies (Holliger & Hudson, Nat Biotech 2004, 23 (9): 1126). Furthermore, it may be advantageous to introduce a flexible peptide between the ends of the two monomeric building blocks. As an example, the upper hinge region of mouse IgG3 may be used. However, a variety of hinges or other linkers may be used. It is not required for dimerization per se, but provides a locking of the two building blocks. The naturally occurring hinges of antibodies are reasonable embodiments of hinges. In such case, the polypeptides of the invention need to be present first under reducing conditions, to allow the NFDs to form during purification after which oxidation can lead to the cysteine pairings, locking the NFDs into a fixed state. In the case of NFDs, the hinges or linkers may be shorter than in conventional covalently linked single variable domain containing polypeptides. This is not to disturb the expected close interaction of the monomeric building blocks, and flexibility of the dimer is not necessary. The choice of the hinge is governed by the desired residue sequence length (Argos, 1990, J. Mol. Biol. 211, 943-958), compatibility with folding and stability of the dimers (Richardson & Richardson, 1988, Science 240, 1648-1652), secretion and resistance against proteases, and can be determined or optimized experimentally if needed.

Furthermore, further stabilization of the monomers may be beneficial (i.e. avoidance of the dimerization or in certain instances possible multimerizations) and may be done by choosing suitable linkers linking the ends of the polypeptides and/or cysteines at or close to the CDR3 and/or FR4 region that prevent the single variable domain from dimerization. E.g. a covalent stabilization of the CDR3 and/or FR4 may be possible by introducing 2 cysteines close to or/and within the CDR3 and/or FR4 region at spatially opposite positions to force formation of a disulphide bridge as has e.g. been done with cystatin that was stabilized against three-dimensional domain swapping by engineered disulfide bonds (Wahlbom et al., J. of Biological Chemistry Vol. 282, No. 25, pp. 18318-18326, Jun. 22, 2007). Furthermore, it may be advantageous to introduce a flexible peptide that is then engineered to have one cysteine that than forms a disulfide bond to e.g. a cysteine before the CDR3 region. In such case, the polypeptides of the invention need to be present first under reducing conditions, to allow the monomers to form after which oxidation can lead to the cysteine pairings, locking the monomers into a fixed, stabilized state.

Furthermore, further stabilization of the monomers may be beneficial (i.e. avoidance of the dimerization or in certain instances possible multimerizations) and may be done by replacing a destabilizing amino acid residue or residues (e.g. identified by screening of mutants, e.g. by affinity maturation methods—see e.g. WO2009/004065) by a stabilizing amino acid residue or residues in the vicinity of CDR3 and/or FR4.

In another aspect of the invention, further stabilization of the monomers can be achieved (i.e. avoidance of the dimerization or in certain instances possible multimerizations) by suitable formulation. In particular, the present invention provides a method for suppressing the dimerization and multimerization of (human serum) albumin-binding Nanobodies® (e.g. polypeptide B) and other polypeptides comprising Nanobodies® by providing mannitol or other polyols to a liquid formulation. Mannitol is generally used for maintaining the stability and isotonicity of liquid protein formulations. It is also a common bulking agent for lyophilization of the formulation. Surprisingly, the present invention discovered that mannitol can specifically inhibit the formation of dimers observed during storage (at elevated temperature) of several albumin-binding Nanobodies®. As a result, mannitol-containing formulations increase protein stability and sustain biological activity, thereby prolonging the shelf-life of the drug product. The stabilizing effect of mannitol is supported by data that demonstrate higher Tm. (melting temperature) values in protein formulations with increasing mannitol concentrations.

This invention will also cover the use of other polyols, non-reducing sugars, NaCl or amino acids.

The dimers formed by e.g. the serum albumin-binding Nanobody® "polypeptide B" of the invention (SEQ ID NO: 2) was shown to be completely inactive for binding to HSA (Biacore analysis), suggesting that the albumin binding site in the dimer interface is blocked by dimer formation. The addition of mannitol to the liquid formulation as proposed by this invention will therefore not only suppress the dimerization process but, importantly, will also preserve the HSA-binding activity of Nanobody® and slow down the inactivation. In general, the mannitol containing formulations according to the inventions prolong the shelf-life of the formulated protein drug product. The invention is believed to be applicable to any albumin-binding Nanobody® and may be applicable to all Nanobodies® that have a tendency to form dimers in general. Thus, the mannitol formulations of the invention are indicated for the formulation of any Nanobody®, as process intermediate, drug substance or drug product. This invention may be used in a wide variety of liquid formulations which may consist of any buffering agent, a biologically effective amount of protein, a concentration of mannitol that is no greater than approximately 0.6M and other excipients including polyols, non-reducing sugars, NaCl or amino acids. The liquid formulations may be stored directly for later use or may be prepared in a dried form, e.g. by lyophilization. Mannitol may be used in any formulation to inhibit the formation of high molecular weight species such as the observed dimers during storage, freezing, thawing and reconstitution after lyophilization.

Thus, the present invention also relates to a formulation that comprises a polypeptide comprising one or more single variable domains, said formulation being formulated for administration to a human subject, and said formulation further comprising an excipient at a concentration of 1% to 20% (w:v).

Preferred excipients include polyols and/or sugars. The polyol and/or sugar may be a monosaccharide such as glucose or mannose, or a polysaccharide including disaccharides such as (without being limiting) sucrose and lactose, as well as sugar derivatives including sugar alcohols and sugar acids. Polyols and sugar alcohols include (without being limiting) mannitol, xylitol, erythritol, threitol, sorbitol and glycerol. A non-limiting example of a sugar acid is L-gluconate. Other exemplary sugars include (without being limiting) trehalose, glycine, maltose, raffinose, etc. The concentration of the excipient may range from about 1% to 20% (w:v), preferably from about 2.5% to 10% (w:v), more preferably from about 5% to 10% (w:v), such as e.g. 5% (w:v), 7.5% (w:v), 8% or 10% (w:v). Throughout the present invention the concentration of the excipient will be given as % (w:v). In a preferred aspect, the formulation comprises sucrose, preferably at a concentration of about 5% to 10% (w:v), such as about 8% w:v).

In one aspect, the formulation of the present invention comprises an aqueous carrier with a pH of 5.5 to 8.0 and a polypeptide comprising one or more single variable domains at a concentration of 1 mg/ml to 200 mg/ml, said formulation being formulated for administration to a human subject, and said formulation further comprising an excipient at a concentration of 1% to 20% (w:v).

In another aspect, the formulation of the present invention comprises an aqueous carrier with a pH of 5.5 to 8.0 and a polypeptide comprising one or more single variable domains at a concentration of 1 mg/ml to 200 mg/ml, said formulation being formulated for administration to a human subject, and said formulation further comprising an excipient at a concentration of 1% to 20% (w:v), wherein said formulation has an inorganic salt concentration of 150 mM or lower.

The stable formulations of the present invention comprise polypeptides of the invention that have a high stability even during transportation and/or long periods of storage and that exhibit little to no aggregation (particularly dimerization and/or oligomerization). In addition to the polypeptide of the invention, the formulations of the present invention comprise at least an aqueous carrier and a buffer. The carrier used in the formulation of the invention should be a liquid carrier. Preferably the carrier is an aqueous carrier such as e.g. distilled water, MilliQ water or Water for Injection (WFI).

The pH of the formulation of the invention generally should not be equal to the isoelectric point of the particular polypeptide and may range from about 5.5 to about 8.0, or from about 6.0 to about 7.5, preferably from about 6.2 to 7.5, from about 6.5 to 7.5, most preferably from about 6.5 to 7.0.

The buffer can be any pharmaceutically acceptable buffer and can (without being limiting) be e.g. selected from the group consisting of histidine pH 6.0-6.5, hepes pH 7.0-8.0, MES pH 6.0, succinate pH 6.0-6.5 and acetate pH 5.5-6.0. The concentration of the buffer present in the formulation of the invention may range from 1 mM to 100 mM, 5 mM to 100 mM, 5 mM to 75 mM, 5 mM to 50 mM, 10 mM to 50 mM, 10 mM to 25 mM, 10 mM to 20 mM. In a specific aspect, the concentration of buffer in the formulations of the invention is 1 mM, 2 mM, 5 mM, 10 mM, 15 mM, 20 mM, 25 mM, 50 mM, 75 mM, or 100 mM. Preferably, the concentration is between 10 and 20 mM, such as 10 mM or 15 mM.

It will be understood by one skilled in the art that the formulation of the invention may be isotonic or slightly hypotonic with human blood, i.e. the formulation of the invention has essentially the same or a slightly lower osmotic pressure as human blood. Such isotonic or slightly hypotonic formulation generally has an osmotic pressure from about 240 mOSm/kg to about 320 mOSm/kg, such as about 240 mOSm/kg or higher, 250 mOSm/kg or higher or 260 mOSm/kg or higher.

Tonicity of a formulation is adjusted by the use of tonicity modifiers. "Tonicity modifiers" are those pharmaceutically acceptable inert substances that can be added to the formulation to provide an isotonicity of the formulation. Preferred tonicity modifier in the formulation of the invention are salts and/or excipients.

The formulation of the invention may additionally comprise a surfactant. A surfactant refers to a surface-active agent comprising a hydrophobic portion and a hydrophilic portion. In a preferred aspect, the surfactant is non-ionic. Certain exemplary non-ionic surfactants include (without being limiting) PEG8000, and polysorbate, including without being limiting, polysorbate 80 (Tween 80) and polysorbate 20 (Tween 20), Triton X-100, polyoxypropylene-polyoxyethylene esters (Pluronic®), and NP-40. In a specific aspect, the surfactant is selected from Tween 20, Tween 80 or a poloxamer. The concentration of the surfactant may range from about 0.001% to 1% (v:v) (preferably from about 0.001% to 0.1% (v:v), or 0.01% to 0.1% (v:v) such as 0.001% (v:v), 0.005% (v:v), 0.01% (v:v), 0.02% (v:v), 0.05% (v:v), 0.08% (v:v), 0.1% (v:v), 0.5% (v:v), or 1% (v:v) of the formulation, preferably 0.01% (v:v)). Throughout the present invention the concentration of the surfactant will be given as % (v:v).

The formulation of the invention may also comprise one or more inorganic salts. In one aspect, the concentration of inorganic salt should not be more than 150 mM. Without being limiting, inorganic salts for use in the formulation of the invention can be selected from NaCl and KCl. Accordingly the formulation of the invention has an inorganic salt concentration of 150 mM or lower, preferably 120 mM or lower, or 100 mM or lower, more preferably 90 mM or lower, 80 mM or lower, 75 mM or lower, such as 50 mM or lower or even 40 mM or lower, 25 mM or lower, 10 mM or lower or 5 mM or lower. In one aspect, the formulation does not contain any inorganic salt.

The polypeptides of the invention present in the formulation of the invention should preferably have a melting temperature of at least 59° C. or more (such as 59.5° C. or more), preferably at least 60° C. or more (such as 60.5° C.

or more), more preferably at least 61° C. or more (such as 61.5° C. or more) or at least 62° C. or more (such as 62.5° C. or more), most preferably at least 63° C. or more (such as 63.5° C. or more) as measured by the thermal shift assay (TSA) and/or differential scanning calorimetry (DSC).

Without being limiting, melting point determination can be done by the fluorescence-based thermal shift assay which is based on the fact that upon thermal unfolding the hydrophobic regions of proteins, usually hidden in the core of the protein fold, become accessible for binding to a hydrophobic fluorescent dye. The fluorescence emission of this dye is quenched in aqueous solution, whereas upon binding to the hydrophobic patches of an unfolded protein a sharp increase in the fluorescence yield of the probe is observed. Temperature induced unfolding is typically a two-state process with a sharp transition between the folded and unfolded state, where the melting temperature (Tm) is defined as the temperature at which half of the protein is in the unfolded state, i.e. the first derivative of the fluorescence signal upon gradual heating of the sample is plotted and the observed peak (or peaks when multiple domains and/or variants of the same domain are present) represents the melting temperature. The thermal shift assay can be performed in a typical real-time PCR instrument where melting curves can be recorded accurately in high-throughput mode with only small quantities of protein required.

During a differential scanning calorimetry experiment the sample is heated at a constant rate in an adiabatic environment ($\Delta T=0$). The energy required to keep the temperature difference between a reference and the sample cell at zero is measured and yields the heat capacity as a function of temperature (Cp(T)). The temperature corresponding to the maximum heat capacity represents the melting temperature ($T_m$). If the temperature dependent unfolding process is reversible other thermodynamic parameters such as the unfolding enthalpy ($\Delta H_{unfolding}$) can be determined.

Increased melting temperatures have been observed for the polypeptides of the invention when present in a formulation that comprises an excipient, preferably a saccharides and/or polyol such as mannitol, trehalose, sorbitol or sucrose. Accordingly, the present invention relates to a formulation comprising a polypeptide comprising one or more single variable domains, said formulation being formulated for administration to a human subject, wherein said formulation further comprises at least an excipient, preferably a saccharide and/or polyol such as mannitol, sorbitol, trehalose or sucrose at a concentration of 1% to 20% (preferably 2.5% to 15%, more preferably 5% to 10%, such as 5%, 7.5%, 8% or 10%); and wherein the melting temperature of the polypeptide of the invention is at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) as measured by the thermal shift assay (TSA) and/or differential scanning calorimetry (DSC).

Accordingly, the present invention relates to a formulation comprising an aqueous carrier at a pH of 6.0 to 8.0 and a polypeptide comprising one or more single variable domains, said formulation being formulated for administration to a human subject, wherein said formulation further comprises at least an excipient, preferably a saccharide and/or polyol such as mannitol, sorbitol, trehalose or sucrose at a concentration of 1% to 20% (preferably 2.5% to 15%, more preferably 5% to 10%, such as 5%, 7.5%, 8% or 10%); wherein the melting temperature of the polypeptide of the invention is at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) as measured by the thermal shift assay (TSA) and/or differential scanning calorimetry (DSC).

Accordingly, the present invention relates to a formulation comprising an aqueous carrier at a pH of 6.0 to 8.0 and a polypeptide comprising one or more single variable domains, said formulation being formulated for administration to a human subject, wherein said formulation further comprises at least an excipient, preferably a saccharide and/or polyol such as mannitol, sorbitol, trehalose or sucrose at a concentration of 1% to 20% (preferably 2.5% to 15%, more preferably 5% to 10%, such as 5%, 7.5%, 8% or 10%), wherein said formulation has an inorganic salt concentration of 150 mM or lower; and wherein the melting temperature of the polypeptide of the invention is at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) as measured by the thermal shift assay (TSA) and/or differential scanning calorimetry (DSC).

The formulation of the present invention exhibit stability when stored at a temperature of 37±5° C. The formulation of the invention may exhibit stability when stored at a temperature of 37±5° C. for at least 2 weeks, 3 weeks, 4 weeks, at least 5 weeks, at least 8 weeks, at least 10 weeks, at least 3 months, at least 6 months, at least 1 year, 1.5 year or even 2 years or more.

As is known to one skilled in the art, the temperatures indicated in this text can be subject to normal variations.

Preferably, those formulations that are stable under one or more of the above stress conditions:
- less than 10% (more preferably less than 5%, even more preferably less than 3%, most preferably less than 1%) of the polypeptide of the invention forms dimers (e.g. as assessed by SE-HPLC) during storage under stress conditions, such as e.g. at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more); and/or
- at least 807© (at least 85%, at least 90%, at least 95%, at least 98%, at least 99%, or at least 99.5%) of the polypeptide of the invention retains its binding activity (e.g. as assessed by ELISA and/or Biacore) to at least one of its (preferably to all of its) targets after storage under stress conditions, such as e.g. at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more) compared to the binding activity prior to the stress condition.

As indicated above, the polypeptides present in the formulation of the invention preferably do not form dimers. The formation of dimers in the sample can e.g. be measured by SE-HPLC. For example, analysis in SE-HPLC of a formulation containing SEQ ID NO: 11 after storage for 10 weeks at a temperature of 37° C., showed the formation of a separate peak eluting at an apparent molecular weight of 44 kDa in comparison with molecular weight markers, while the monomeric polypeptide eluted between the 44 and 17 kDa molecular weight markers. This separate peak at 44 kDa represented a dimeric form of SEQ ID NO: 11. Preferably in the formulation of the invention, less than 10% (more preferably less than 5%, even more preferably less than 3%, most preferably less than 1%) of the polypeptides forms dimers (e.g. as assessed by SE-HPLC) during storage under one or more of the above stress conditions.

Little to no dimer formation of the polypeptides of the invention has been observed in formulations that comprise an excipient, preferably a saccharide and/or polyol such as mannitol, trehalose, sorbitol or sucrose. Accordingly, the present invention relates to a formulation comprising a polypeptide comprising one or more single variable domains, said formulation being formulated for administration to a human subject, wherein said formulation further comprises at least an excipient, preferably a saccharide, a non-reducing sugar and/or polyol such as mannitol, trehalose, sorbitol or sucrose at a concentration of 1% to 20% (preferably 2.5% to 15%, more preferably 5% to 10%, such as 5%, 7.5%, 8% or 10%); wherein less than 10% (preferably less than 8%, more preferably less than 7%, most preferably less than 5%) of the polypeptides forms dimers during one or more of the above stress conditions (such as during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)), the % of dimers as measured by SE-HPLC.

Accordingly, the present invention relates to a formulation comprising an aqueous carrier and a polypeptide comprising one or more single variable domains, said formulation being formulated for administration to a human subject, wherein said formulation further comprises at least an excipient, preferably a saccharide, a non-reducing sugar and/or polyol such as mannitol, trehalose, sorbitol or sucrose at a concentration of 1% to 20% (preferably 2.5% to 15%, more preferably 5% to 10%, such as 5%, 7.5%, 8% or 10%); wherein less than 1.0% (preferably less than 8%, more preferably less than 7%, most preferably less than 5%) of the polypeptides forms dimers during one or more of the above stress conditions (such as during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)), the % of dimers as measured by SE-HPLC.

Accordingly, the present invention relates to a formulation comprising an aqueous carrier and a polypeptide comprising one or more single variable domains, said formulation being formulated for administration to a human subject, wherein said formulation further comprises at least an excipient, preferably a saccharide, a non-reducing sugar and/or polyol such as mannitol, trehalose, sorbitol or sucrose at a concentration of 1% to 20% (preferably 2.5% to 15%, more preferably 5% to 10%, such as 5%, 7.5%, 8% or 10%); wherein said formulation has an inorganic salt concentration of 150 mM or lower; and wherein less than 10% (preferably less than 8%, more preferably less than 7%, most preferably less than 5%) of the polypeptides forms dimers during one or more of the above stress conditions (such as during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)), the % of dimers as measured by SE-HPLC.

Apart from this and/or in addition, the formulation of the present invention shows very little to no loss of potency and/or biological activity of their polypeptides, even during storage under one or more of the above stress conditions.

The potency and/or biological activity of a biological describes the specific ability or capacity of said biological to achieve a defined biological effect. The potency and biological activities of the polypeptides of the invention can be assessed by various assays including any suitable in vitro assay, cell-based assay, in vivo assay and/or animal model known per se, or any combination thereof, depending on the specific disease or disorder involved. Suitable in vitro assays will be clear to the skilled person, and for example include ELISA; FACS binding assay; Biacore; competition binding assay (AlphaScreen®, Perkin Elmer, Mass., USA; FMAT); TRAP assay (osteoclast differentiation assay; Rissanen et al. 2005, J. Bone Miner. Res. 20, Suppl. 1:S256); NF-kappaB reporter gene assay (Mizukami et al. 2002, Mol. Cell. Biol. 22: 992-1000). For example, SEQ ID NO: 11 interacts with RANKL and blocks the interaction of this ligand with RANK, thereby preventing signalization through this receptor. SEQ ID NO's: 12 to 14 interact with IL-6R and block the interaction of this receptor with IL-6. The potency of the polypeptides of the invention for blocking the respective ligand/receptor interaction can be determined, e.g. by ELISA, Biacore, AlphaScreen®.

For example, in one embodiment, Biacore kinetic analysis uses Surface Plasmon Resonance (SPR) technology to monitor macromolecular interactions in real time and is used to determine the binding on and off rates of polypeptides of the formulation of the invention to their target. Biacore kinetic analysis comprises analyzing the binding and dissociation of the target from chips with immobilized polypeptides of the invention on their surface. A typical Biacore kinetic study involves the injection of 250 μL of polypeptide reagent at varying concentration in HBS buffer containing 0.005% Tween 20 over a sensor chip surface, onto which has been immobilized the antigen. In the BIAcore 3000 system, the ligand is immobilized on carboxymethylated dextran over a gold surface, while the second partner (analyte) is captured as it flows over the immobilized ligand surface. The immobilized ligands are remarkably resilient and maintain their biological activity. The bound analytes can be stripped from the immobilized ligand without affecting its activity to allow many cycles of binding and regeneration on the same immobilized surface. Interaction is detected in real time via SPR and at high sensitivity. Because the same affinity may reflect different on-rates and off-rates, this instrument excels over most other affinity measuring methods in that it measures on-rates (ka) and off-rates (kd). Concentration determination experiments are also feasible.

The formulation of the present invention exhibits almost no loss in biological activities of the polypeptide during the prolonged storage under the conditions described above, as assessed by various immunological assays including, for example, enzyme-linked immunosorbent assay (ELISA) and Surface Plasmon Resonance to measure the ability of the polypeptide to specifically bind to an antigen. The polypeptides present in the formulation of the present invention retain, even under the above defined stress conditions (such as storage under certain temperature stress for defined periods) more than 80%, more than 85%, more than 90%, more than 95%, more than 98%, more than 99%, or more than 99.5% of their initial biological activities (e.g., the ability to bind to vWF, RANKL, IL-6R and/or HSA) of the polypeptides prior to the storage. In some embodiments, the polypeptides in the formulation of the invention retain under the above defined stress conditions at least 80%, at least 85%, at least 90%, at least 95%, at least 98%, at least 99%, or at least 99.5% of the biological activity (e.g., the ability to bind to vWF, RANKL, IL-6R and/or HSA) compared to the polypeptides present in a reference formulation prior to the storage.

In one embodiment, the polypeptides of the invention bind HSA. In the formulations of the present invention, at least 80% (preferably at least 85%, at least 90%, at least 95%, at least 98%, at least 99%, or at least 99.5%) of said polypeptides retain their binding activity to HSA under one or more of the above stress conditions (such as storage under certain temperature stress for defined periods) compared to the binding activity prior to the stress condition. Without being limiting, the binding of the polypeptides to HSA can be determined e.g. by ELISA and/or Biacore.

In a preferred aspect, at least 80% (at least 85%, at least 90%, at least 95%, at least 98%, at least 99%, or at least 99.5%) of the polypeptides present in the formulation of the invention retain their binding activity to all of their targets (such as e.g. RANKL and HSA, IL-6R and HSA or IL-23 and HSA) after storage under one or more of the above stress conditions compared to the binding activity prior to storage.

Suitable animal models for determining the potency and/or biological activity of the polypeptides present in the formulations of the invention will be clear to the skilled person and will depend on the intended disease and/or disorder to be prevented and/or treated. Suitable animal models for testing the potency and/or biological activity of the polypeptides of the invention are e.g. described in WO 08/020079, WO 09/068627 and WO 08/142164.

Little to no loss of potency of the polypeptides of the invention has been observed in formulations that comprise an excipient, preferably a saccharide, non-reducing sugar and/or polyol such as mannitol, sorbitol, trehalose or sucrose. Accordingly, the present invention relates to a formulation comprising a polypeptide comprising one or more single variable domains, said formulation being formulated for administration to a human subject, wherein said formulation further comprises at least an excipient, preferably a saccharide, non-reducing sugar and/or polyol such as mannitol, sorbitol, trehalose or sucrose, at a concentration of 1% to 20% (preferably 2.5% to 15%, more preferably 5% to 10%, such as 5%, 7.5%, 8% or 10%); wherein at least 80% (preferably at least 85%, at least 90%, at least 95%, at least 98%, at least 99%, or at least 99.5%) of the polypeptides retain their binding activity to at least one (preferably to all) of their targets under one or more of the above stress conditions (such as during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)) compared to the binding activity prior to the stress conditions, said binding activity as measured by ELISA and/or Biacore.

Accordingly, the present invention relates to a formulation comprising an aqueous carrier and a polypeptide comprising one or more single variable domains, said formulation being formulated for administration to a human subject, wherein said formulation further comprises at least an excipient, preferably a saccharide, non-reducing sugar and/or polyol such as mannitol, sorbitol, trehalose or sucrose, at a concentration of 1% to 20% (preferably 2.5% to 15%, more preferably 5% to 10%, such as 5%, 7.5%, 8% or 10%); wherein at least 80% (preferably at least 85%, at least 90%, at least 95%, at least 98%, at least 99%, or at least 99.5%) of the polypeptides retain their binding activity to at least one (preferably to all) of their targets under one or more of the above stress conditions (such as during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)) compared to the binding activity prior to the stress conditions, said binding activity as measured by ELISA and/or Biacore.

Accordingly, the present invention relates to a formulation comprising an aqueous carrier and a polypeptide comprising one or more single variable domains, said formulation being formulated for administration to a human subject, wherein said formulation further comprises at least an excipient, preferably a saccharide, non-reducing sugar and/or polyol such as mannitol, sorbitol, trehalose or sucrose, at a concentration of 1% to 20% (preferably 2.5% to 15%, more preferably 5% to 10%, such as 5%, 7.5%, 8% or 10%); wherein said formulation has an inorganic salt concentration of 150 mM or lower; and wherein at least 80% (preferably at least 85%, at least 90%, at least 95%, at least 98%, at least 99%, or at least 99.5%) of the polypeptides retain their binding activity to at least one (preferably to all) of their targets under one or more of the above stress conditions (such as during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more)) compared to the binding activity prior to the stress conditions, said binding activity as measured by ELISA and/or Biacore.

Accordingly, in the stable formulations of the present invention preferably:

the polypeptide of the invention has a melting temperature of at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) (e.g. as assessed by TSA or DSC);

less than 10% (more preferably less than 5%, even more preferably less than 3%, most preferably less than 1%) of the polypeptide of the invention forms dimers (e.g. as assessed by SE-HPLC) during storage under one or more stress conditions, such as e.g. at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more); and/or at least 80% (at least 85%, at least 90%, at least 95%, at least 98%, at least 99%, or at least 99.5%) of the polypeptide of the invention retains its binding activity (e.g. as assessed by ELISA and/or Biacore) to at least one (preferably to all) of its targets after storage under one or more stress conditions, such as e.g. at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more) compared to the binding activity prior to the stress condition.

General methods for producing the single variable domains and/or polypeptides present in the formulation of the invention are known to the skilled person and/or have been described in the art. The single variable domains and/or polypeptides can be produced in any host known to the skilled person. For example but without being limiting, the single variable domains and/or polypeptides can be produced in prokaryotic hosts among which *E. coli* or eukaryotic hosts, for example eukaryotic host selected from insect cells, mammalian cells, and lower eukaryotic hosts comprising yeasts such as *Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis,* preferably *Pichia pastoris*. Production of Nanobodies in prokaryotes and lower eukaryotic hosts such as *Pichia pastoris* has e.g. been described in WO 94/04678, WO 94/25591 and WO 08/142164. The contents of these applications are explicitly referred to in the connection with general culturing techniques and methods, including suitable media and conditions. The contents of these documents are incorporated by reference. The skilled person can also devise suitable genetic constructs for expression of the polypeptides of the invention in different hosts on the basis of the present application and common general knowledge. The present invention also relates to conditions and genetic constructs described in the art, for example the general culturing methods, plasmids, promoters and leader sequences described in WO 94/25591, WO 08/020079, Gasser et al. 2006 (Biotechnol. Bioeng. 94: 535); Gasser et al. 2007 (Appl. Environ. Microbiol. 73: 6499); or Damasceno et al. 2007 (Microbiol. Biotechnol. 74: 381).

More particularly, the method for the expression and/or production of a polypeptide comprising one or more single variable domains at least comprising the steps of:
a) cultivating a host or host cell (as defined herein) under conditions that are such that said host or host cell will multiply;
b) maintaining said host or host cell under conditions that are such that said host or host cell expresses and/or produces the polypeptide;
c) isolating and/or purifying the secreted polypeptide from the medium.

To produce/obtain expression of the polypeptide, the transformed host cell or transformed host organism may generally be kept, maintained and/or cultured under conditions such that the (desired) polypeptide is expressed/produced. Suitable conditions will be clear to the skilled person and will usually depend upon the host cell/host organism used, as well as on the regulatory elements that control the expression of the (relevant) nucleotide sequence. Again, reference is made to the handbooks and patent applications mentioned above.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

The polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the polypeptide of the invention) and/or preparative immunological techniques (i.e. using antibodies against the polypeptide to be isolated).

In the present invention, the host can be removed from the culture medium by routine means. For example, the host can be removed by centrifugation or filtration. The solution obtained by removal of the host from the culture medium is also referred to as culture supernatant, or clarified culture supernatant. The polypeptides of the invention can be purified from the culture supernatant by standard methods. Standard methods include, but are not limited to chromatographic methods, including size exclusion chromatography, hydrophobic interaction chromatography, ion exchange chromatography, and affinity chromatography. These methods can be performed alone or in combination with other purification methods, e.g. precipitation or gel electrophoresis. The skilled person can devise suitable combinations of purification methods for the polypeptides of the invention on the basis of common general knowledge. For specific examples the art cited herein is referred to.

In one exemplary embodiment, the polypeptides of the invention can be purified from culture supernatant by a combination of affinity chromatography on Protein A, ion exchange chromatography and size exclusion chromatography. Reference to any "step of purification", includes, but is not limited to these particular methods.

More specifically, the polypeptides of the invention can be purified from culture supernatant using a process wherein the clarified supernatant (obtained by centrifugation) is captured on any combination of columns selected from (without being limiting) affinity chromatography resin such as Protein A resin, Cation Exchange Chromatography (CIEC) or an Anion Exchange Chromatography (AIEC) using for example Poros 50HS (POROS), SOURCE 30S or SOURCE 15S (GE Healthcare), SP Sepharose (GE Healthcare), Capto S (GE Healthcare), Capto MMC (GE Healthcare) or Poros 50HQ (POROS), SOURCE 30Q or SOURCE 15Q (GE Healthcare), Q Sepharose (GE Healthcare), Capto Q and DEAE Sepharose (GE Healthcare), Size exclusion chromatography (SE-HPLC) using for example Superdex 75 or Superdex 200 (GE Healthcare), hydrophobic interaction chromatography (HIC) using for example octyl, butyl sepharose or equivalents, optionally also including a tangential flow filtration (TFF) step. Any combination of columns can be used for the purification of the polypeptides of the invention, such as e.g. Protein A resin followed by Cation Exchange Chromatography or two Cation Exchange Chromatography steps.

The present invention also provides methods for preparing the stable formulations of the invention comprising the polypeptides of the invention. More particularly, the present invention provides methods for preparing stable formulations of such polypeptides, said methods comprising concentrating a fraction containing the purified polypeptide to the final polypeptide concentration using e.g. a semipermeable membrane with an appropriate molecular weight (MW) cutoff (e.g. a 5 kD cutoff for single variable domains; a 10 kD cutoff for bivalent polypeptides comprising two single variable domains; or a 15 kD cutoff for trivalent polypeptides comprising three single variable domains) and diafiltering and/or ultrafiltering to buffer exchange and further concentrate the polypeptide fraction into the formulation buffer using the same membrane. As extensively described above, the formulation buffer of the present invention may further comprise an excipient at a concentration of 1% to 20%.

The pH of the formulation may range from about 5.5 to about 8.0, or may range from about 6.0 to about 7.5, preferably from about 6.2 to 7.5, from about 6.2 to 7.0, most preferably from about 6.5 to 7.0.

Surfactant (e.g. Tween 20, Tween 80 or poloxamer) may be added after the final diafiltration/ultrafiltration step at a concentration in the range of about 0% to 1%, preferably 0.001% to 0.1%, or 0.01% to 0.17© such as 0.001%, 0.005%, 0.01%, 0.02%, 0.05%, 0.08%, 0.1%, 0.5%, or 1% of the formulation, preferably 0.01% or 0.005%.

The formulation of the present invention may be sterilized by various sterilization methods, including sterile filtration, radiation, etc. In a specific embodiment, the polypeptide formulation is filter-sterilized with a presterilized 0.2 micron filter.

Preferably, the formulation of the present invention is supplied in a hermetically sealed container. Liquid formulations may comprise a quantity between 1 mL and 20 mL, preferably about 1 mL, 2 mL, 3 mL, 4 mL, 5 mL, 6 mL, 7 mL, 8 mL, 9 mL, 10 mL, 15 mL, or 20 mL.

The formulation of the present invention can be prepared as unit dosage forms by preparing a vial containing an aliquot of the formulation for a one time use. For example, a unit dosage of liquid formulation per vial may contain 1 mL, 2 mL, 3 mL, 4 mL, 5 mL, 6 mL, 7 mL, 8 mL, 9 mL, 10 mL, 15 mL, or 20 mL of the formulation. The pharmaceutical unit dosage forms can be made suitable for any form of delivery of the polypeptide of the invention including (without being limiting) parenteral delivery, topical delivery, pulmonary delivery, intranasal delivery, vaginal delivery, enteral delivery, rectal delivery, oral delivery and/or sublingual delivery. In one aspect, the present invention relates to a pharmaceutical unit dosage form suitable for parenteral (such as e.g. intravenous, intraarterial, intramuscular, intracerebral, intraosseous, intradermal, intrathecal, intraperitoneal, subcutaneous, etc) administration to a subject, comprising a formulation of the invention in a suitable container. In another preferred aspect, the subject is a human. In another specific embodiment, the formulations of the present invention are formulated into single dose vials as a sterile liquid that contains 10 mg/mL of one of SEQ ID NO's: 1 to 6, 10 mM histidine buffer at pH 6.0, 10% sucrose and 0.0005% Tween 80.

The amount of a formulation of the present invention which will be effective in the prevention, treatment and/or management of a certain disease or disorder can be determined by standard clinical techniques well-known in the art or described herein. The precise dose to be employed in the formulation will also depend on the route of administration, and should be decided according to the judgment of the practitioner and each patient's circumstances. Effective doses may be extrapolated from dose-response curves derived from in vitro or animal model test systems. For formulations of the polypeptide, encompassed by the invention, the dosage administered to a patient may further be calculated using the patient's weight in kilograms (kg) multiplied by the dose to be administered in mg/kg.

The required volume (in nit) to be given is then determined by taking the mg dose required divided by the concentration of the polypeptide formulation. The final calculated required volume will be obtained by pooling the contents of as many vials as are necessary into syringe(s) to administer the polypeptide formulation of the invention.

The present invention also encompasses a finished packaged and labelled pharmaceutical product. This article of manufacture or kit includes the appropriate unit dosage form in an appropriate vessel or container such as a glass vial or other container that is hermetically sealed. In one embodiment, the unit dosage form is suitable for intravenous, intramuscular, intranasal, oral, topical or subcutaneous delivery. Thus, the invention encompasses formulations, preferably sterile, suitable for each delivery route. In the case of dosage forms suitable for parenteral administration (such as e.g. subcutaneous administration) the active ingredient, e.g., polypeptide of the invention, is sterile and suitable for administration as a particulate free solution.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures, and other monitoring information.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises the formulation containing the polypeptide. The packaging material includes instruction means which indicate that said polypeptide can be used to prevent, treat and/or manage one or more symptoms associated with the disease or disorder by administering specific doses and using specific dosing regimens as described herein.

The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises a formulation containing the polypeptide of interest, and wherein said packaging material includes instruction means which indicate that said agents can be used to prevent, treat and/or manage the disease or disorder by administering specific doses and using specific dosing regimens as described herein.

The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises a formulation containing the polypeptide, and wherein said packaging material includes instruction means which indicate that said agents can be used to prevent, treat and/or manage one or more symptoms associated with the disease or disorder by administering specific doses and using specific dosing regimens as described herein.

The formulations, containers, pharmaceutical unit dosages and kits of the present invention may be administered to a subject to prevent, treat and/or manage a specific disease and/or disorder. In a specific aspect, the formulations, containers, pharmaceutical unit dosages and kits of the present invention are administered to a subject to prevent, treat and/or manage a disease and/or disorder associated with or characterized by aberrant expression and/or activity of a certain target or one or more symptoms thereof. In another specific aspect, the formulations, containers, pharmaceutical unit dosages and kits of the present invention are administered to a subject to prevent, treat and/or manage diseases and/or disorders associated with aberrant expression and/or activity of RANKL, diseases and/or disorders associated with overexpression of IL-6, or vascular diseases and/or disorders or one or more symptoms thereof.

Diseases and disorders associated with aberrant expression and/or activity of RANKL are for example bone diseases and disorders, and include (without being limiting) the following diseases and disorders: Osteoporosis (McClung 2006, Current Osteoporosis Reports 4: 28-33), including, but not limited to, primary osteoporosis, endocrine osteoporosis (including, but not limited to, hyperthyroidism, hyperparathyroidism (Anandarajah and Schwarz 2006, J. Cell Biochem. 97: 226-232), Cushing's syndrome, and acromegaly), hereditary and congenital forms of osteoporosis (including, but not limited to, osteogenesis imperfecta, homocystinuria, Menkes' syndrome, Riley-Day syndrome), osteoporosis due to immobilization of extremities, glucocorticoid-induced osteoporosis (Locklin et al. 2001, Bone 28 (Suppl.): S80; McClung 2006, Current Osteoporosis Reports 4: 28-33; Anandarajah and Schwarz 2006, J. Cell Biochem. 97: 226-232) and post-menopausal osteoporosis (McClung 2006, Current Osteoporosis Reports 4: 28-33); (Juvenile or Familial) Paget's disease (Gundy et al. 2002, Hum. Mol. Genet. 11: 2119-2127; Whyte et al. 2002, J. Bone Miner. Res. 17: 26-29; Whyte et al. 2002, N. Engl. J. Med. 347: 175-1.84; Johnson-Pais et al. 2003, J. Bone Miner Res. 18: 376-380; Anandarajah and Schwarz 2006, J. Cell Biochem. 97: 226-232; Anandarajah and Schwarz 2006, J. Cell Biochem. 97: 226-232); Osteomyelitis, i.e., an infectious lesion in bone, leading to bone loss; Hypercalcemia (Anandarajah and Schwarz 2006, J. Cell Biochem. 97: 226-232), including, but not limited to, hypercalcemia resulting from solid tumors (including, but not limited to, breast, lung and kidney) and hematologic malignancies (including, but not limited to, multiple myeloma (Sordillo and Pearse 2003, Cancer 97 (3 Suppl): 802-812; Vanderkerken et al. 2003, Cancer Res. 63: 287-289), lymphoma and leukemia), idiopathic hypercalcemia, and hypercalcemia associated with hyperthyroidism and renal function disorders; Bone loss, including but not limited to, osteopenia following surgery, osteopenia induced by steroid administration, osteopenia associated with disorders of the small and large intestine, and osteopenia associated with chronic hepatic and renal diseases; Osteonecrosis, i.e., bone cell death, including, but not limited to, osteonecrosis associated with traumatic injury, osteonecrosis associated with Gaucher's disease, osteonecrosis associated with sickle cell anemia, osteonecrosis associated with systemic lupus erythematosus, osteonecrosis associated with rheumatoid arthritis, osteonecrosis associated with periodontal disease, osteonecrosis associated with osteolytic metastasis, and osteonecrosis associated with other condition; Bone loss associated with arthritic disorders such as psoriatic arthritis, rheumatoid arthritis, loss of cartilage and joint erosion associated with rheumatoid arthritis (Bezerra et al. 2005, Brazilian Journal of Medical and Biological Research 38: 161-170; Anandarajah and Schwarz 2006, J. Cell Biochem. 97: 226-232); Arthritis (Bezerra et al. 2005, Brazilian Journal of Medical and Biological Research 38: 161-170), including inflammatory arthritis (McClung 2006, Current Osteoporosis Reports 4: 28-33), Collagen-induced arthritis (Bezerra et al. 2005, Brazilian Journal of Medical and Biological Research 38: 161-170); Periprosthetic osteolysis (McClung 2006, Current Osteoporosis Reports 4: 28-33; Anandarajah and Schwarz 2006, J. Cell Biochem. 97: 226-232); Cancer-related bone disease (McClung 2006, Current Osteoporosis Reports 4: 28-33); Bone loss associated with aromatase inhibitor therapy (Lewiecki. 2006, Expert Opin. Bial. Ther. 6: 1041-1050); Bone loss associated with androgen deprivation therapy (Lewiecki 2006, Expert Opin. Biol. Ther. 6: 1041-1050); Bone loss associated bone metastasis; Bone loss associated with diseases having immune system involvement, such as adult and childhood leukaemias, cancer metastasis, autoimmunity, and various viral infections (Holstead Jones et al. 2002, Ann. Rheum. Dis. 61 (Suppl II): ii32-ii39) Osteopenic disorders such as adult and childhood leukaemia (Oliveri et al. 1999, Henry Ford Hosp. Med. 39: 45-48), chronic infections such as hepatitis C or HTV (Stellon et al. 1985, Gastroenterology 89: 1078-1083), autoimmune disorders such as diabetes mellitus (Piepkorn et al. 1997, Horm. Metab. Res. 29: 584-91), and lupus erythematosus (Seitz et al. 1985, Ann. Rheum Dis. 44: 438-445), allergic diseases such as asthma (Ebeling et al. 1998, J. Bone Min. Res. 13: 1283-1289), lytic bone metastases in multiple cancers such as breast cancer (Coleman 1998, Curr. Opin. Oncol. 10 (Suppl I): 7-13); Prostate cancer; Myeloma bone disease Anandarajah and Schwarz 2006, J. Cell Biochem. 97: 226-232); Periodontal infections ((Anandarajah and Schwarz 2006, J. Cell Biochem. 97: 226-232); Expansile skeletal hyperphosphatasia (Anandarajah and Schwarz 2006, J. Cell Biochem. 97: 226-232); Bone metastases (Lewiecki 2006, Expert Opin. Biol. Ther. 6: 1041-1050; Anandarajah and Schwarz 2006, J. Cell Biochem. 97: 226-232), Also encompassed within the scope of the present invention is the prevention and/or treatment with the formulations, containers, pharmaceutical unit dosages and kits of the invention of other diseases and disorders associated with an imbalance in the RANKL/RANK/OPG pathway. Such diseases and disorders include but are not limited to osteoporosis, inflammatory conditions, autoimmune conditions, asthma, rheumatoid arthritis, multiple sclerosis, Multiple myeloma (Sordillo and Pearse 2003, Cancer 97 (3 Suppl): 802-812; Vanderkerken et al. 2003, Cancer Res. 63: 287-289); Vascular diseases (Anandarajah and Schwarz 2006, J. Cell Biochem. 97: 226-232) and Cardiovascular disease (Lewiecki 2006, Expert Opin. Biol. Ther. 6: 1041-1050).

Also encompassed within the scope of the present invention is the prevention and/or treatment with the formulations, containers, pharmaceutical unit dosages and kits of the invention of diseases and disorders associated with osteopetrosis such as osteopetrosis tarda, osteopetrosis congenita and marble hone disease.

Disease and disorders caused by excessive IL-6 production include sepsis (Starnes et al., 1999) and various forms of cancer such as multiple myeloma disease (MM), renal cell carcinoma (RCC), plasma cell leukaemia (Klein et al., 1991), lymphoma, B-lymphoproliferative disorder (BLPD) and prostate cancer. Non-limiting examples of other diseases caused by excessive IL-6 production or signalling include bone resorption (osteoporosis) (Roodman et al., 1992; Jilka et al., 1992), cachexia (Strassman et al., 1992), psoriasis, mesangial proliferative glomerulonephritis, Kaposi's sarcoma, AIDS-related lymphoma (Emilie et al., 1994), inflammatory diseases and disorder such as rheumatoid arthritis, systemic onset juvenile idiopathic arthritis, hypergammaglobulinemia (Grau et al., 1990); Crohn's disease, ulcerative colitis, systemic lupus erythematosus (SLE), multiple sclerosis, Castleman's disease, IgM gammopathy, cardiac myxoma, asthma (in particular allergic asthma) and autoimmune insulin-dependent diabetes mellitus (Campbell et al., 1991).

Vascular diseases and/or disorders include acute coronary syndrome (ACS), myocardial infarction, thrombotic thrombocytopenic purpura (TTP) or Moschcowitz syndrome, vascular surgery and stroke.

The formulations, containers, pharmaceutical unit dosages and kits of the present invention may also be advantageously utilized in combination with one or more other therapies (e.g., one or more other prophylactic or therapeutic agents), preferably therapies useful in the prevention, treatment and/or management of the (same or another) disease or disorder. When one or more other therapies (e.g., prophylactic or therapeutic agents) are used, they can be administered separately, in any appropriate form and by any suitable route. Therapeutic or prophylactic agents include, but are not limited to, small molecules, synthetic drugs, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, other single variable domains, synthetic or natural inorganic molecules, mimetic agents, and synthetic or natural organic molecules. Any therapy (e.g., prophylactic or therapeutic agents) which is known to be useful, or which has been used or is currently being used for the prevention, treatment and/or management of one or more symptoms associated with a specific disease or disorder, can be used in combination with the formulations of the present invention in accordance with the invention described herein.

A formulation of the invention may be administered to a mammal, preferably a human, concurrently with one or more other therapies (e.g., one or more other prophylactic or therapeutic agents). The term "concurrently" is not limited to the administration of prophylactic or therapeutic agents/therapies at exactly the same time, but rather it is meant that the formulation of the invention and the other agent/therapy are administered to a mammal in a sequence and within a time interval such that the polypeptide contained in the formulation can act together with the other agent/therapy to provide an increased benefit than if they were administered otherwise. For example, the formulation of the invention and the one or more other prophylactic or therapeutic agents may be administered at the same time or sequentially in any order at different points in time; however, if not administered at the same time, they should be administered sufficiently close in time so as to provide the desired therapeutic or prophylactic effect.

When used in combination with other therapies (e.g., prophylactic and/or therapeutic agents), the formulations of the invention and the other therapy can act additively or synergistically. The invention contemplates administration of a formulation of the invention in combination with other therapies (e.g., prophylactic or therapeutic agents) by the same or different routes of administration, e.g., oral and parenteral.

Various delivery systems are known and can be used to administer the formulation of the present invention. Methods of administering formulations of the present invention include, but are not limited to, parenteral administration (e.g., intradermal, intramuscular, intraperitoneal, intravenous and, preferably subcutaneous), epidural administration, topical administration, and mucosal administration (e.g., intranasal and oral routes). In a specific embodiment, liquid formulations of the present invention are administered parenteral.

A particular advantage of the NFDs described in this invention is the ability to assemble functionally or partly functionally during e.g. the manufacturing process (e.g. purification step etc) in a controllable manner. A dimerization principle is used which allows the formation of homodimers. Examples described herein include NFDs-Mo. NFDs-Di, and NFDs-Tri. In these cases, the monomeric building blocks are expressed in a bacterial system and then bound in high concentration to a separation chromatographic device, e.g. Protein A or IMAC, and eluted swiftly to retain the desired dimeric complexes, i.e. the NFDs, in substantial yield. Under these conditions, the homodimeric proteins form by themselves and can directly be isolated in the dimeric form by said separation step and/or further isolated by size exclusion chromatography.

The present invention is further illustrated by the following preferred aspects and examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

Preferred Aspects:

A-1. A stable NFD.

A-2. A stable NFD in solution.

A-3. A stable NFD obtainable by a process comprising the step of concentrating a polypeptide comprising at least one single variable domain and/or by a process comprising the step of storage of a polypeptide comprising at least one single variable domain at elevated temperature, e.g. at a temperature close to the melting temperature or e.g. at 37° C. over a prolonged time period, e.g. such as 1 to 4 weeks, e.g. 4 weeks.

A-4. A stable NFD obtainable by a process comprising the step of concentrating a polypeptide comprising and/or consisting of one or more single variable domain(s) and one or more linkers.

A-5. A stable NFD according to any of aspects A-3 or A-4, wherein the step of concentrating is done by affinity- and/or ion exchange chromatography.

A-6. A stable NFD according to any of the aspects A-3 to A-5, wherein the step of concentrating is done on a Protein A column, and wherein high amounts of polypeptide are loaded on the column, e.g. 2 to 5 mg per ml resin Protein A.

A-7. A stable NFD according to any of the aspects 5 or 6, wherein the polypeptide is eluted by a steep pH gradient, e.g. a one step pH change of 2.

A-8. A stable NFD according to the previous aspects, wherein the NFD is stable over a period of up to 2 years at −20 degrees Celcius.

A-9. A stable NFD according to the aspects above, wherein the NFD is stable over a period of up to 2 weeks at 4 degrees Celcius.

A-10. A stable NFD according to the previous aspects, wherein the NFD is stable over a period of up to 15 minutes at 50 degrees Celcius.

A-11. A stable NFD according to the previous aspects, wherein the NFD is stable at acidic pH.

A-12. A stable NFD according to the previous aspects, wherein the NFD is stable at acidic pH over a prolonged period of time, e.g. a time up to 1 day, more preferably 1 week, more preferably 2 weeks, even more preferably 3 weeks, most preferred 4 weeks.

A-13. A stable NFD according to the previous aspects, wherein the NFD is stable at basic pH over a prolonged period of time, e.g. a time up to 1 clay, more preferably 1 week, more preferably 2 weeks, even more preferably 3 weeks, most preferred 4 weeks.

A-14. A stable NFD according to the previous aspects, wherein the NFD is stable between pH 3 and pH 8.

A-15. A stable NFD according to the previous aspects, wherein the NFD is stable between pH 2.5 and pH 8.

A-16. A stable NFD according to the previous aspects, wherein the NFD is stable between pH 3 and pH 8 for 4 weeks at 4 degrees Celcius.

A-17. A stable NFD according to the previous aspects, wherein the NFD is stable when mixing with organic solvents.

A-18. A stable NFD according to the previous aspects, wherein the NFD is stable when mixing with an alcohol, e.g. isopropanol.

A-19. A stable NFD according to the previous aspects, wherein the NFD is stable when mixing with 30% v/v of an alcohol, e.g. isopropanol.

A-20. A stable NFD according to the previous aspects, wherein the dissociation constant of the binding of the NFD to its target molecule is about the same as the dissociation constant of the binding of its corresponding monomeric building block to said target molecule.

A-21. A stable NFD according to the previous aspects, wherein there is no specific binding to its target molecule.

A-22. A stable NFD according to the previous aspects, wherein the dissociation constant of the binding of the NFD to its target molecule is 30% or less, preferably 20% or less, more preferably 10% or less, of the dissociation constant of the binding of its corresponding monomeric building block to said target molecule.

A-23. A stable NFD according to the previous aspects, wherein the dissociation constant of the binding of the NFD to its target molecule is 100 nM or less, preferably 10 nM or less, more preferably 1 nM or less.

A-24. A stable NFD according to the previous aspects, wherein the koff value for the binding of the NFD to its target molecule is about the same as the koff value for the binding of its corresponding monomeric building block.

A-25. A stable NFD according to the previous aspects, wherein the koff value for the binding of the NFD to its target molecule is not more than 90%, more preferably not more than 50%, even more preferably not more than 40%, even more preferably not more than 30%, even more preferably not more than 20%, most preferably not more than 10% higher than the koff value for the binding of its corresponding monomeric building block.

A-26. A stable NFD according to the previous aspects, wherein the koff value for the binding of the NFD to its target molecule is not more than 50% higher than the koff value for the binding of its corresponding monomeric building block.

A-27. A stable NFD according to the previous aspects, wherein the koff value for the binding of the NFD to its target molecule is not more than 10% higher than the value for the binding of its corresponding monomeric building block.

A-28. A stable NFD according to the previous aspects, wherein the single variable domain is a Nanobody® such as a VHH, a humanized VHH, an affinity-matured, stabilized, sequence optimized or otherwise altered VHH or a construct thereof.

A-29. A stable NFD according to the previous aspects, wherein the single variable domain is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, SEQ ID NO: 13 and SEQ ID NO: 14, preferably SEQ ID NO: 2.

A-30. A stable NFD according to the previous aspects, wherein the single variable domain is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, SEQ ID NO: 13 and SEQ ID NO: 14, preferably SEQ ID NO: 2 and of a functional sequence that is at least 70%, more preferably at least 80%, even more preferably at least 90%, most preferably at least 95% identical to any of SEQ ID NO: 1, SEQ ID NO: 2, SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, SEQ ID NO: 13 and SEQ ID NO: 14, preferably SEQ ID NO: 2.

A-31. A stable NFD according to the previous aspects, wherein the single variable domain is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, SEQ ID NO: 13 and SEQ ID NO: 14, preferably SEQ ID NO: 2 and of a functional sequence that is at least 70%, more preferably at least 80%, even more preferably at least 90%, most preferably at least 95% identical to any of SEQ ID NO: 1, SEQ ID NO: 2, SEQ II) NO: 3, SEQ ID NO: 4, SEQ NO: 5, SEQ ID NO: 6, SEQ ID NO: 9, SEQ ID NO: 10, SEQ ID NO: 11, SEQ ID NO: 12, SEQ ID NO: 13 and SEQ ID NO: 14, preferably SEQ ID NO: 2; and wherein said polypeptide specifically binds to its target molecule(s), more preferably has a dissociation constant to at least one of its target molecules (if bi- or multispecific), of 100 nM or less, even more preferably of 10 nM or less, most preferably of 1 nM or less.

A-32. A NFD of any of the previous aspects (e.g. as described herein) wherein the single variable domain is not as described in Spinelli et al, FEBS Letters 564 (2004) 35-40.

A-33. A functional fragment of a NFD as described in any of aspects A-1 to A-32.

A-34. A polypeptide comprising at least one single variable domain, wherein said at least one single variable domains can form a NFD as e.g. described in any of aspects A-1 to A-32.

B-1. A preparation comprising a NFD as described in any of aspects A-1 to A-32, a functional fragment of aspect A-33, or a polypeptide of aspect A-34.

B-2. A preparation comprising a NFD as described in any of aspects A-1 to A-32, a functional fragment of aspect A-33 or a polypeptide of aspect A-34, wherein the ratio of NFD and its corresponding monomeric building block is about 1 part NFD/1 part corresponding monomeric building block to about 1 part NFD/2 parts corresponding monomeric building block.

B-3. A preparation comprising a NFD as described in any of aspects A-1 to A-32, a functional fragment of aspect A-33 or a polypeptide of aspect A-34, wherein the ratio of NFD and its corresponding monomeric building block is about 1 part NFD/1 part corresponding monomeric building block to about 2 parts NFD/1 part corresponding monomeric building block.

B-4. A preparation comprising a NFD as described in any of claims A-1 to A-32, a functional fragment of aspect A-33 or a polypeptide of aspect A-34, wherein the ratio of NFD and its corresponding monomeric building block is 25% NFD/75% monomeric building block.

B-5. A preparation comprising a NFD as described in aspects A-1 to A-32, a functional fragment of aspect A-33 or a polypeptide of aspect A-34, wherein the ratio of NFD and its corresponding monomeric building block is 75% NFD/25% monomeric building block.

C-1. A process of making a NFD according to any of aspects A-1 to A-32, a functional fragment of aspect A-33 or a polypeptide of aspect A-34, comprising a process step that has a condition that favors hydrophobic interactions.

C-2. A process of making a NFD according to aspect C-1, wherein said process step is a purification step.

C-3. A process of making a NFD according to aspect C-1, wherein within said process step, the condition is such that it promotes partial protein unfolding.

C-4. A process of making a NFD according to aspect C-3, wherein said process step is a purification step.

C-5. A process of making a NFD according to any of aspects A-1 to A-32, a functional fragment of aspect A-33 or a polypeptide of aspect A-34, comprising the step of up-concentrating the monomeric building blocks of said. NFD, e.g. by binding the polypeptides comprising one or more single variable domain(s) on an affinity chromatography column, e.g. Protein A or IMAC.

C-6. A process of making a NFD according to any of aspects A-1 to A-32, a functional fragment of aspect A-33 or a polypeptide of aspect A-34, comprising the step of binding polypeptides comprising one or more single variable domain(s) on a affinity chromatography column, e.g. Protein A or IMAC, and eluting with a pH step which allows release of said polypeptide.

C-7. A process of making NFD according to any of aspects A-1 to A-32, a functional fragment of aspect A-33 or a polypeptide of aspect A-34, comprising the step of binding polypeptides comprising one or more single variable domain(s) on a affinity chromatography column, e.g. Protein A, and eluting with a pH step which allows release of said polypeptide within 1 column volume.

C-8. A process of making a NFD according to any of aspects A-1 to A-32, a functional fragment of aspect A-33 or a polypeptide of aspect. A-34, comprising the step of ultra-filtration.

C-9. A process according to aspect C-8, wherein the ultra-filtration is done under conditions of low salt.

C-10. A process of making a NFD according to any of aspects A-1 to A-32, a functional fragment of aspect A-33 or a polypeptide of aspect A-34, comprising the process step of storing the appropriate polypeptide comprising one or more single variable domain(s) at elevated temperature over a prolonged time.

C-11. A process of making a NFD according to aspect C-10, wherein said elevated temperature is 37° C. and time is 1, 2, 3, 4, 5, or 6, preferably 4 weeks.

C-12. A process of making a NFD according to aspect C-10 or C-11, wherein said elevated temperature is such that it promotes partial protein unfolding and exposure is over 1, 2, 3, 4, 5, or 6, preferably 4 weeks.

C-13. A process of making a NFD according to aspect C-10 to C-12, wherein said elevated temperature is close to the inciting temperature of the polypeptide and exposure is over 1, 2, 3, 4, 5, or 6, preferably 4 weeks.

C-14. A process of making a NFD according to aspect C-9 to C-13, wherein the CDR3 of said single variable domain is destabilized.

C-15. A process of making a NFD according to any of aspects C-10 to C-14, wherein the single variable domain is a Nanobody®, such as e.g. a VHH, a humanized VHH, an affinity-matured, stabilized, sequence optimized or otherwise altered VHH.

D-1. A process of making monomeric polypeptides comprising one or more single variable domain(s), e.g. Nanobody® such as a VHH, a humanized VHH, an affinity-matured, stabilized, sequence optimized or otherwise altered VHH, wherein each of the steps in the making of said polypeptide does not generate more than 10%, more preferably not more than 5%, even more preferably not more than 4%, even more preferably not more than 3%, even more preferably not more than 2%, even more preferably not more than 1%, most preferred not more than 0.1% w/w corresponding NFD.

D-2. A process according to aspect D-1, wherein each of the steps in said process avoids conditions favoring hydrophobic interactions.

D-3. A process according to any of aspects D-1 or D-2, wherein said conditions favoring hydrophobic interactions is a high concentration of the polypeptides, i.e. a concentration of the polypeptides e.g. more than 10 mg polypeptide per ml resin column material; and thus a process avoiding said interactions is avoiding such conditions in each step of its making.

D-4. A process according to aspect D-3, wherein column loads, e.g. of an affinity column, are carefully evaluated and overload of the column is avoided, i.e. a column load maximum should be determined wherein not more than 10%, more preferably not more than 5%, even more preferably not more than 4%, even more preferably not more than 3%, even more preferably not more than 2%, even more preferably not more than 1%, most preferred not more than 0.1% w/w NFD is generated.

D-5. A process according to any of aspects D1 to D-4 of making monomeric polypeptides comprising one or more single variable domain(s), e.g. Nanobody® such as a VHH, a humanized VHH, an affinity-matured, stabilized, sequence optimized or otherwise altered VHH devoid of NFD or with no more than 50%, more preferably no more than 40%, even more preferably no more than 30%, even more preferably no more than 20%, most preferred no more than 10% NFD, wherein each of the steps in said process avoids conditions favoring hydrophobic interactions, e.g. wherein the process does not consist of a protein A step and/or wherein said process avoids conditions wherein the one or more single variable domain is partially unfolded, e.g. CDR3 is destabilized and/or partially unfolded by e.g. elevated temperature such as a temperature close to the melting temperature of the polypeptide or e.g. 37° C., over a prolonged time, e.g. weeks such as e.g. 4 weeks.

E-1. A pharmaceutical formulation comprising a polypeptide susceptible to dimerization (i.e. the formation of NFDs), e.g. a polypeptide as described in any of aspects A-1 to A-31, e.g. a polypeptide that comprises at least one of SEQ ID NO: 1, SEQ II) NO: 2, SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, SEQ ID NO: 13, SEQ ID NO: 14, e.g. a polypeptide that comprises polypeptide B, and polyol.

E-2. The pharmaceutical formulation according to aspect E-1, wherein the polyol is in a concentration of e.g. not more than 0.6M.

E-3. The pharmaceutical formulation according to any of aspects E-1 or E-2, wherein the polyol is one or more selected from sorbitol, mannitol, xylitol, ribitol, and erythritol.

E-4. The pharmaceutical formulation according to any of aspects E-1 to E-3, wherein the polyol is mannitol, and e.g. in a concentration of not more than 0.6 M mannitol.

E-5. The pharmaceutical formulation according to any of aspects to E-4, wherein the polypeptide comprises a single variable domain that binds serum albumin, preferably human serum albumin.

E-6. The pharmaceutical formulation according to any of aspects E-1 to E-5, wherein the polypeptide comprises polypeptide B.

E-7. The pharmaceutical formulation according to any of aspects E-1 to E-6, additionally comprising a non-reducing sugar such as e.g. sucrose and/or trehalose and optionally NaCl and/or amino acids.

E-8. The pharmaceutical formulation according to any of aspects E-1 to E-7, that is a liquid formulation.

E-9. The pharmaceutical formulation according to any of aspects E-1 to E-8, that is prepared in a dried form, e.g. by lyophilization.

E-10. The pharmaceutical formulation according to any of aspects E-1 to E-9, that is used as an injectable.

E-11. The pharmaceutical formulation according to any of aspects E-1 to E-10, that is used as a subcutaneous formulation.

F-1. A formulation, such as a pharmaceutical formulation, comprising a polypeptide comprising one or more single variable domains, said formulation being formulated for administration to a human subject, further comprising an excipient at a concentration of 1% to 20%.

F-2. A formulation comprising an aqueous carrier having a pH of 5.5 to 8.0 and a polypeptide comprising one or more single variable domains at a concentration of 1 mg/ml to 200 mg/mL, said formulation being formulated for administration to a human subject, and said formulation further comprising an excipient at a concentration of 1% to 20%.

F-3. A formulation comprising an aqueous carrier having a pH of 5.5 to 8.0 and a polypeptide comprising one or more single variable domains at a concentration of 1 mg/mL to 200 mg/mL, said formulation being formulated for administration to a human subject, and said formulation further comprising an excipient at a concentration of 1% to 20%, wherein said formulation has an inorganic salt concentration of 150 mM or lower.

F-4. The formulation of any of aspect F-1 to F-3, wherein said single variable domain is susceptible to dimerization.

F-5. The formulation of aspect F-4, wherein the inorganic salt concentration is from 50 mM to 100 mM or lower.

F-6. The formulation of aspect F-5, that does not contain any inorganic salt.

F-7. The formulation of any of aspect F-1 to F-6, wherein the polypeptide has a melting temperature of at least 59° C. or more (such as 59.5° C. or more), preferably at least 60° C. or more (such as 60.5° C. or more), more preferably at least 61° C. or more (such as 61.5° C. or more) or at least 62° C. or more (such as 62.5° C. or more), most preferably at least 63° C. or more (such as 63.5° C. or more) as measured by the thermal shift assay (TSA) and/or differential scanning calorimetry (DSC).

F-8. The formulation of aspect F-7, wherein the formulation at least comprises an excipient at a concentration of 1% to 20%.

F-9. The formulation of aspect F-7, wherein the excipient is a dissaccharide and/or a polyol.

F-10. The formulation of aspect F-9, wherein the excipient is selected from sucrose, mannitol, sorbitol and trehalose.

F-11. The formulation of any of aspects F-8 to F-10, wherein the excipient has a concentration of 2.5% to 15%, preferably 5% to 10%, such as 5%, 7.5%, 8% or 10%.

F-12. The formulation of any of aspects F-1 to F-11, wherein the polypeptide is stable during storage at a temperature of 37±5° C. up to at least 2 weeks (preferably at least 3 weeks, at least 5 weeks, at least 8 weeks, at least 10 weeks, at least 3 months, at least 6 months, at least 1 year, 1.5 year or even 2 years or more), said stability as determined by SE-HPLC.

F-13. The formulation of aspect F-12, wherein less than 10% (preferably less than 7.5%, more preferably less than 5%, most preferably less than 2%) of the polypeptides forms dimers during storage, the % of dimers as measured by SE-HPLC.

F-14. The formulation of aspect F-13, wherein the formulation at least comprises an excipient at a concentration of 1% to 20%.

F-15. The formulation of aspect F-14, wherein the excipient is a disaccharide and/or a polyol.

F-16. The formulation of aspect F-14, wherein the excipient is a non-reducing sugar.

F-17. The formulation of aspect F-15 or F-16, wherein the excipient is selected from trehalose, mannitol and sucrose.

F-18. The formulation of any of aspects F-14 to F-17, wherein the excipient has a concentration of 2.5% to 15%, preferably 5% to 10%, such as 5%, 7.5%, 8% or 10%.

F-19. The formulation of any of aspects F-12 to f-18, wherein at least 80% (preferably at least 90%, more preferably at least 95% or even at least 99%) of the polypeptides retain their binding activity to at least one of their targets after storage compared to the binding activity prior to storage, said binding activity as measured by ELISA and/or Biacore.

F-20. The formulation of aspect F-19, wherein the formulation at least comprises an excipient at a concentration of 1% to 20%.

F-21. The formulation of aspect F-20, wherein the excipient s a disaccharide and/or a polyol.

F-22. The formulation of aspect F-20, wherein excipient is a non-reducing sugar.

F-23. The formulation of aspect F-21 or F-22, wherein the excipient is selected from mannitol, trehalose and sucrose.

F-24. The formulation of any of aspects F-20 to F-23, wherein the excipient has a concentration of 2.5% to 15%, preferably 5% to 10%, such as 5%, 7.5%, 8% or 10%.

F-25. The formulation of any of aspects F-1 to F-24, wherein the aqueous carrier is distilled water.

F-26. The formulation of any of aspects F-1 to F-24, wherein the aqueous carrier is MilliQ grade water or Water for Injection (WFI).

F-27. The formulation according to any of aspects F-1 to F-26, which is isotonic or slightly hypotonic.

F-28. The formulation according to aspect F-27, which has an osmolality of 290±60 mOsm/kg.

F-29. The formulation of any of aspects F-1 to F-28, wherein the polypeptide comprises two or more single variable domains, such as two or three.

F-30. The formulation of any of aspects F-1 to F-29, wherein the polypeptide specifically binds serum albumin (preferably human serum albumin), vWF, RANKL or IL-6R.

F-31. The formulation of any of aspects F-1 to F-30, wherein the polypeptide comprises at least a single variable domain that binds serum albumin, preferably human serum albumin.

F-32. The formulation of aspect F-31, wherein the polypeptide is selected from one of SEQ ID NO's: 1 to 6 and 9 to 14.

F-33. A method for the preparation of a formulation of any of aspects F-1 to F-32, at least comprising the step of concentrating the polypeptide and exchanging it with the selected buffer and excipient.

F-34. A sealed container containing a formulation according to any of aspects F-1 to F-32.

F-35. A pharmaceutical unit dosage form suitable for parenteral administration to a human, comprising a formulation according to any of aspects F-1 to F-32 in a suitable container.

F-36. A kit comprising one or more of the sealed containers according to aspect F-34 and/or pharmaceutical unit dosage forms according to aspect F-35, and instructions for use of the formulation.

F-37. The formulation, container, pharmaceutical unit dosage or kit according to any of the preceding aspects for use in therapy.

F-38. Method for prevention and/or treatment of one or more diseases and/or disorders, comprising administering to a subject in need thereof a formulation according to any of aspects F-1 to F-32.

F-39. Method of aspect F-38, wherein the disease and/or disorder is a disease and/or disorder associated with aberrant expression and/or activity of RANKL, disease and/or disorder associated with overexpression of IL-6, or vascular disease and/or disorder.

F-40. Method of aspect F-39, wherein the disease and/or disorder is selected from osteoporosis, cancer induced bone loss and/or bone loss associated with autoimmunity and/or viral infection.

F-41. Method of aspect F-39, wherein the disease and/or disorder is selected from rheumatoid arthritis, abnormal synovial cell growth, plasmocytosis induced Castleman's disease, tumor, muscle protein proteolysis, multiple sclerosis, systemic lupus erythematosus, inflammatory bowel disease, pancreatitis, psoriasis, angiogenesis, systemic-onset type juvenile rheumatoid arthritis, spinal cord injury, endothelial injury or destruction, mesothelioma, vasculitis, osteoarthritis, inner ear disorder, cancer, rejection after transplantation, pancreatic islet transplantation, myocardial infarction, prostate cancer, choroidal neovascularization, muscle regeneration, inflammatory myopathy, chronic rejection in cardiac transplant, delayed graft function.

F-42. Method of aspect F-39, wherein the disease and/or disorder is selected from acute coronary syndrome (ACS), myocardial infarction, thrombotic thrombocytopenic purpura (TTP) or Moschcowitz syndrome, vascular surgery and stroke.

EXAMPLES

Example 1

Generation of NFDs 1.1 Fermentation of Polypeptide A (SEQ ID NO: 1) Producing *E. coli* Clone Fermentation of Polypeptide A (SEQ ID NO: 1) clone 1 (identified as disclosed in WO 2006/122825) was carried out at 10 liter scale in Terrific Broth (Biostat Bplus, Sartorius) with 100 µg/ml carbenicillin. A two percent inoculum of the preculture (grown overnight in TB, 2% glucose, 100 µg/ml carbenicillin) was used to start the production culture (22° C./lvvm). Induction (using 1 mm IPTG) was started at an $OD_{600}$ of 8.0. After a short induction at 22° C., the cell paste was collected via centrifugation (Sigma 8K, rotor 12510; 7000 rpm for 30 min) and frozen at −20° C.

1.2 Purification of Polypeptide A

Purified Polypeptide A (monomer and dimer) was generated via a process consisting of 6 steps:

1.2.1 Extraction from Cell Pellet

The frozen cell pellet was thawed, the cells were resuspended in cold PBS using an Ultra Turrax (Ika Works; S25N-25G probe, 11.000 rpm.) and agitated for 1 h at 4° C. This first periplasmic extract was collected via centrifugation; a second extraction was carried out in a similar way on the obtained cell pellet. Both extractions did account for more than 90% of the periplasmic Polypeptide A content (the $2^{nd}$ extraction did yield about 25%).

1.2.2 Removal of Major Contaminants via Acidification

The periplasmic extract was acidified to pH=3.5 using 1M citric acid (VWR (Merck) #1.00244.0500) 10 mM molar final pH=3.5 and further pH adjusted with 1M HCl. The solution was agitated overnight at 4° C. The precipitated proteins and debris was pelleted down via centrifugation.

1.2.3 Micro-Filtration and Concentration of the Extract

The supernatant was made particle free using a Sartocon Slice Crossflow system (17521-101, Sartorius) equipped with Hydrosart 0.20 µm membrane (305186070 10-SG, Sartorius) and further prepared for Cation Exchange Chromatography (CEX) via Ultra filtration. The volume that needed to be applied to CEX was brought down to approx 2 liter via ultra filtration using a Sartocon Slice Crossflow system equipped with Hydrosart 10,000 MWCO membranes (305144390 1E-SG, Sartorius). At that point the conductivity (<5 mS/cm) and pH (=3.5) were checked.

1.2.4 Capture and Purification via CEX

The cleared and acidified supernatant was applied to a Source 30S column (17-1273-01, GE Healthcare) equilibrated in buffer A (10 mM Citric acid pH=3.5) and the bound proteins were eluted with a 10 CV linear gradient to 100% B (1 M NaCl in PBS). The Polypeptide A fraction was collected and stored at 4° C.

1.2.5 Affinity Purification on Protein A Column

Figure 7:
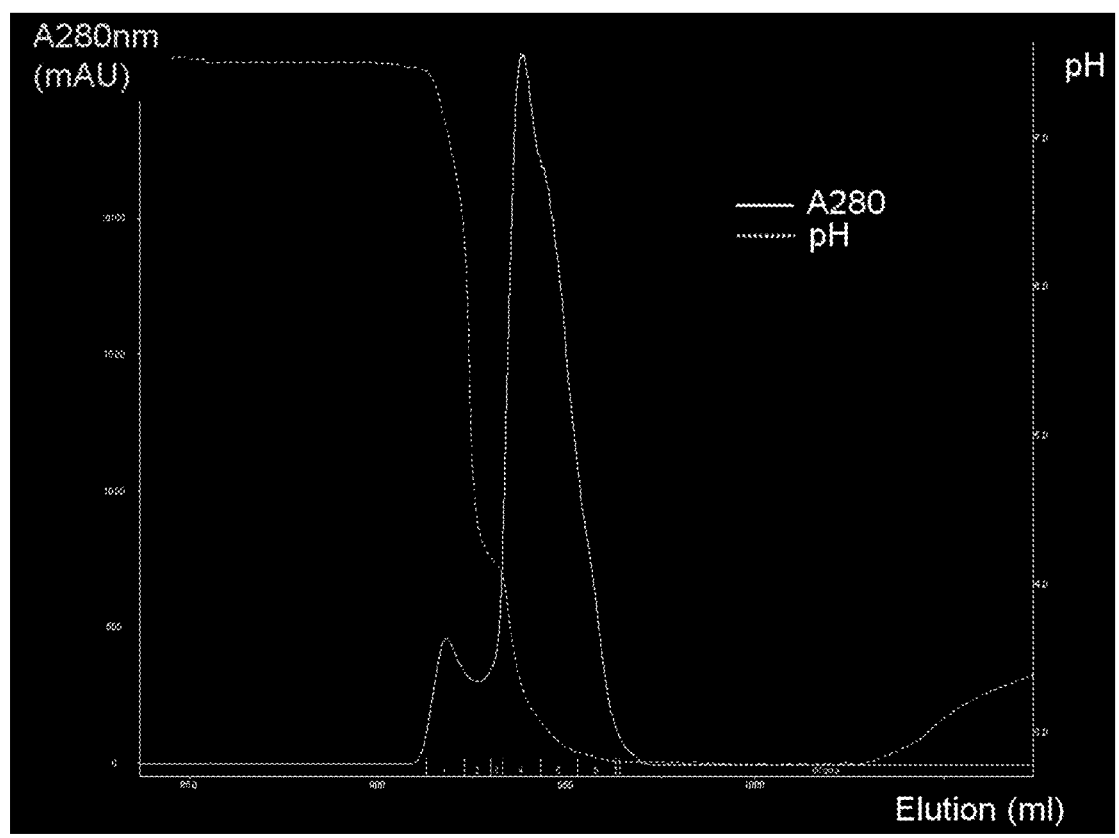
FIG. 7: Protein A elution of Polypeptide A. The pretreated periplasmic extract was loaded on a Protein A MabSelectXtra column, followed by a PBS wash until stable baseline. Elution was carried out via a pH shift using 100 mM glycine pH=2.5 (dotted line).

Polypeptide A (amount=well below column capacity) was further purified via Protein A affinity chromatography (Mab-Select Xtra™, 17-5269-07, GE Healthcare). A one step elution was carried out using 100 mM Glycine pH 2.5. The collected sample was immediately neutralized using 1M Tris pH 7.5 (see FIG. 7).

1.2.6 Size Exclusion Chromatography (Optional e.g. In Order to Isolate NFDs and/or Determine Amount of NFDs)

Figure 8:
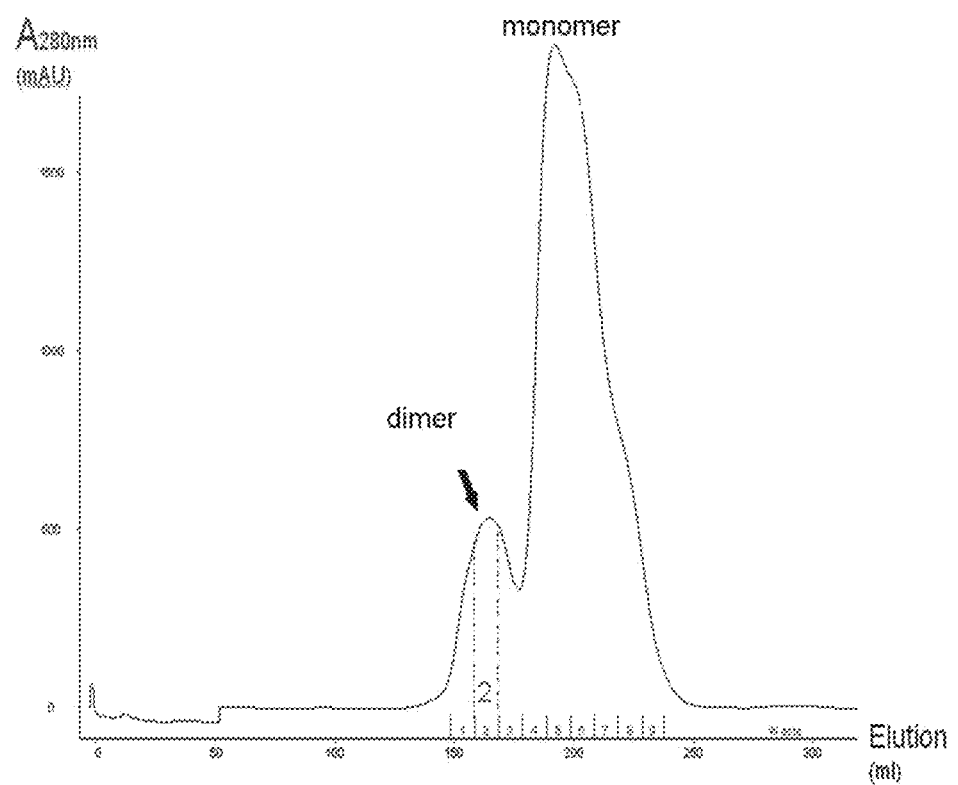
FIG. 8: Size Exclusion Chromatography of Polypeptide A monomer and dimer. The pre-peak (fraction 2) contains the dimeric Polypeptide A which was used in the stability studies.

The purified Nanobody® fraction was further separated and transferred to D-PBS (Gibco #14190-169) via SEC using a Hiload™ XK26/60 Superdex 75 column (17-1070-01, GE Healthcare) equilibrated in D-PBS. Fraction 2 contained the dimeric Polypeptide A (see FIG. 8).

Figure 3:
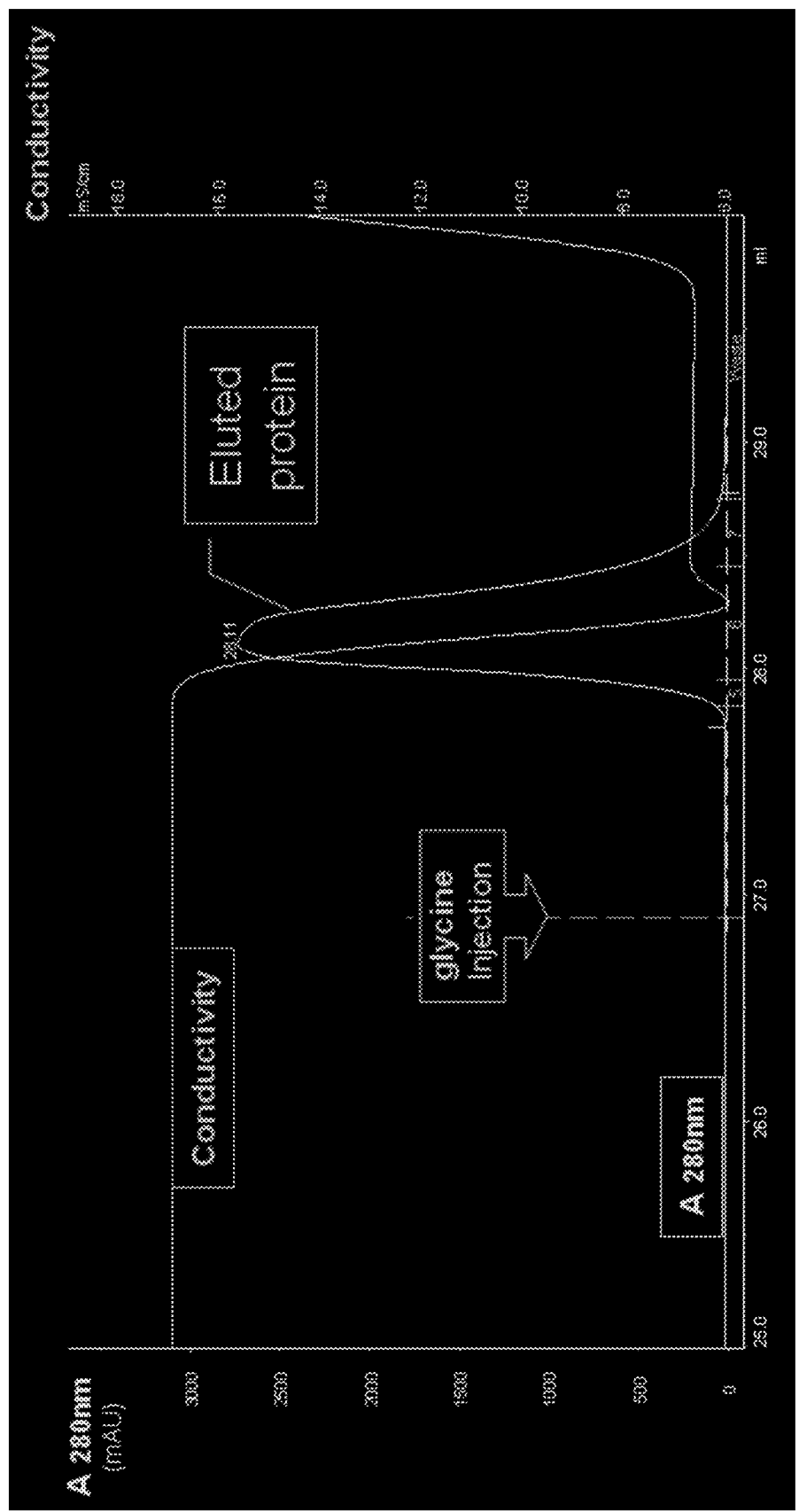
FIG. 3: Protein A affinity purification of polypeptide A (SEQ ID NO: 1) under conditions resulting in significant amounts of NFDs. The protein was loaded on a small column (400 µl resin MabSelectXtra, GE Healthcare) and eluted via injection of glycine [100 mM, pH=2.5]. The pH of the eluted Nanobody® solution was immediately neutralized using 1M Tris pH 8.8.

In a further experiment, Polypeptide A (SEQ ID NO: 1) was accumulated on a Protein A column, its concentration well above Sing polypeptide A/ml resin, and eluted via a steep pH shift (one step buffer change to 100 mM Glycine pH 2.5). During elution of the polypeptide A from the column it was 'stacked' into an elution front, consisting of 'locally' very high concentrations (actual value after elution >5 mg/ml), and combination with the pH shift led to the isolation of about 50% stable dimer (see FIG. 3).

Figure 4:
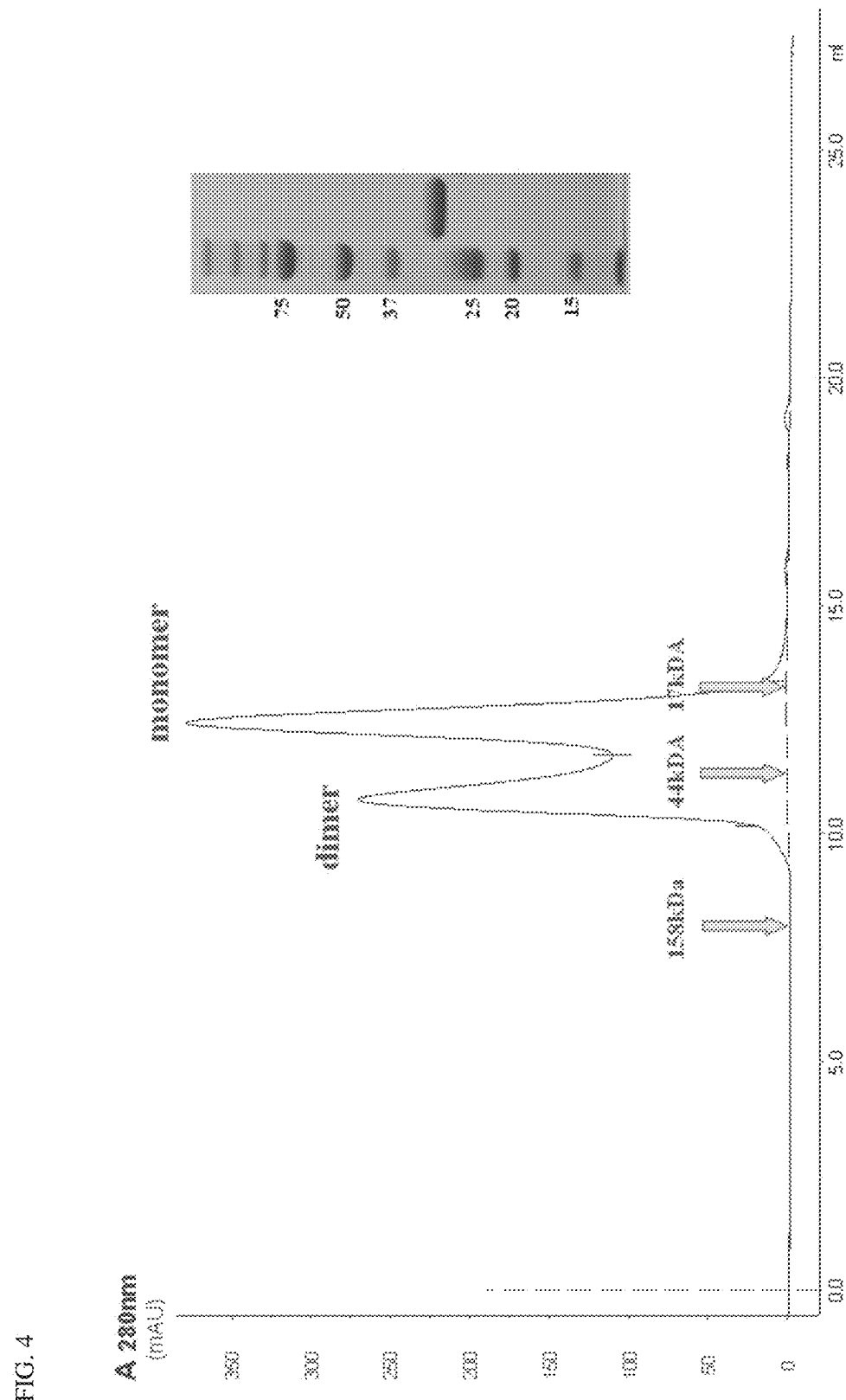
FIG. 4: Size exclusion chromatography of Protein A affinity purified polypeptide A. Separation of concentrated polypeptide A (fraction 6, see FIG. 3) on an analytical Superdex 75 column (GE Healthcare). The Nanobody® fraction was resolved into two specific fractions corresponding to the molecular weight of monomeric and dimeric polypeptide A (position of molecular weight markers is indicated). Analysis via SDS-PAGE (right panel) did not reveal any difference between the two, indicating that under native conditions they behave as monomer and dimer. The latter is converted into a monomer conformation upon denaturation (SDS detergent and heat treatment).
Figure 5:
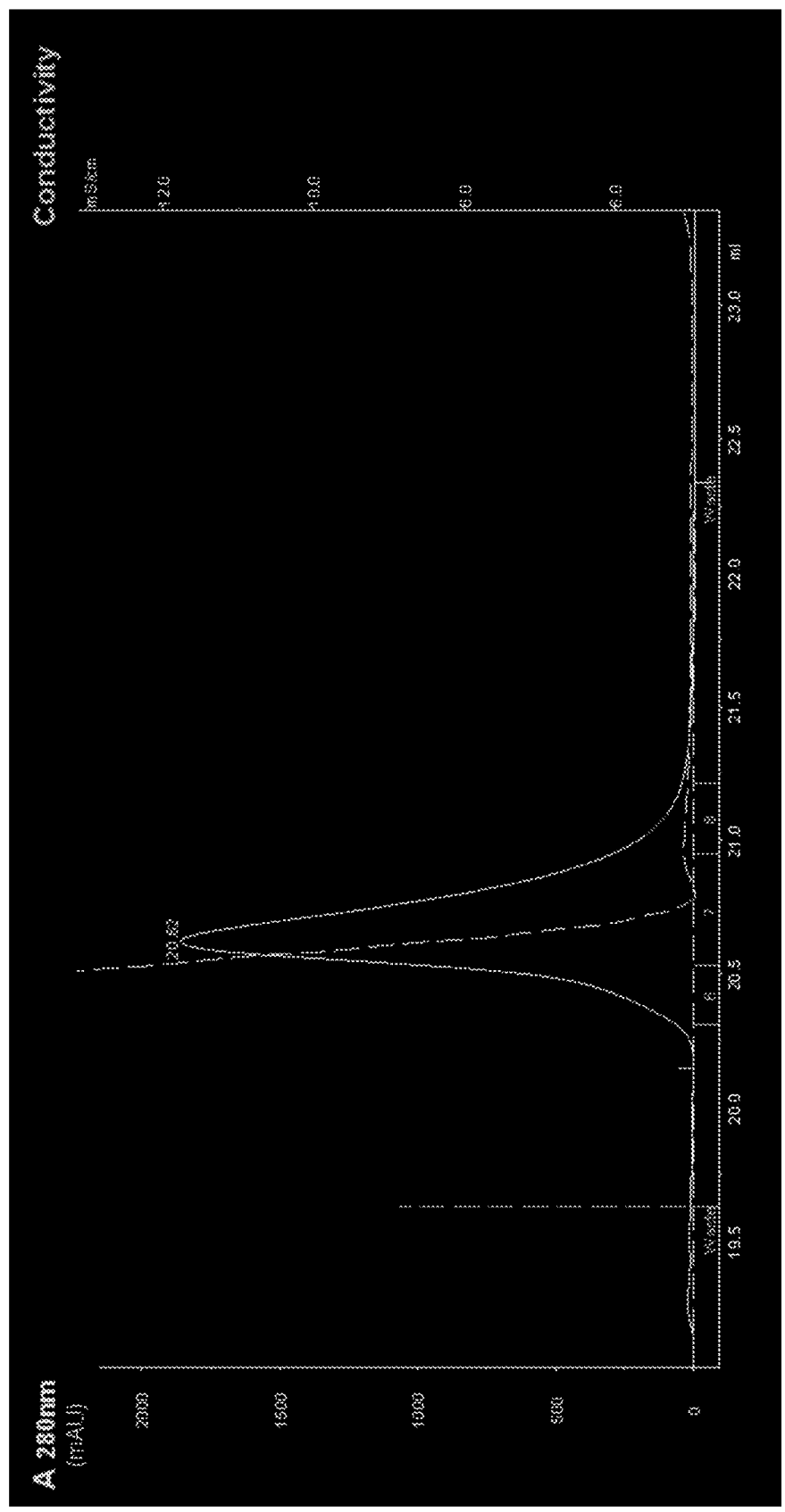
FIG. 5: Protein A affinity purification of polypeptide A at low column load. A limited amount of protein [approx. 2.5 mg/ml resin] was loaded on a small column (400 µl resin MabSelectXtra, GE Healthcare) and eluted via injection of glycine [100 mM, pH=2.5]. The pH of the eluted Nanobody® solution was immediately neutralized using 1M Tris pH 8.8.
Figure 6:
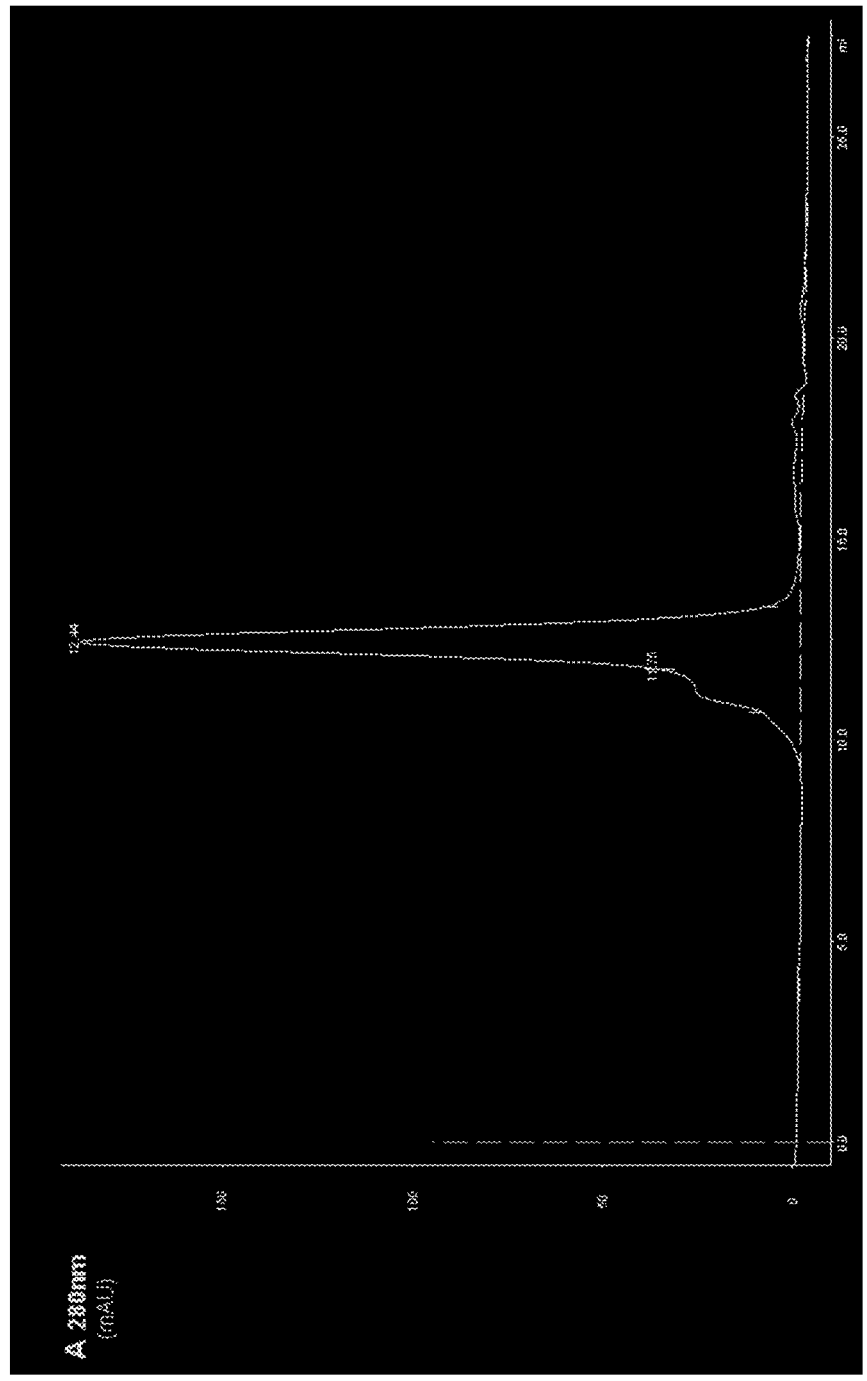
FIG. 6: Size exclusion chromatography of Protein A affinity purified polypeptide A. Separation of concentrated polypeptide A (fraction 7, see FIG. 5) on an analytical Superdex 75 column (GE Healthcare). The Nanobody® fraction was resolved into a specific fraction corresponding to the molecular weight of monomeric polypeptide.

The shift from monomer to dimer is demonstrated via size exclusion chromatography (SEC), allowing determination of the percentage of dimerization (see FIG. 4). When loading less polypeptide A on Protein A (i.e. 2 mg/ml resin under otherwise same conditions as above, i.e. one step elution with 100 mM Glycine pH 2.5), almost no dimers (<5%) were detected during SEC (see FIG. 5 and FIG. 6). Similarly, NFDs of a polypeptide comprising one singe variable domain (NFD-Mo), a polypeptide comprising three single variable domains (NFD-Tri), and a polypeptide comprising a HSA (human serum albumin) and a single variable domain fusion were obtained (see Table 1).

TABLE 1

Examples of obtained NFDs

| Code for Monomeric polypeptide | SEQ ID NO of monomeric building block | Obtained by | Isolated stable NFD type | Monomeric polypeptide comprising |
|---|---|---|---|---|
| Polypeptide A | 1 | Protein A + SEC | NFD-Di | Two identical single variable domains |
| Polypeptide B, also referred to as Alb11 | 2 | IMAC + AEX + SEC; Protein A + SEC | NFD-Mo | One single variable domain binding to human serum albumin |
| Polypeptide C | 3 | Protein A + SEC | NFD-Tri | Three single variable domains of which one binds to human serum albumin and the two other single variable domains bind to a receptor target |
| Polypeptide D | 4 | Protein A + SEC | NFD-Mo | Singe variable domain and HSA |
| Polypeptide E | 5 | Protein A + SEC | NFD-Di | Two single variable domains of which one binds to human serum albumin and the other single variable domain binds to a receptor target |
| Polypeptide F | 6 | Protein A + SEC | NFD-Mo | One single variable domain binding to human serum albumin |

Example 2

Stability of NFDs

During purification of Polypeptide A stable non fused dimers (NFDs) were generated (see above). In order to get more insight into the stability and nature of this non-covalent interaction, stable Polypeptide A NFDs were subjected to distinctive conditions aiming to dissociate the dimer into monomer. The stability of the complex was evaluated via 3 criteria: heat-stability, pH-stability, organic solvent resistance and combinations thereof.

2.1 Experimental Set Up

Figure 9:
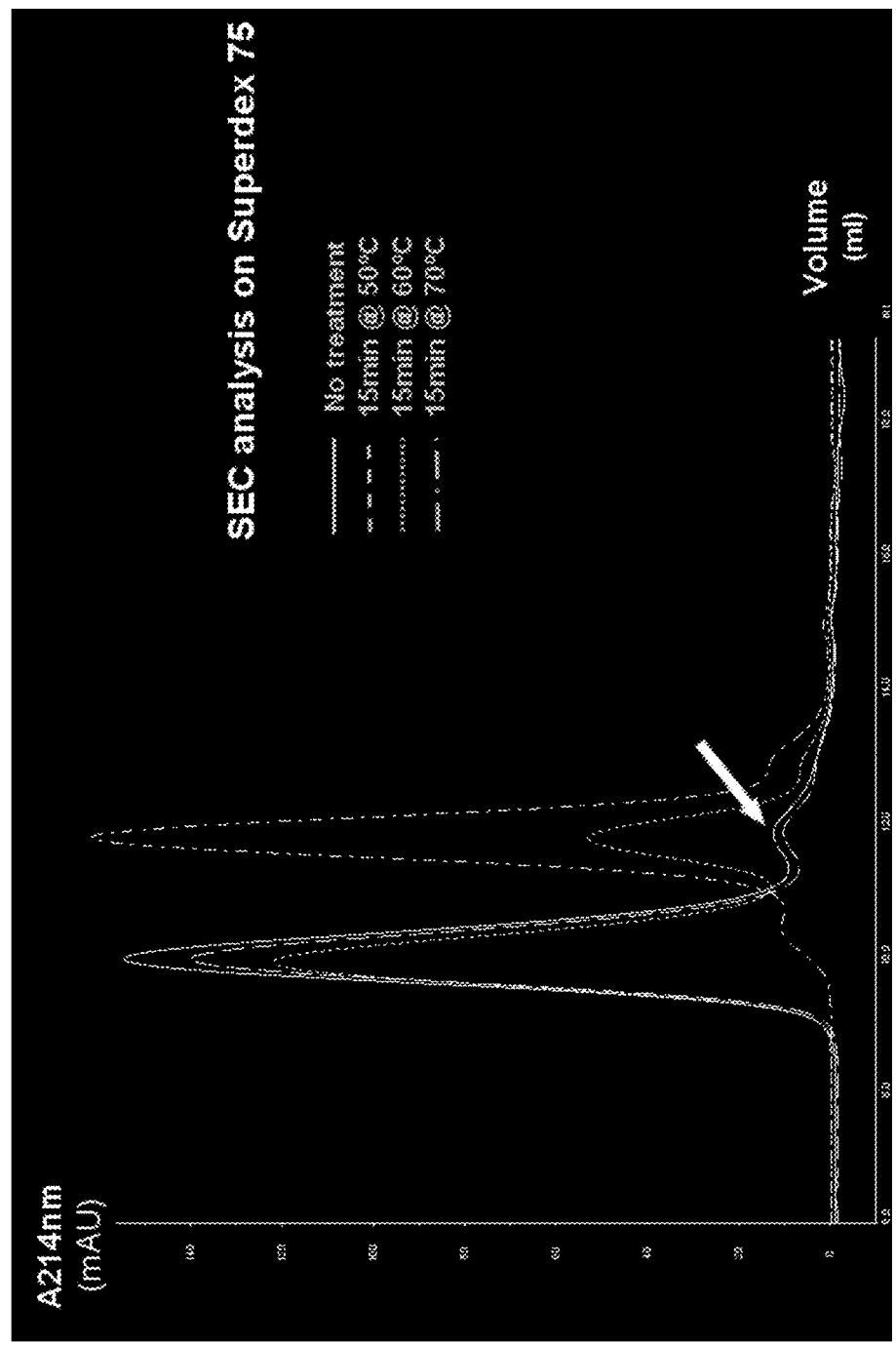
FIG. 9: Size exclusion chromatography of heat treated samples of dimeric Polypeptide A. Polypeptide A NFD (at 0.68 mg/ml) was used in several experiments: 20 µl dimer fractions were diluted with 90 µl D-PBS and incubated at different temperatures and 100 µl was analysed on a Superdex 75™ 10/300GL column equilibrated in D-PBS.

The Polypeptide A NFD was generated during a Polypeptide A preparation (see above) and was stored at −20° C. for 2.5 years. This dimeric material was obtained via Protein A chromatography and Size Exclusion Chromatography (SEC) in PBS. In the latter, monomeric and dimeric material were separated to a preparation of >95% pure dimer. Upon thawing about 5% monomeric material was detected (see arrow in FIG. 9). The concentration of dimeric material was 0.68 mg/ml.

Analytic Size Exclusion Chromatography

The stability of the Polypeptide A NFD dimer was analysed via analytic SEC on a Superdex 75 10/300GL, column (17-5174-01, GE Healthcare) using an Äkta Purifier10 workstation (GE Healthcare). The column was equilibrated in D-PBS at room temperature (20° C.). A flow rate of 1 ml/min was used. Proteins were detected via absorption at 214 nm. 12 μg samples of Polypeptide A NFD were injected.

Overview Analytic SEC Runs:

20 μl POLYPEPTIDE A NFD+90 μl D-PBS→15'/50° C.→100 μl analyzed

20 μl POLYPEPTIDE A NFD+90 μl D-PBS→15'/20° C.→100 μl analyzed

20 μl POLYPEPTIDE A NFD+90 μl D-PBS→30'/45° C.→100 μl analyzed

20 μl POLYPEPTIDE A NFD+90 μl D-PBS→15'/60° C.→100 μl analyzed

20 μl POLYPEPTIDE A NFD+90 μl D-PBS→15'/70° C.→100 μl analyzed

20 μl POLYPEPTIDE A NFD+90 μl [100 mM Piperazin pH=10.2]→ON/4° C.→100 μl analyzed 20 μl POLYPEPTIDE A NFD+90 μl [100 mM Glycin pH=2.5]→ON/4° C.→100 μl analyzed 20 μl POLYPEPTIDE A NFD+90 μl [10% Isopropanol] →ON/4° C.→100 μl analyzed 20 μl POLYPEPTIDE A NFD+90 μl [30% Isopropanol] →ON/4° C.→100 μl analyzed 20 μl POLYPEPTIDE A NFD+90 μl [1% TFA]→15'/20° C.→100 μl analyzed 20 μl POLYPEPTIDE A NFD+90 μl [30% Isopropanol] →15'/50° C.→100 μl analyzed 20 μl POLYPEPTIDE A NFD+90 μl [30% Isopropanol] →15'/20° C.→100 μl analyzed 20 μl POLYPEPTIDE A NFD+90 μl [30% Isopropanol] →15'/40° C.→100 μl analyzed 20 μl POLYPEPTIDE A NFD+90 μl [30% Isopropanol] →15'/45° C.→100 μl analyzed This material was used in several experiments: 20 μl dimer fractions were diluted with 90 μl D-PBS or other solvents, incubated under different conditions and 100 μl samples were analysed via analytic SEC.

2.2 Tests

In a first set of experiments incubation during 15 minutes at increasing temperatures was carried out (45, 50, 60 and 70° C.), followed by analytic SEC (Superdex™ 10/300GL). An incubation at 70° C. during 15 min resulted in an almost complete shift to monomeric Polypeptide A, whereas lower temperatures (e.g. 50° C.) did not result in such a drastic effect. After 15 minutes at 60° C. about 25% dissociated material was detected (see FIG. 9).

Figure 10:
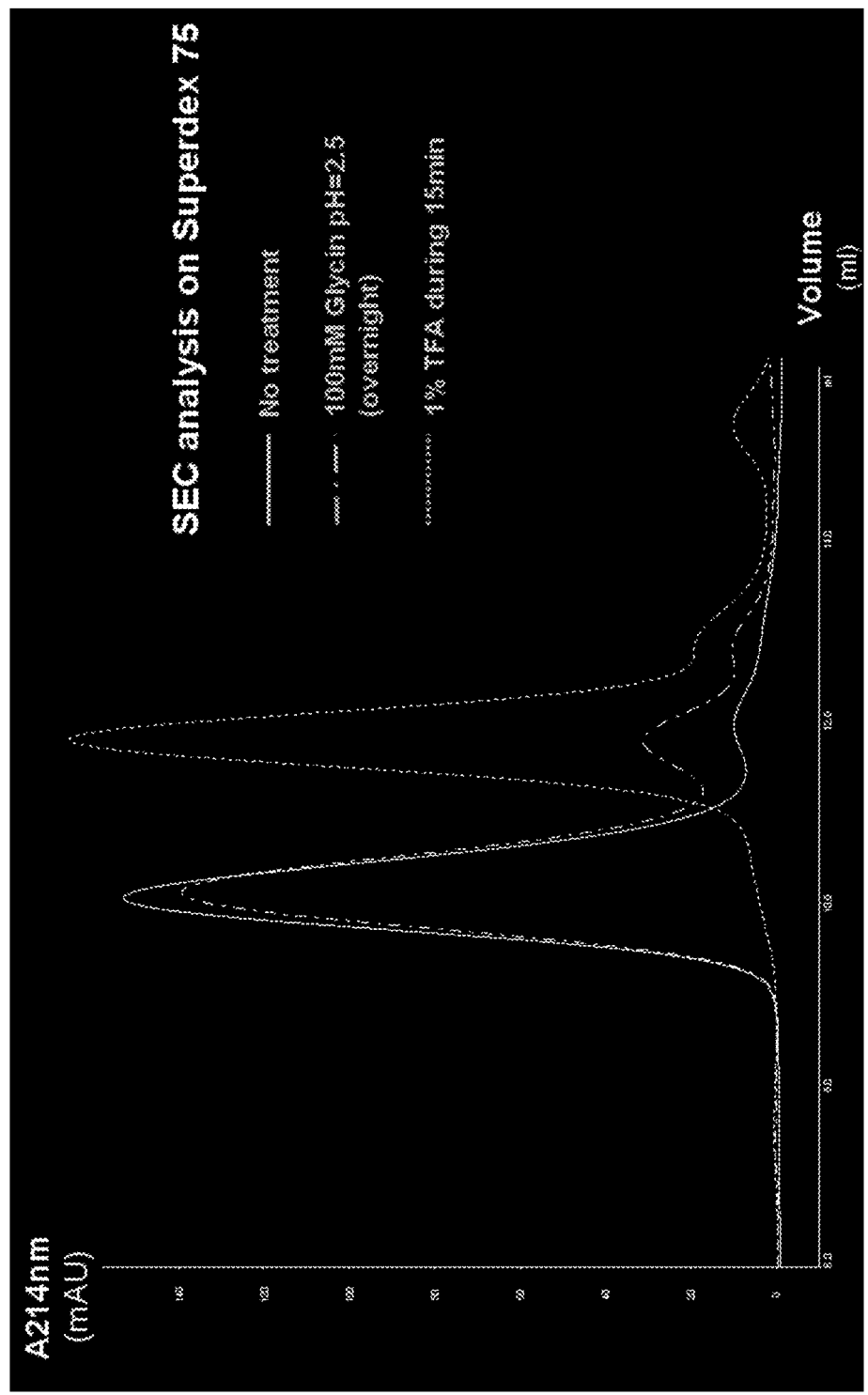
FIG. 10: Size exclusion chromatography of pH treated samples of Polypeptide A NFD. Polypeptide A NFD (at 0.68 mg/ml) was used in several experiments: 20 µl dimer samples were diluted with 90 µl [1.00 mM Piperazine pH=10.2] or 90 µl [100 mM Glycine, pH=2.5] and incubated overnight (ON) at 4° C. The control was incubated in D-PBS. Samples were analysed via SEC the next day. The incubation at elevated pH had no effect on the dissociation whereas low pH (glycine pH=2.5) resulted in approx 15% monomer. A more drastic incubation in 1% TFA during 15 min at room temperature resulted in almost 100% monomer.

In a second set of experiments the effect of pH on the stability of Polypeptide A NFD was explored. 20 µl NFD was mixed with 90 µl [100 mM Piperazin pH=10.2] or 90 µl [100 mM Glycine, pH=2.5] and incubated overnight (ON) at 4° C. 20 µl NFD was mixed with 90 µl [1% TFA] at room temperature for 15 minutes and then immediately analysed via SEC. The control was incubated in D-PBS. Samples were analysed via SEC the next day (see FIG. 10).

Figure 11:
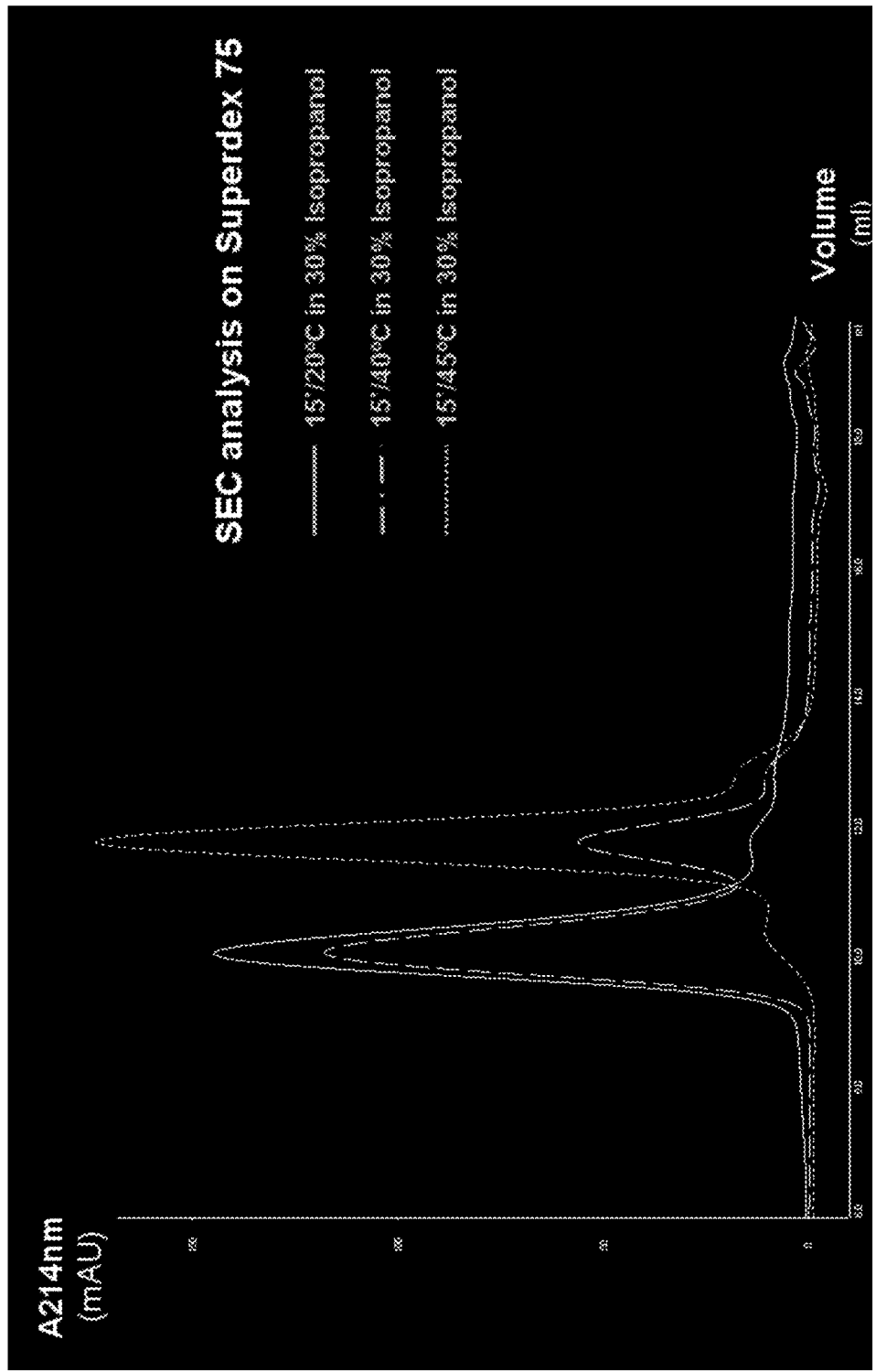
FIG. 11: Size exclusion chromatography of combined heat/organic solvent treated samples of Polypeptide A NFD. Polypeptide A NFD (at 0.68 mg/ml) was used in several experiments: 20 µl dimer fractions were diluted with 90 µl [10% Isopropanol] or 90 µl [30% Isopropanol] and incubated overnight (ON) at 4° C. or 15 minutes at 20° C. Combined treatments (heat and Isopropanol) were carried out during 15 minutes. The control was incubated in D-PBS. Samples were analysed via SEC. The incubation at elevated temperature with organic solvent resulted in accelerated dissociation into monomer.

A third set of experiments consisted of a combined treatment: Temperature and organic solvent (Isopropanol). Neither incubation in 10 or 30% Isopropanol overnight at 4° C., nor incubation in 10 or 30% Isopropanol during 15 minutes at room temperature resulted in any significant dissociation. However, combining increased temperatures and organic solvent resulted in a much faster dissociation into monomer. Whereas incubation at 45° C. or 30% Isopropanol had no effect alone, combining both (during 15 minutes) resulted in an almost full dissociation into monomer. Isopropanol treatment at 40° C. yielded only 30% dissociation (see FIG. 11).

2.3 Discussion

The concentration independent character of the dimer/monomer equilibrium was further substantiated by the near irreversibility of the interaction under physiological conditions. In addition, the rather drastic measures that needed to be applied to (partly) dissociate the dimer into monomer point to an intrinsic strong interaction. Dissociation is only obtained by changing the conditions drastically (e.g. applying a pH below 2.0) or subjecting the molecule to high energy conditions. Temperature stability studies (data not shown) indicate that the Tm of Polypeptide A NFD is 73° C., so the observed dissociation into monomer might be indeed linked to (partial) unfolding.

The solubilizing properties of TFA combined with protonation at extreme low pH, increasing the hydrophilicity, also results in dissociation.

The combination of elevated temperature and organic solvent dissociation indicates that the interaction is mainly based on e.g. hydrophobicity (e.g. Van der Waals force), hydrogen bonds, and/or ionic interactions.

The conditions used to drive these dimers apart may be also useful to explore when determining further methods for producing these dimers, i.e. combining these procedures (e.g. temperature of higher than 75 degrees Celsius) with a high polypeptide concentration.

Example 3

Ligand Binding of NFDs

The binding of Ligand A (SEQ ID NO: 7) to Polypeptide A and Polypeptide A NFD-Di was studied via analytic size exclusion.

3.1 Ligand A Production

Ligand A is known to be the binding domain of Polypeptide A, i.e. it comprises the epitope of Polypeptide A (i.e. Ligand A represents the A1 domain of vWF).

Ligand A [1.46 mg/ml] was produced via *Pichia* in shaker flasks. Biomass was produced in BGCM medium. For induction a standard medium switch to methanol containing medium (BMCM) was done. The secreted protein was captured from the medium via IMAC, further purified on a Heparin affinity column and finally formulated in 350 mM NaCl in 50 mM Hepes via Size Exclusion Chromatography (SEC) (Superdex 75 HiLoad 26/60).

3.2 Analytic SEC on Superdex 200 10/300GL

Figure 12:
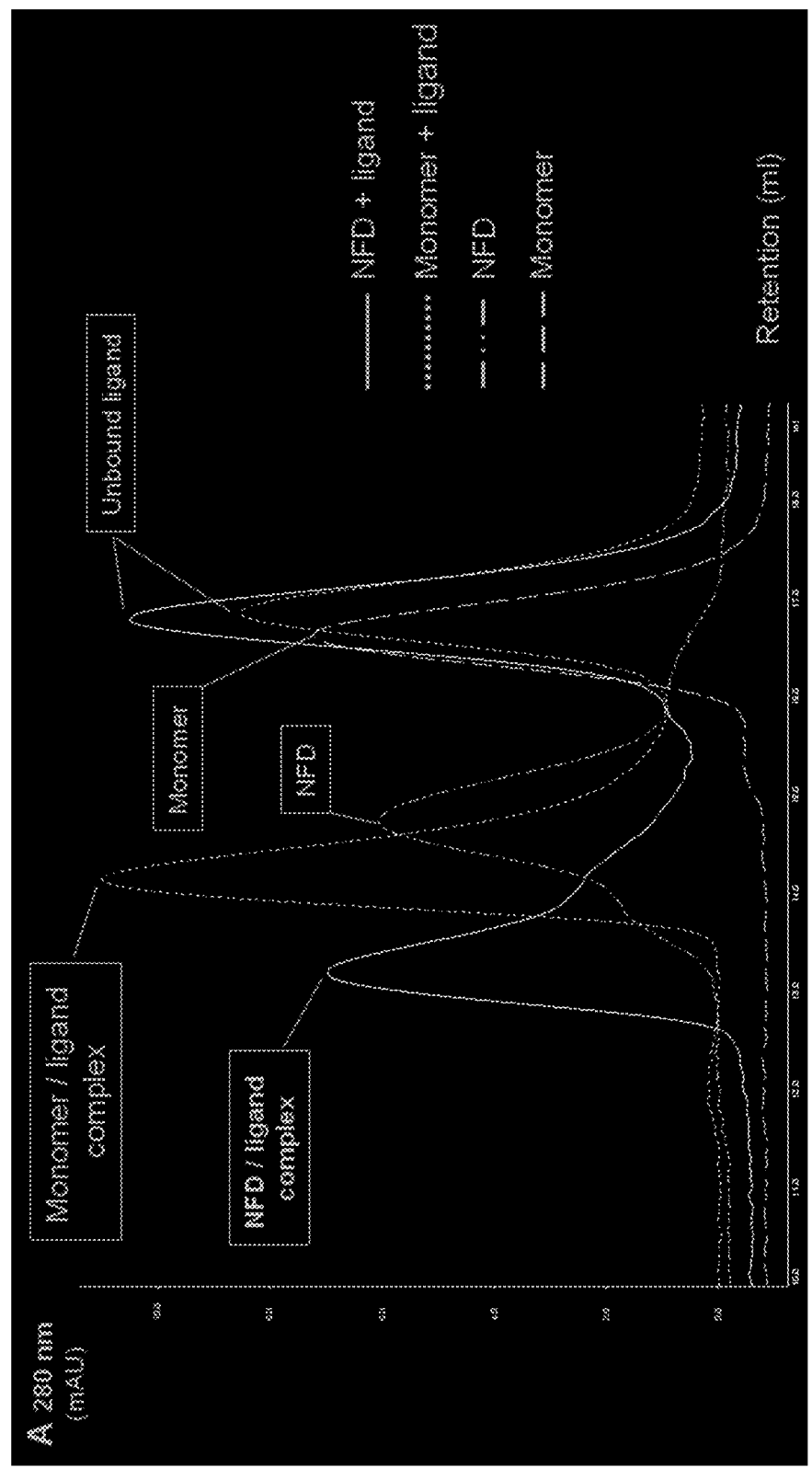
FIG. 12: Size exclusion chromatography of ligand-NFD complex formation: 20 µl samples of Ligand A (SEQ ID NO: 7) was diluted in 90 µl [JIBS-EP (Biacore)+0.5M NaCl] and incubated for several hours at RT (ligand mix). Then NFD or Polypeptide A was added and after a short incubation (typically 30 min) the material was resolved via SEC. Polypeptide A [3.91 mg/ml]: 17 µl [1/10 diluted in HBS-EP] was added to the ligand mix and 100 µl was injected.

Polypeptide A (with 2 expected binding sites) and its corresponding NFD (with 4 expected binding sites) were obtained as disclosed in example 1 and added to 5× excess of the Ligand A. The resulting shift in molecular weight was studied via size exclusion chromatography (SEC) (FIG. 12). The shift in retention approximately indicates the number of Ligand A molecules binding to the Polypeptide A or corresponding NFD. Ligand A has a molecular weight of about 20 kDa. The molecular weight shift of the NFD/Ligand A complex compared to NFD alone or Polypeptide/Ligand A complex to Polypeptide A indicates the number of Ligand A per NFD or per Polypeptide A bound (see Table 2).

TABLE 2

Molecular weight shift of the NFD/Ligand A complex compared to NFD alone or Polypeptide/Ligand A complex to Polypeptide A

| Material | Retention (ml) | Measured MW (KDa)* | Theoretical MW (Da) | Measured MW shift with ligand A exposure | Estimated Number of Ligand A bound |
|---|---|---|---|---|---|
| NED + Ligand A | 13.2 | 123.6 | 153940 (assuming 4 Ligand A bindings) | 62.5 | 3 |
| Polypeptide A + ligand A | 14.1 | 79.1 | 76970 (assuming 2 Ligand A bindings) | 54.1 | 2 |
| NFD | 14.7 | 61.1 | (55752) | Not applicable | Not applicable |
| Polypeptide A | 16.6 | 25.0 | (27876) | Not applicable | Not applicable |
| Ligand A | 16.8 | 22.8 | (24547) | Not applicable | Not applicable |

Figure 13:
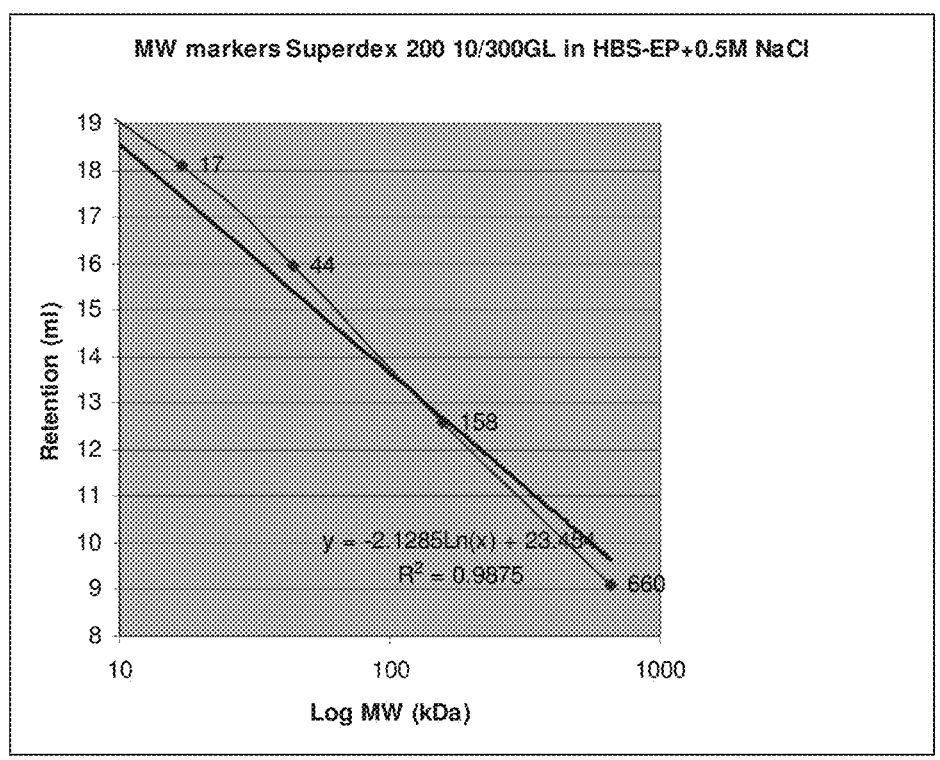
FIG. 13: The molecular weight (MW) of polypeptide A, Ligand A, Polypeptide A+Ligand A, NFD-Di of Polypeptide A, and NFD-Di of Polypeptide A+Ligand A was calculated (see Table 2 for read out from this figure) based on curve fitting of Molecular weight standards (Biorad #151-1901) run on the same column under same conditions.

*MW was calculated based on curve fitting of Molecular weight standards (Biorad #151-1901) run on the same column under same conditions (see FIG. 13).

3.3 Overview Analytic SEC Runs on Superdex 75 10/300GL (B7)040308.1: Complex ligand-NFD 5 µl mix (ON stored at 4° C.)+80 µl A buffer (B7)040308.2: 20 µl Molecular weight marker+80 µl A buffer (B7)040308.3: Complex 20 µl ligand+90 µl A buffer, 4 h at RT+Polypeptide A [17 µl 1/10], 30 min at RT before analysis (B7)040308.4: Polypeptide A [17 µl in 90 µl A buffer]

(B7)040308.5: Ligand in A buffer (1 h at RT)+Polypeptide A, 15 min at RT before analysis.

(B7)040308.6: Ligand+Buffer A+NFD
(B7)040308.7: rest sample #6 after 1 h at RT
(B7)040308.8: Buffer A+NFD The correlation of the expected MW shows that more than 2 ligands (likely 3 and possibly 4 due to the atypical behaviour of Ligand A complexes on the SEC) are bound by the NFD.

Example 4

Further Characterization of a NFD with Polypeptide B

Example 4.1

Crystal Structure of a Non-Fused Dimer: Polypeptide B 4.1.1 Crystallization

The protein was first concentrated to a concentration of about 30 mg/mL. The purified protein was used in crystallization trials with approximately 1200 different conditions. Conditions initially obtained have been optimized using standard strategies, systematically varying parameters critically influencing crystallization, such as temperature, protein concentration, drop ratio and others. These conditions were also refined by systematically varying pH or precipitant concentrations.

4.1.2 Data Collection and Processing

Crystals have been flash-frozen and measured at a temperature of 100K. The X-ray diffraction data have been collected from the crystals at the SWISS LIGHT SOURCE (SLS, Villingen, Switzerland) using cryogenic conditions.

The crystals belong to the space group $P\,2_1$ with 2 molecules in the asymmetric unit. Data were processed using the program XDS and XSCALE. Data collection statistics are summarized in Table 3.

TABLE 3

Statistics of data collection and processing

| | |
|---|---|
| X-ray source | PX-3 (SLS[1]) |
| Wavelength (Å) | 0.97800 |
| Detector | MARCCD |
| Temperature (K.) | 100 |
| Space group | $P\,2_1$ |
| Cell dimensions: | |
| a; b; c (Å) | 37.00; 67.06; 41.14 |
| α; β; γ (°) | 90.0; 97.7; 90.0 |
| Resolution (Å)[2] | 1.20 (1.30-1.26) |
| Unique reflections[2] | 60716 (4632) |
| Multiplicity[2] | 4.1 (4.1) |
| Completeness (%)[2] | 97.7 (96.7) |
| $R_{sym}$ (%)[2,3] | 7.2 (41.4) |
| $R_{meas}$ (%)[2,4] | 8.3 (47.6) |
| I/σ[2] | - (-) |
| Mean(I)/sigma[2,5] | 12.83 (4.01) |

[1]SWISS LIGHT SOURCE (SLS, Villingen, Switzerland)
[2]Numbers in brackets corresponds to the resolution bin with $R_{sym}$ = 41.4%

$$^3R_{sym} = \frac{\sum_h \sum_i^{n_h} \left| \hat{I}_h - I_{h,i} \right|}{\sum_h \sum_i^{n_h} I_{h,i}}$$

with $\hat{I}_h = \frac{1}{n} \sum_i^{n_h} I_{h,i}$, where $I_{h,i}$ is the intensity value of the ith measurement of h TABLE 3-continued Statistics of data collection and processing $$^4R_{sym} = \frac{\sum_h \sqrt{\frac{n_h}{n_h - 1}} \sum_i^{n_h} \left| \hat{I}_h - I_{h,i} \right|}{\sum_h \sum_i^{n_h} I_{h,i}}$$

with $\hat{I}_h = \frac{1}{n} \sum_i^{n_h} I_{h,i}$, where $I_{h,i}$ is the intensity value of the ith measurement of h

[5]Calculated from independent reflections 4.1.3 Structure Modelling and Refinement The phase information necessary to determine and analyze the structure was obtained by molecular replacement. Subsequent model budding and refinement was performed according to standard protocols with the software packages CCP4 and COOT. For the calculation of the R-factor, measure to cross-validate the correctness of the final model, 1.6% of measured reflections were excluded from the refinement procedure (Table 4). The ligand parameterisation was carried out with the program CHEMSKETCH. LIBCHECK (CCP4) was used for generation of the corresponding library files.

Statistics of the final structure and the refinement process are listed in Table 4.

TABLE 4

Refinement statistics[1]

| | |
|---|---|
| Resolution (Å) | 20.0 – 1.20 |
| Number of reflections (working/test) | 59743/972 |
| $R_{cryst}$ (%) | 14.8 |
| $R_{free}$ (%) | 16.9 |
| Total number of atoms in protein | 1759 |
| Deviation from ideal geometry[2] | |
| Bond lengths (Å) | 0.006 |
| Bond angles (°) | 1.17 |

[1]Values as defined in REFMAC5, without sigma cut-off
[2]Root mean square deviations from geometric target values 4.1.4 Overall Structure The asymmetric unit of crystals is comprised of 2 monomers. The Nanobody® is well resolved by electron density maps.

4.1.5 Structure

Figure 14:
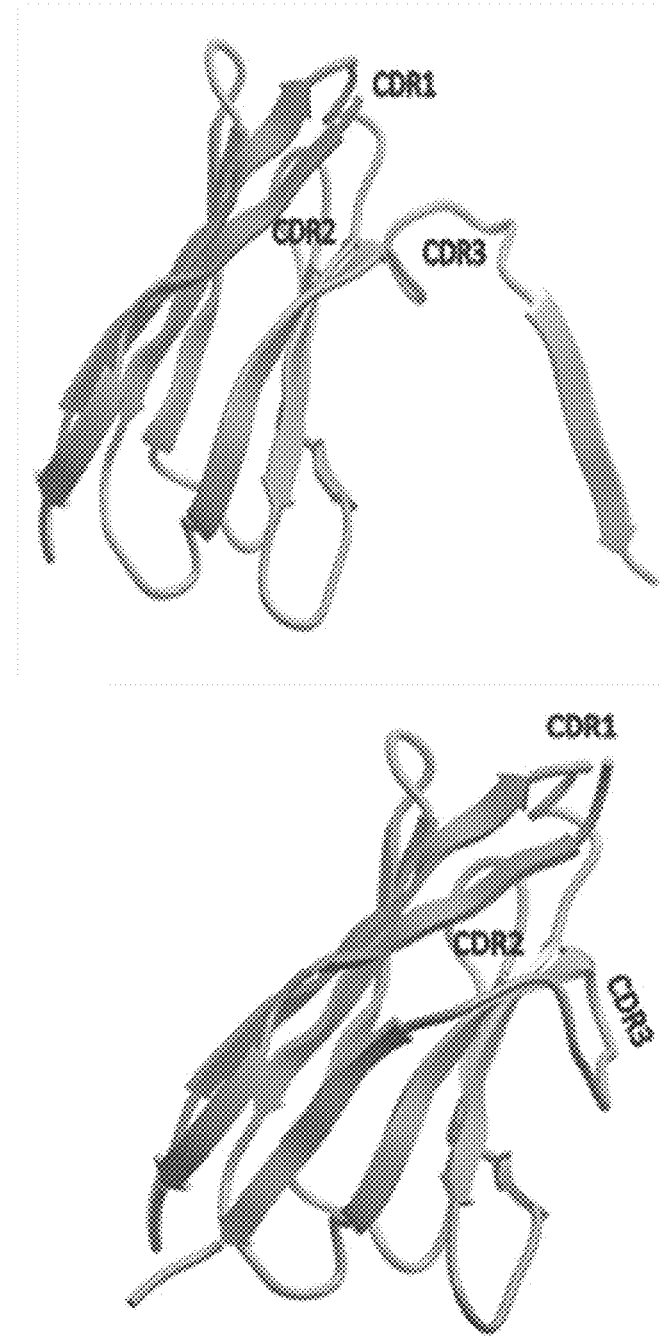
FIG. 14: Monomer of Polypeptide B as present in the dimer (top) and an isolated monomer of polypeptide B (bottom).
Figure 15:
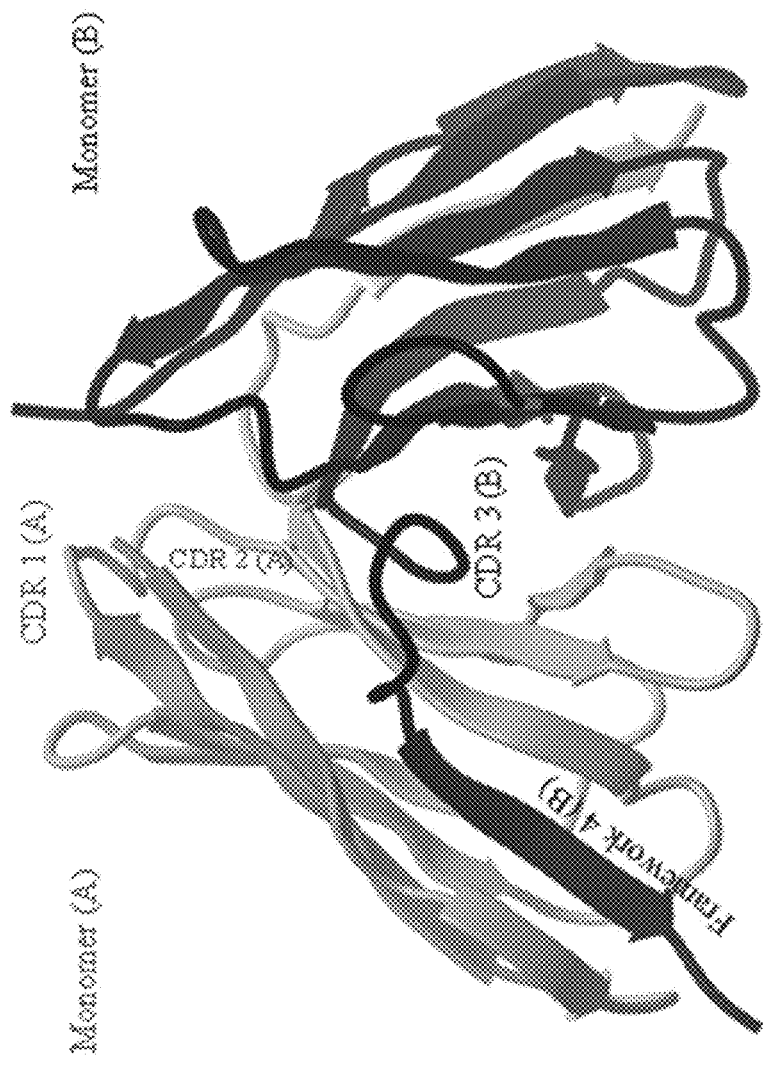
FIG. 15: Polypeptide B-dimer (an example of a NFD-Mo). Framework 4 of monomer A is replaced by framework 4 of monomer B and vice versa.
Figure 16:
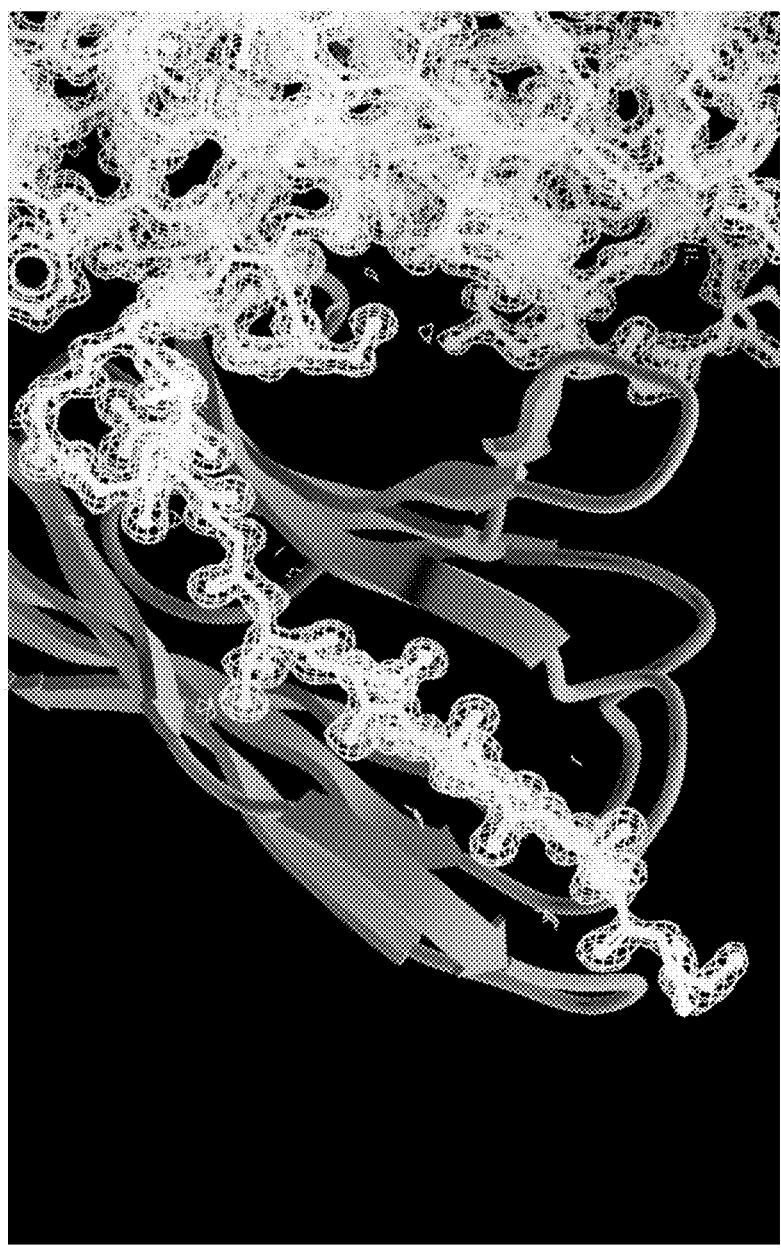
FIG. 16: Electron-density of monomer B in black. Monomer A is shown in grey ribbon.

The 2 polypeptide B-monomers that form the polypeptide B dimer (NFD-Mo) have a properly folded CDR1 and CDR2 and framework 1-3. The framework 4 residues (residues 103-113 according to the Kabat numbering scheme) are exchanged between the 2 monomers. This results in an unfolded CDR3 of both monomers that are present in the dimer (see FIG. 14). Dimer formation is mediated by the exchange of β-strand from Q105 to Ser113 between both monomers (see FIG. 15). Strand exchange is completely defined by electron density (see FIG. 16).

The residues of framework 1-3 and CDR1 and CDR2 of the monomer that form the dimer have a classical VHH fold and are almost perfectly superimposable on a correctly folded polypeptide B VHH domain (backbone rmsd<0.6 Å). A decreased stabilization of CDR3 in polypeptide B compared to the structures of VHH's with similar sequences to polypeptide B can be one of the causes of the framework 4 exchanged dimerization. A slightly modified form of polypeptide B with a Proline at position 45 shows a hydrogen-bond between Y91 and the main-chain of L98. This hydrogen-bond has a stabilizing effect on the CDR3 conformation.

Due to the leucine at position 45 in polypeptide B, the tyrosine 91 can not longer form the hydrogen-bond with the main-chain of leucine-98. This leads to a decreased stabilization of the CDR3 conformation in polypeptide B (FIG. 17).

Example 4.2

Figure 18:
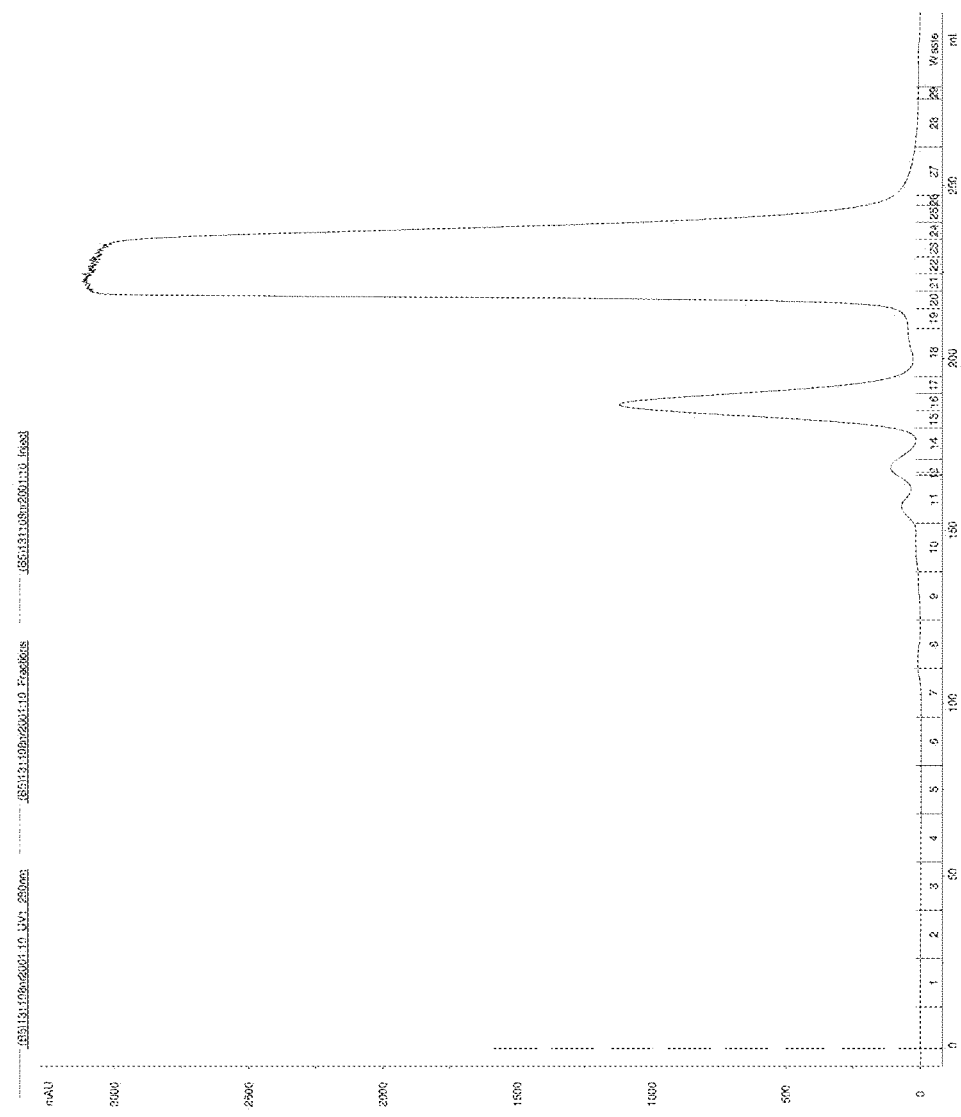
FIG. 18: Size exclusion chromatography of Polypeptide B material eluted from Protein A affinity column on Superdex 75 XK 26/60 column.
Figure 19:
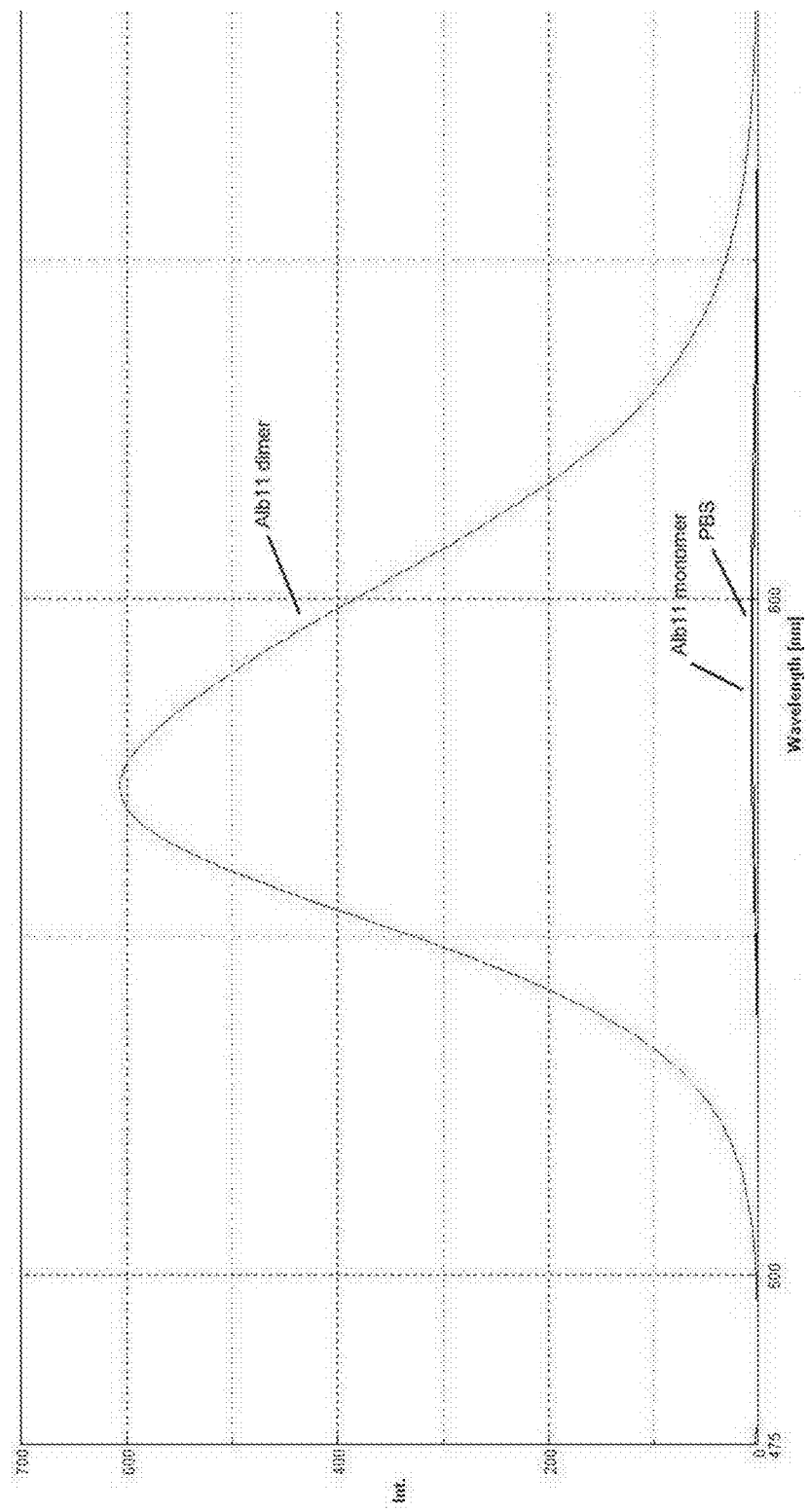
FIG. 19: Fluorescence emission Sypro orange in the presence of polypeptide B and polypeptide B-dimer.

Stability and Various Other Studies of the NFD with Polypeptide B 4.2.1 Production and Isolation of Polypeptide B Tagless polypeptide B was over-expressed in *E. coli* TOP10 strain at 28° C. after overnight induction with 1 mM IPTG. After harvesting, the cultures were centrifuged for 30 minutes at 4500 rpm and cell pellets were frozen at −20° C. Afterward the pellets were thawed and re-suspended in 50 mM phosphate buffer containing 300 mM NaCl and shaken for 2 hours at room temperature. The suspension was centrifuged at 4500 rpm for 60 minutes to clear the cell debris from the extract. The supernatant containing polypeptide B, was subsequently loaded on Poros MabCapture A column mounted on Akta chromatographic system. After washing the affinity column extensively with D-PBS, bound polypeptide B protein was eluted with 100 mM Glycine pH 2.7 buffer. Fractions eluted from column with acid were immediately neutralized by adding 1.5M TRIS pH8.5 buffer. At this stage the protein was already very pure as only a single band of the expected molecular weight was observed on Coomassie-stained SDS-PAGE gels. The fractions containing the polypeptide B were pooled and subsequently concentrated by ultrafiltration on a stirred cell with a polyethersulphone membrane with a cut-off of 5 kDa (Millipore). The concentrated protein solution was afterwards loaded on a Superdex 75 XK 26/60 column. On the chromatogram (see FIG. 18), besides the main peak eluting between 210 mL and 240 mL, a minor peak eluting between 180 mL and 195 ml was present.

Analysis on SDS-PAGE uncovered that both major peaks contain a single polypeptide with the same mobility (data not shown). This observation was the first indication that the peak eluting between 180 mL and 195 mL is a dimeric species, whereas the material eluting between 210 mL and 240 mL is a monomer. Further analysis on reversed phase chromatography and LC/MS of the dimeric and monomer species uncovered that both contain the same polypeptide with a molecular weight of about 12110 dalton. In this way from a 10 L fermentor run, in total 30 mg of the dimeric species and 1200 mg of the monomeric form of polypeptide B was isolated.

4.2.2 Antigen Binding Properties

The binding of the polypeptide B monomer and Polypeptide B dimer to human serum albumin was tested by surface plasmon resonance in a Biacore 3000 instrument. In these experiments human serum albumin was immobilized on CM5 chip via standard amine coupling method. The binding of both monomeric polypeptide B and dimeric polypeptide B at a concentration of 10 nanomolar were tested. Only for the monomer, binding was observed whereas no increase in signal was observed for the dimeric polypeptide B.

4.2.3 Difference in Physicochemical Properties Between Monomeric and Dimeric Polypeptide B The fluorescent dye Sypro orange (5000× Molecular Probes) can be used to monitor the thermal unfolding of proteins or to detect the presence of hydrophobic patches on proteins. In the experiment, monomeric and dimeric Polypeptide B at a concentration of 150 microgram/mL were mixed with Sypro orange (final concentration 10×). The solution was afterwards transferred to quartz, cuvette, and fluorescence spectra were recorded on A Jasco FP6500 instrument. Excitation was at 465 nm whereas the emission was monitored from 475 to 700 nm. As shown in FIG. 19, only a strong signal for the dimeric polypeptide B was observed, whereas no increase in fluorescence emission intensity was observed for the polypeptide B monomeric species. This observation strongly suggests that monomeric and dimeric forms of polypeptide B have a distinct conformation.

4.2.4 AUC-EQ—Sedimentation-Diffusion Equilibrium

Material and Methods

Experiments were performed with an Analytical ultracentrifuge XL-I from Beckman-Coulter using the interference optics of the instrument. Data were collected at a temperature of 20° C. and rotational speeds of 25000 rpm and 40000 rpm. 150 μL were filled in the sample sector of 12 mm two sector titanium centerpieces. Samples were diluted with standard PBS, which was also used for optical referencing. Attainment of apparent chemical and sedimentation equilibrium was verified by comparing consecutive scans until no change in concentration with time was observed. Data were evaluated with the model-independent M*-function and various explicit models using NONLIN. Standard values for the of the protein and the density of the solvent were used. Where appropriate, 95% confidence limits are given in brackets.

Result

Polypeptide B was found to have a molar mass of 11.92 kg/mole (11.86-11.97) kg/mole from a fit assuming a single, monodispere component. This agrees well with the result from the model-free analysis which is 12.25 kg/mole at zero concentration. Attempts to describe the data assuming self-association, non-ideality or polydispersity did not improve the global rmsd of the fit.

Polypeptide B was equally well-defined, having a molar mass of 23.06 kg/mole (22.56-23.44) kg/mole based on a direct fit assuming a single, monodispere component. The model-free analysis revealed a molar mass of 22.69 kg/mole. A small contribution from thermodynamic non-ideality improved the fit slightly but did not alter the molar mass. No evidence for a reversible self-association could be found.

The ratio of the M(Polypeptide B-dimer)/M(Polypeptide B) was 1.93. The small deviation from the expected factor of 2 can be explained by a different $\bar{v}$ of Polypeptide B Dimer compared to Polypeptide B, slight density differences for the different dilutions due to the slightly different Polypeptide B, slight density differences for the dilutions due to the slightly different buffers used (PBS for dilution and D-PBS for the stock solutions) and a contribution from non ideality too small to be reliably described with the data available.

4.2.5 Stability Study of Polypeptide F and Polypeptide B at 4° C., 25° C. and 37° C.

Solutions of monomeric polypeptide F and polypeptide B, formulated in D-PBS, were concentrated to 20 mg/mL and put on storage at 4° C., 25° C. and 37° C. After 3 and 6 weeks samples were analyzed by size exclusion chromatography on a Phenomenex BioSep SEC S-2000 column. In the SEC chromatograms of both polypeptide F and Polypeptide B, the presence of a pre-peak was only observed in the chromatograms of the samples stored at 37° C. The pre-peak corresponding to a dimer, was not observed in samples stored at 4° C., 25° C. or in a reference material stored at −20° C.

In the table 5 below the percentage of dimer present in the samples stored at 37° C. (expressed as percentage of area of dimer versus total area) for both polypeptide F and polypeptide B are compiled. As can be observed in this table, it appears that polypeptide B is more susceptible to dimer formation than polypeptide F.

TABLE 5

| Nanobody ® | % dimer-3 weeks | % dimer-6 weeks |
| --- | --- | --- |
| Polypeptide F | 3.1 | 5.8 |
| Polypeptide B | 20.9 | 37.1 |

In a separate experiment the effect of mannitol as excipient in the formulation buffer was evaluated. In this case monomeric polypeptide B was formulated at a protein concentration of 18 mg/mL respectively in D-PBS or D-PBS containing 5% mannitol. Samples were stored at 37° C. and analyzed by size exclusion chromatography on a Phenomenex BioSep SEC S-2000 column after 2, 4, 6 and 8 weeks.

In the table 6 below, the percentage of dimer present in the samples stored at 37° C. (expressed as percentage of area of dimer versus total area) for Polypeptide B stored in D-PBS and in D-PBS/5% mannitol were compiled. As shown in this table, the presence of mannitol in the buffer had a clear effect on the kinetics of dimer formation of polypeptide B at 37° C.

TABLE 6

| | % dimer after 2 weeks | % dimer after 4 weeks | % dimer after 6 weeks | % dimer after 8 weeks |
| --- | --- | --- | --- | --- |
| Polypeptide B | 13.5 | 22.1 | 30.0 | 41.8 |
| Polypeptide B with 5% mannitol | 5.3 | 11.7 | 16.8 | 23.7 |

In another experiment, solutions of both monomeric polypeptide F and polypeptide B at concentrations of 5 mg/ml, 10 mg/mL and 20 mg/mL in D-PBS were stored at 37° C. After 6 weeks, samples were analyzed by size exclusion chromatography on a Phenomenex BioSep SEC S-2000 column. In the table below the percentage of dimer present in the samples stored 37° C. (expressed as percentage of area of dimer versus total area) for polypeptide F and polypeptide B stored at 5 mg/mL, 10 mg/mL and 20 mg/mL are compiled. From this experiment we learned, as observed earlier, that dimer formation proceeds faster for the polypeptide B than for polypeptide F, but also that the kinetics of dimer formation are largely dependent on the protein concentration.

TABLE 7

| | % dimer (5 mg/mL) | % dimer (10 mg/mL) | % dimer (20 mg/mL) |
| --- | --- | --- | --- |
| Polypeptide F | 1.2 | 3.1 | 5.7 |
| Polypeptide B | 13.0 | 20.6 | 36.9 |

Similarly, dimer and possibly multimer formation was observed for polypeptides comprising polypeptide B and other single variable domains, e.g. polypeptides comprising one polypeptide B and 2 Nanobodies® binding to a therapeutic target (e.g. 2 identical Nanobody® directed against a therapeutic target). The dimer/multimer formation of said polypeptides comprising e.g. polypeptide B and other Nanobodies® could be slowed down or in some instances almost avoided if they were formulated in a mannitol containing liquid formulation.

Other polyols and/or sugars that are believed to be beneficial to reduce or avoid the formation of dimers (NFDs) and other possibly higher multimers are listed in Table 8. A wide variety of liquid formulations may be useful which may consist of or comprise any buffering agent, a biologically effective amount of polypeptide of the invention, a concentration of mannitol that is no greater than approximately 0.6M and other excipients including polyols, non-reducing sugars, NaCl or amino acids.

TABLE 8

| Polyols | sorbitol, mannitol, xylitol, ribitol, erythritol |
| --- | --- |
| Non-reducing sugars | sucrose, trehalose |

4.2.6 Chaotrope Induced Unfolding of Polypeptide B and Polypeptide B Dimer

Figure 20:
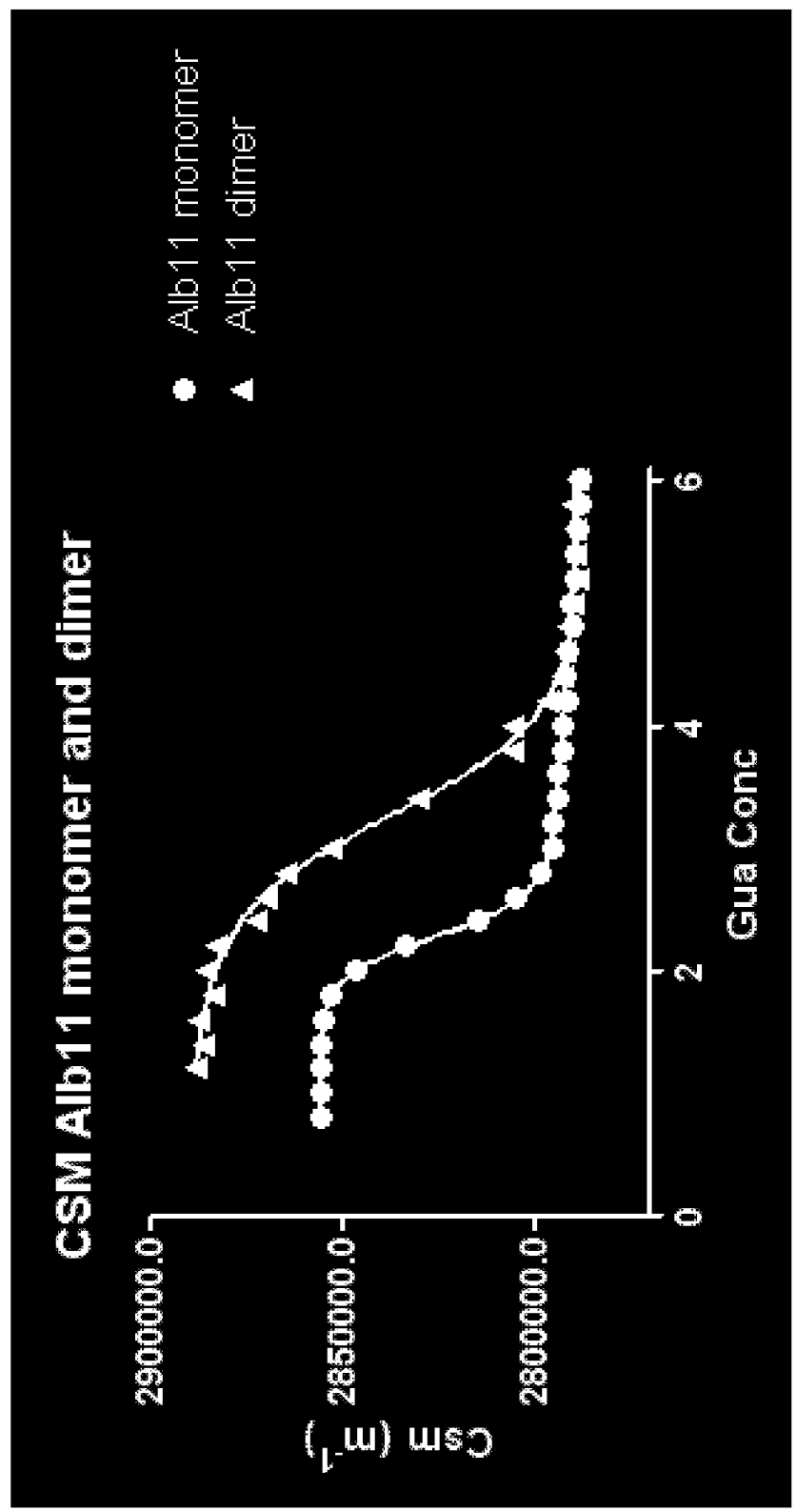
FIG. 20: Unfolding of Polypeptide B monomer and Polypeptide B-dimer in function of Guanidinium Hydrochloride concentration. Unfolding was monitored by intrinsic fluorescence measurements and thereby using center of spectral mass (CSM) as unfolding parameter.

Chaotrope induced unfolding is a technique frequently used to assess the stability of proteins. To monitor chaotrope induced unfolding intrinsic fluorescence of tryptophan or tyrosine residue can be used. As unfolding parameter the 'center of spectral mass' (CSM=Σ(fluorescence intensity×wavenumber)/(fluorescence intensity) can be used. Unfolding experiments with Polypeptide B monomer and Polypeptide B dimer were performed at 25 µg/mL in Guanidinium Hydrochloride solution in the concentration range 0-6M. After overnight incubation of these solutions fluorescence spectra were recorded using a Jasco FP-6500 instrument. Excitation was at 295 nm and spectra were recorded between 310 to 440 nm. Using the spectral data the CSM-value was calculated using the formula above. In the FIG. 20, the CSM as a function of Guanidinium Hydrochloride concentration is shown. As can be observed in FIG. 20, polypeptide B dimer unfolds at higher concentrations of Guanidinium Hydrochloride, and allows us to conclude that the monomer is less stable than the Polypeptide B-dimer.

Example 5

Further Characterization of a NFD with Polypeptide G and H

Figure 21:
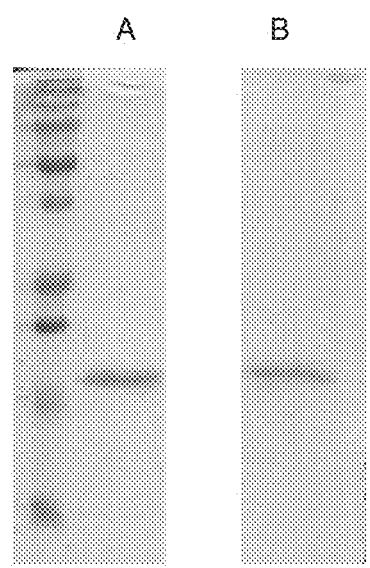
FIG. 21: Purity was analysed on a Coomassie stained gel (Panel A: Polypeptide G; Panel B: Polypeptide H).

Different mutants of polypeptide F have been constructed, expressed and purified. Sequence information is provided below. Purity was analysed on a Coomassie stained gel (FIG. 21) and western blot.

5.1 Binding to Serum Albumin in Biacore

Binding of Nanobodies® to human serum albumin (HSA) is characterized by surface plasmon resonance in a Biacore 3000 instrument, and an equilibrium constant $K_D$ was determined. In brief, HSA was covalently bound to CM5 sensor chips surface via amine coupling until an increase of 500 response units was reached. Remaining reactive groups were inactivated. Nanobody® binding was assessed using series of different concentrations. Each Nanobody® concentration was injected for 4 min at a flow rate of 45 µl/min to allow for binding to chip-bound antigen. Next, binding buffer without Nanobody® was sent over the chip at the same flow rate to allow dissociation of bound Nanobody®. After 15 minutes, remaining bound analyte was removed by injection of the regeneration solution (50 mM NaOH).

Figure 22:
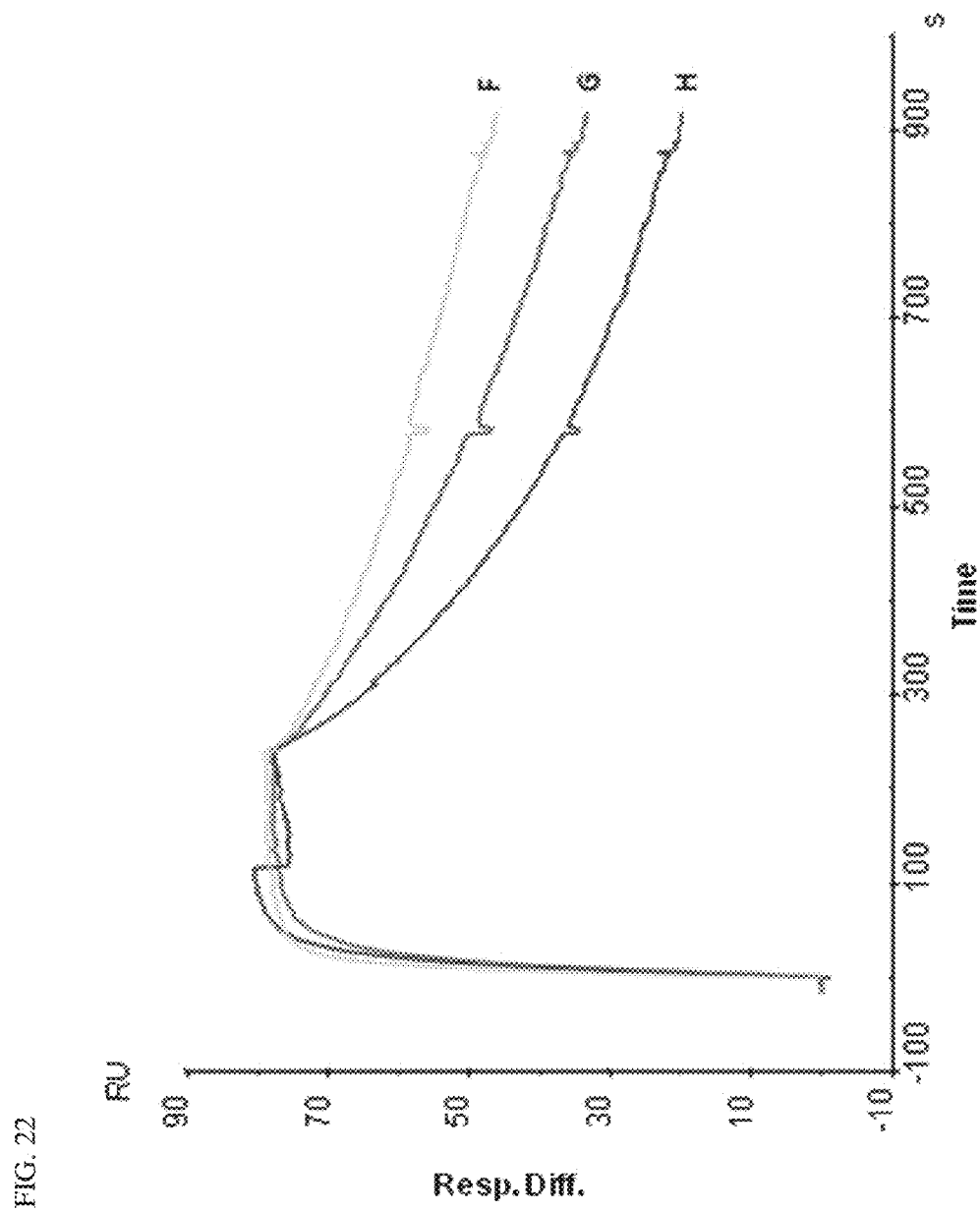
FIG. 22: Binding of polypeptide F, G, and H on HSA.

From the sensorgrams obtained (FIG. 22) for the different concentrations of each analyte. $K_D$ values were calculated via kinetic data analysis. Polypeptide H (with introduction of GL instead of EP, in particular P is replaced by L, see also FIG. 17 and examples above) had a greater koff rate.

TABLE 9

$k_{off}$ values of Polypeptide F and the humanized derivatives Polypeptide G and Polypeptide H as determined in Biacore for binding to HSA.

| Nanobody ® | $K_{off}$ (1/s) |
|---|---|
| Polypeptide F | 6.83 E−4 |
| Polypeptide G | 1.18 E−3 |
| Polypeptide H | 1.97 E−3 |

5.2 Stability on Storage

Solutions of monomeric Polypeptide 3 and Polypeptide H, formulated in D-PBS, are concentrated to 20 mg/mL and put on storage at 4° C., 25° C. and 37° C. After 3 and 6 weeks samples are analyzed by size exclusion chromatography on a Phenomenex BioSep SEC S-2000 column.

Example 6

Stability of the Polypeptide I in Different Buffers when Stored at 37° C. up to 10 Weeks Polypeptide I (SEQ ID NO: 11) is a trivalent bispecific Nanobody consisting of three humanized variable domains of a heavy-chain llama antibody, of which two identical subunits are specific for binding to RANKL, while the remaining subunit binds to HSA.

Polypeptide I was expressed in Pichia pastoris and purified on SP Sepharose as a capturing step and a Q filter as a polishing step or on SP Sepharose as a capturing step and Capto MMC as a polishing step or alternatively by using a ProtA capture step followed by and SP Sepharose polishing step. Concentration of the Polypeptide I and buffer switch to PBS, 10 mM phosphate+100 mM NaCl, 10 mM phosphate+10% mannitol or 10 mM phosphate+50 mM NaCl or others buffers was done via UF/DF or by dialysis. A final filtration on a 0.22 μm filter was performed. Polypeptide I was formulated in different buffers at ~60 mg/mL (buffers 1-12 given in Table 9).

TABLE 9

Overview of the different formulation buffers of Polypeptide I used in stability testing.

| Buffer | Concentration Polypeptide I (mg/mL) | Buffer | [NaCl] (mM) | Mannitol % (w:v) |
|---|---|---|---|---|
| 1 | 60 | 10 mM NaH$_2$PO$_4$•2H$_2$O, pH 7 | 50 | 0 |
| 2 | 60 | 10 mM NaH$_2$PO$_4$•2H$_2$O, pH 7 | 100 | 0 |
| 3 | 60 | 10 mM NaH$_2$PO$_4$•2H$_2$O, pH 7 | 0 | 10 |
| 4 | 59 | 10 mM Na-acetate, pH 5.5 | 50 | 0 |
| 5 | 59 | 10 mM Na-acetate, pH 5.5 | 100 | 0 |
| 6 | 59 | 10 mM Na-acetate, pH 5.5 | 0 | 10 |
| 7 | 60 | 20 mM L-histidine, pH 5.5 | 50 | 0 |
| 8 | 60 | 20 mM L-histidine, pH 5.5 | 100 | 0 |
| 9 | 60 | 20 mM L-histidine, pH 5.5 | 0 | 10 |
| 10 | 58 | 20 mM L-histidine, pH 6 | 50 | 0 |
| 11 | 58 | 20 mM L-histidine, pH 6 | 100 | 0 |
| 12 | 58 | 20 mM L-histidine, pH 6 | 0 | 10 |

The stability of the different samples was assessed in accelerated stress conditions at 37° C.±3° C. Samples were taken after 2, 3, 5 and 10 weeks storage at this temperature and were analyzed using SE-HPLC. Biacore was performed on the samples stored for 10 weeks to evaluate loss in potency.

6.1 SE-HPLC Analysis

The SE-HPLC assay consisted of a pre-packed silica gel TSKgel G2000SW$_{XL}$ column, a mobile phase consisting of KCl, NaCl and phosphate buffer pH 7.2 (D-PBS) and UV detection at 280 nm. The relative amount of specific protein impurity was expressed as area %, and was calculated by dividing the peak area corresponding to the specific protein or protein impurity by the total integrated area.

Figure 23:
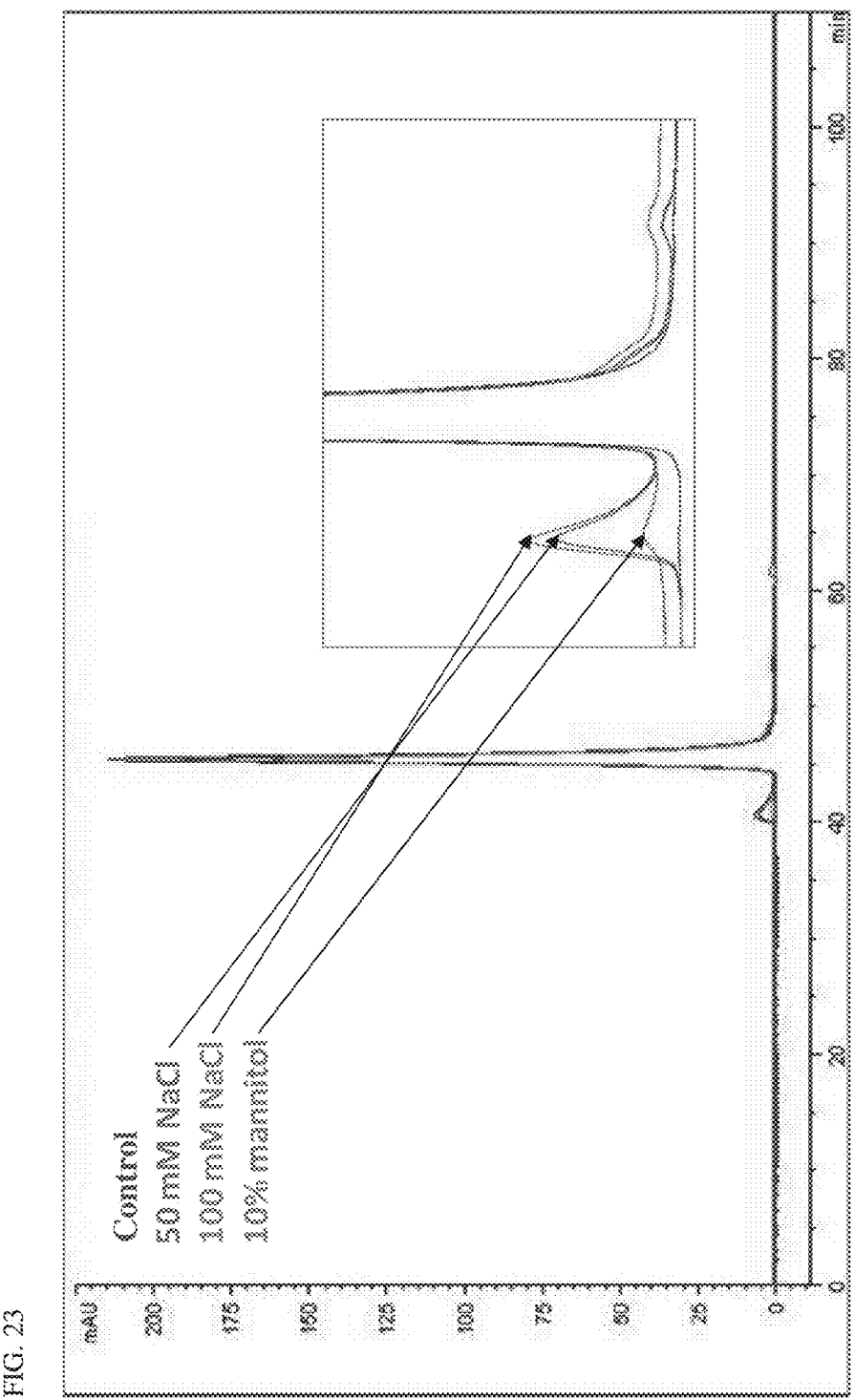
FIG. 23: The 280 nm SE-HPLC chromatograms of Polypeptide I formulated in phosphate buffer (2 weeks storage) with either 50 nM NaCl, 100 mM NaCl or 10% mannitol. A zoom on the main peak is shown as inset.

The results of the analysis of a sample by SE-HPLC is given in FIG. 23 where an example is shown for the sample stored during two weeks at 37° C. in the presence of 50 or 100 mM salt or 10% mannitol-containing phosphate buffer. Storage at 37° C. resulted in the formation of a clear prepeak eluting at about 40 minutes and some minor postpeaks close to the main peak; these postpeaks elute between 48-55 minutes (see insert in FIG. 23) and represent some degradation fragments. In Table 10 the integration data for all samples analysed is summarized for the different peaks observed (except buffer peaks after 60 minutes elution time).

TABLE 10

Integration data (% of total surface area) of the different peaks observed in the SE-HPLC chromatograms of Polypeptide I stored at 37° C. in different formulation buffers at all time points tested and in comparison with each control sample (each buffer).

| SE-HPLC | Sample | Phosphate pH 7 50 mM NaCl 60 mg/ml | Phosphate pH 7 100 mM NaCl 60 mg/ml | Phosphate pH 7 10% Mannitol 60 mg/ml | Acetate pH 5.5 50 mM NaCl 59 mg/ml | Acetate pH 5.5 100 mM NaCl 59 mg/ml | Acetate pH 5.5 10% Mannitol 59 mg/ml | Histidine pH 5.5 50 mM NaCl 60 mg/ml |
|---|---|---|---|---|---|---|---|---|
| % Prepeak | control | 0 | 0 | 0 | 0 | 0 | 0 | 0 |
|  | 2 w 37° C. | 5.6 | 6.9 | 1.3 | 4.6 | 6.3 | 2.3 | 5.5 |
|  | 3 w 37° C. | 4.4 | 6.2 | 0.65 | 3.9 | 5.9 | 0.18 | 5.6 |
|  | 5 w 37° C. | 13.7 | 15.8 | 3.9 | 11.5 | 14.2 | 1.22 | 14.0 |
|  | 10 w 37° C. | 23.8 | 25.3 | 11.1 | 21.0 | 23.9 | 3.4 | 27.2 |
| % Main peak | control | 100 | 100 | 100 | 100 | 100 | 100 | 100 |
|  | 2 w 37° C. | 93.5 | 92.2 | 97.9 | 94.8 | 93.1 | 98.8 | 94.0 |
|  | 3 w 37° C. | 93.7 | 92.0 | 95.2 | 95.0 | 92.8 | 96.9 | 93.4 |

TABLE 10-continued

Integration data (% of total surface area) of the different peaks observed in the SE-HPLC chromatograms of Polypeptide I stored at 37° C. in different formulation buffers at all time points tested and in comparison with each control sample (each buffer).

|  |  |  |  |  |  |  |  |  |
|---|---|---|---|---|---|---|---|---|
|  | 5 w 37° C. | 81.14 | 78.87 | 91.52 | 87.38 | 84.63 | 97.87 | 84.85 |
|  | 10 w 37° C. | 69.2 | 68.0 | 80.5 | 77.5 | 74.7 | 95.1 | 71.3 |
| % Postpeak 1 | control | 0 | 0 | 0 | 0 | 0 | 0 | 0 |
|  | 2 w 37° C. | 0 | 0 |  | 0 | 0 | 0 | 0 |
|  | 3 w 37° C. | 0 | 0 |  | 0 | 0 | 0 | 0 |
|  | 5 w 37° C. | 3.16 | 3.36 |  | 0 | 0 | 0 | 0 |
|  | 10 w 37° C. | 3.7 | 3.5 |  | 0 | 0 | 0 | 0 |
| % Postpeak 2 | control | 0 | 0 |  | 0 | 0 | 0 | 0 |
|  | 2 w 37° C. | 0.23 | 0.27 | 0.19 | 0.23 | 0.26 | 0.19 | 0.19 |
|  | 3 w 37° C. | 0.57 | 0.58 | 0.31 | 0.49 | 0.53 | 0.27 | 0.48 |
|  | 5 w 37° C. | 0.41 | 0.47 | 0.27 | 0.37 | 0.39 | 0.25 | 0.45 |
|  | 10 w 37° C. | 0.5 | 0.5 | 0.3 | 0.4 | 0.4 | 0.2 | 0.4 |
| % Postpeak 3 | control | 0 | 0 | 0 | 0 | 0 | 0 | 0 |
|  | 2 w 37° C. | 0.62 | 0.64 | 0.60 | 0.37 | 0.41 | 0.46 | 0.31 |
|  | 3 w 37° C. | 1.15 | 1.25 | 1.07 | 0.52 | 0.64 | 0.61 | 0.49 |
|  | 5 w 37° C. | 1.59 | 1.50 | 1.49 | 0.75 | 0.78 | 0.66 | 0.70 |
|  | 10 w 37° C. | 2.7 | 2.6 | 3.1 | 1.1 | 1.0 | 1.3 | 1.1 |

| SE-HPLC | Sample | Histidine pH 5.5 100 mM NaCl 60 mg/ml | Histidine pH 5.5 10% Mannitol 60 mg/ml | Histidine pH 6 50 mM NaCl 58 mg/ml | Histidine pH 6 100 mM NaCl 58 mg/ml | Histidine pH 6 10% Mannitol 58 mg/ml |
|---|---|---|---|---|---|---|
| % Prepeak | control | 0 | 0 | 0 | 0 | 0 |
|  | 2 w 37° C. | 7.5 | 0.54 | 6.3 | 7.7 | 0.63 |
|  | 3 w 37° C. | 7.9 | 0.34 | 7.0 | 8.6 | 0.39 |
|  | 5 w 37° C. | 17.1 | 1.5 | 16.2 | 17.4 | 2.0 |
|  | 10 w 37° C. | 27.8 | 5.4 | 26.8 | 27.0 | 7.3 |
| % Main peak | control | 100 | 100* | 100 | 100 | 100* |
|  | 2 w 37° C. | 92.1 | 98.8 | 93.1 | 91.5 | 96.7 |
|  | 3 w 37° C. | 91.5 | 98.6 | 91.3 | 90.2 | 98.8 |
|  | 5 w 37° C. | 81.73 | 97.49 | 82.22 | 81.19 | 96.76 |
|  | 10 w 37° C. | 73.5 | 93.1 | 71.3 | 71.2 | 91.0 |
| % Postpeak 1 | control | 0 | 0 | 0 | 0 | 0 |
|  | 2 w 37° C. | 0 | 0 | 0 | 0 | 0 |
|  | 3 w 37° C. | 0 | 0 | 0 | 0 | 0 |
|  | 5 w 37° C. | 0 | 0 | 0 | 0 | 0 |
|  | 10w 37° C. | 0 | 0 | 0 | 0 | 0 |
| % Postpeak 2 | control | 0 | 0 | 0 | 0 | 0 |
|  | 2 w 37° C. | 0.17 | 0.19 | 0.20 | 0.23 | 0.18 |
|  | 3 w 37° C. | 0.55 | 0.27 | 0.54 | 0.5 | 0.27 |
|  | 5 w 37° C. | 0.29 | 0.23 | 0.52 | 0.42 | 0.37 |
|  | 10 w 37° C. | 0.5 | 0.2 | 0.4 | 0.4 | 0.3 |
| % Postpeak 3 | control | 0 | 0 | 0 | 0 | 0 |
|  | 2 w 37° C. | 0.26 | 0.37 | 0.40 | 0.58 | 0.53 |
|  | 3 w 37° C. | 0.55 | 0.57 | 1.12 | 0.71 | 0.56 |
|  | 5 w 37° C. | 0.88 | 0.78 | 1.06 | 0.99 | 0.87 |
|  | 10 w 37° C. | 1.3 | 1.3 | 1.5 | 1.4 | 1.5 |

The peak area of the prepeak increased over time but was reduced by the addition of mannitol to the buffer (Table 10). The postpeaks between 48-55 minutes elution time corresponded to degradation products (due to remaining proteolytic activity in sample). The relative area (%) of these peaks increased only slightly, implying that degradation was restricted to a minimum.

Figure 24A:
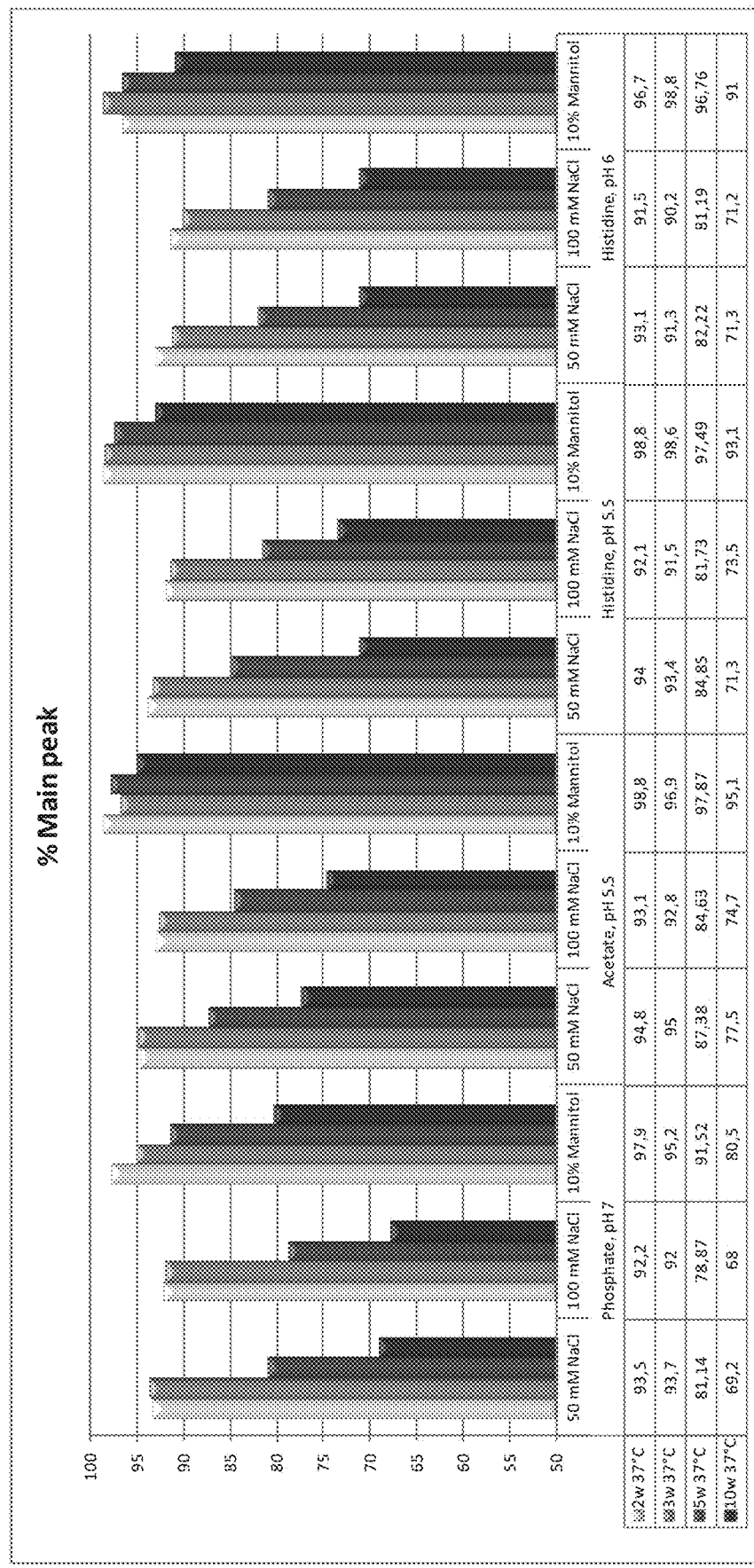
FIGS. 24A-24B: Figure demonstrating the time-dependent decrease (FIG. 24A) and increase (FIG. 24B) of the surface area of, respectively, the main peak and % dimers observed in SE-HPLC analysis of Polypeptide I formulated in different buffers and stored for 10 weeks at 37° C.
Figure 24B:
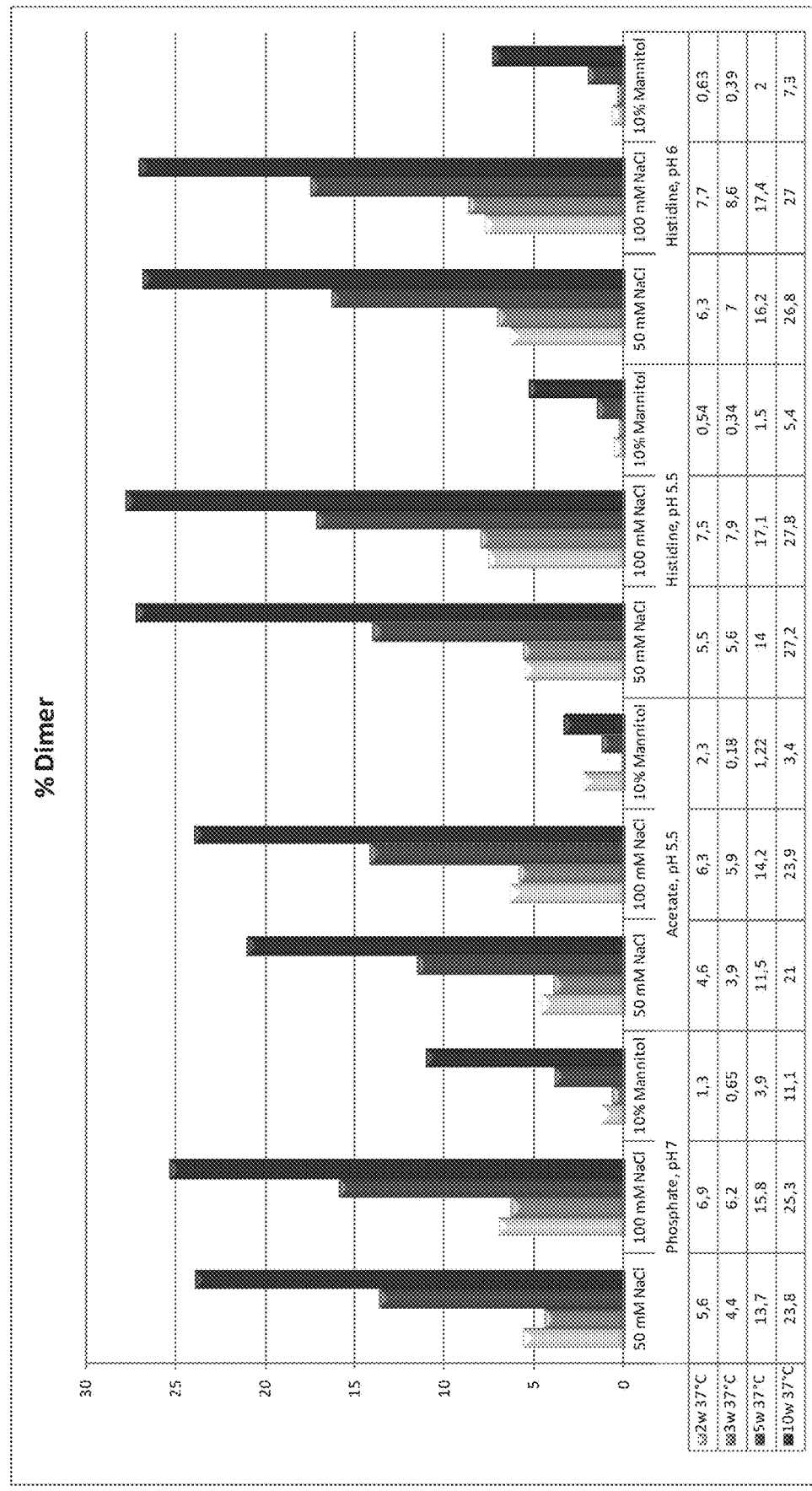
Figure 25:
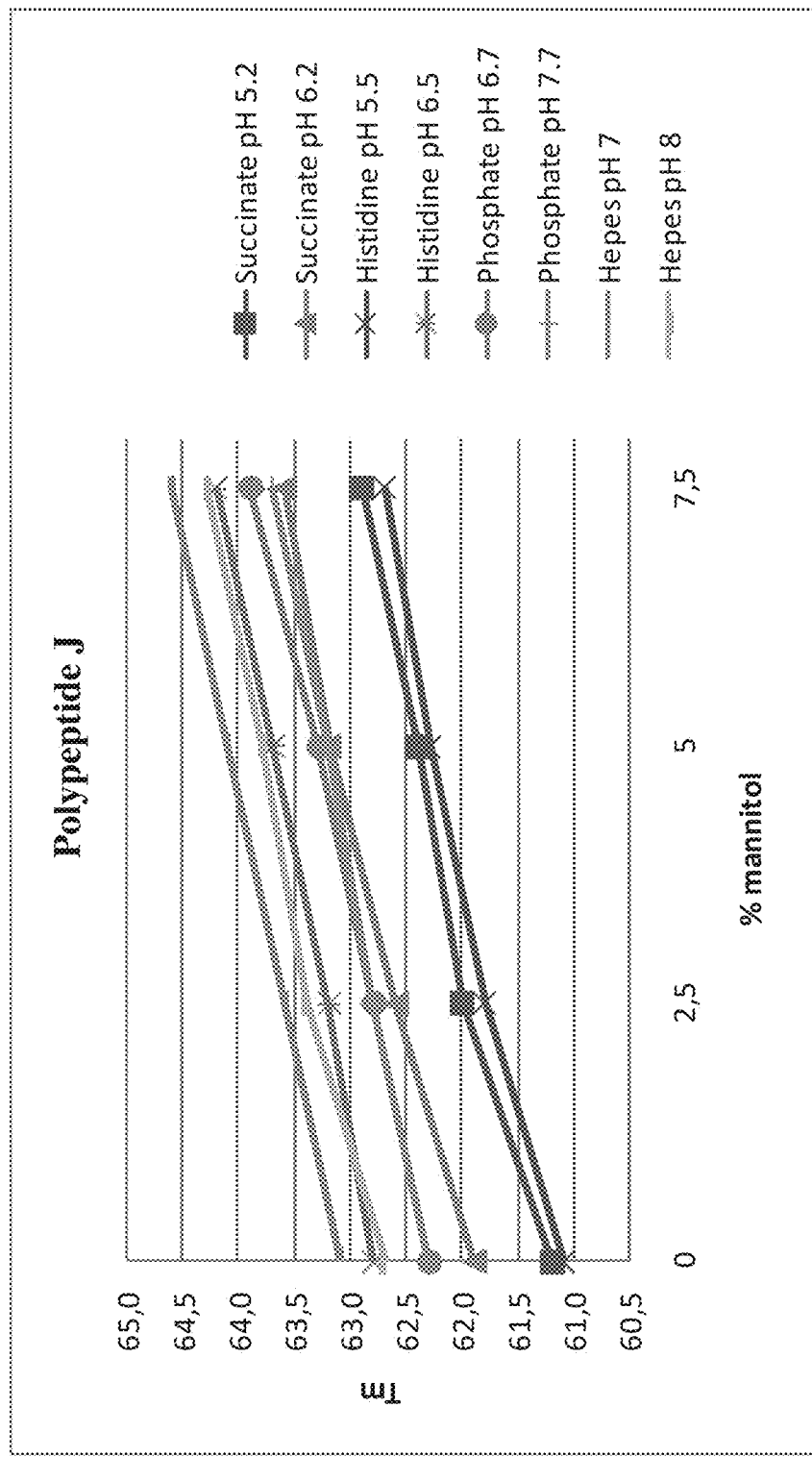
FIG. 25: Overview of the results obtained for thermal stability testing of Polypeptide J.
Figure 26:
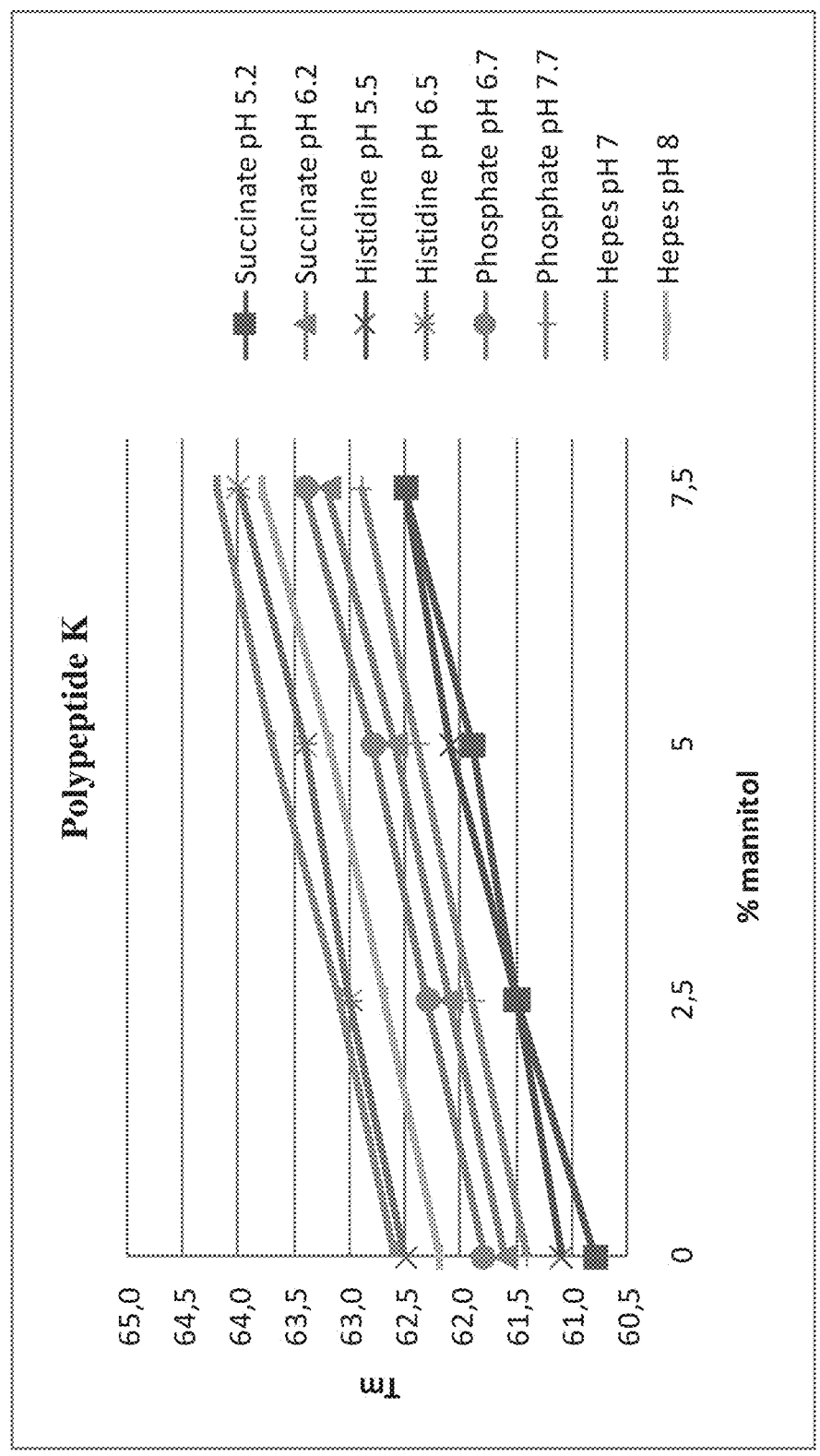
FIG. 26: Overview of the results obtained for thermal stability testing of Polypeptide K.
Figure 27:
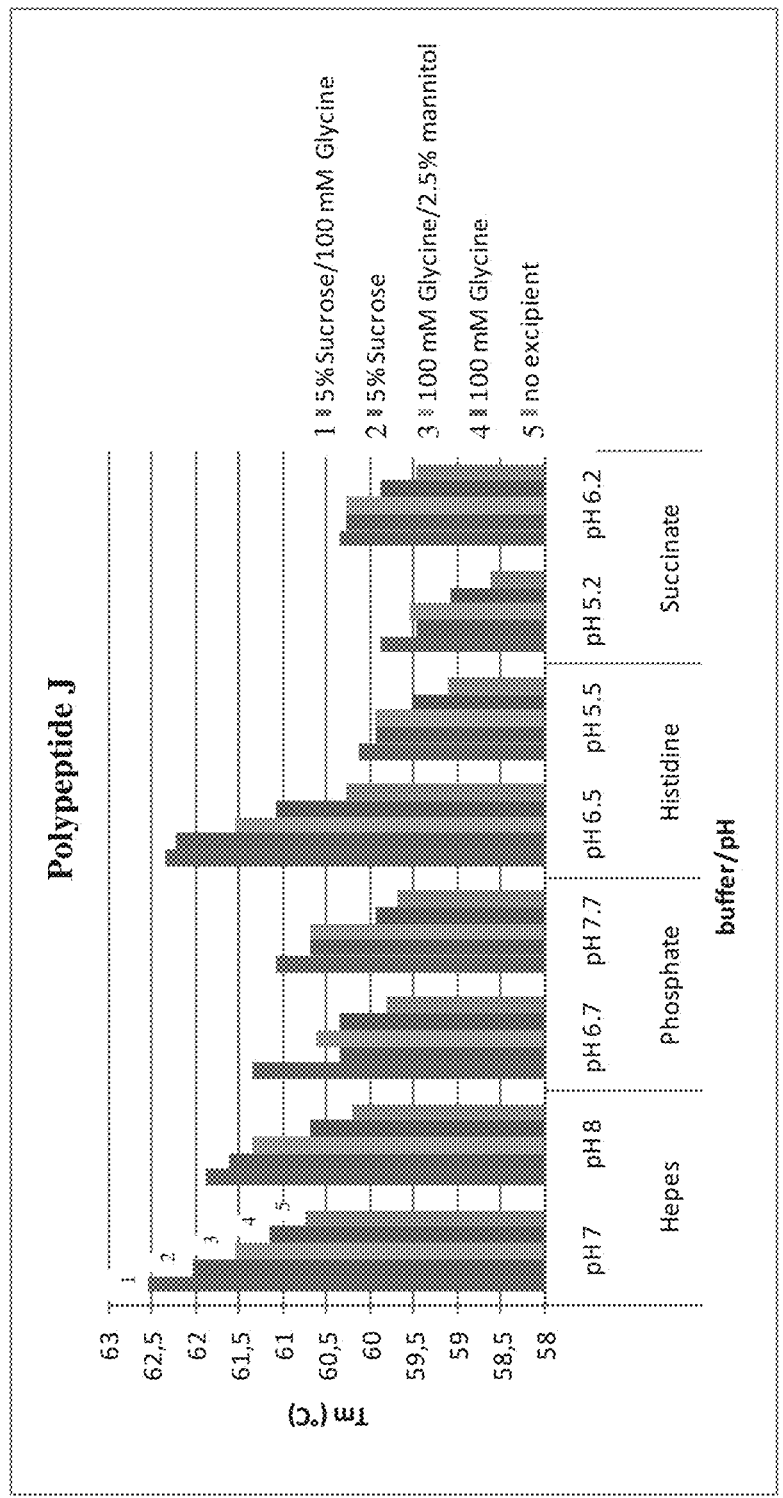
FIG. 27: Overview of the results obtained for thermal stability testing of Polypeptide J.
Figure 28:
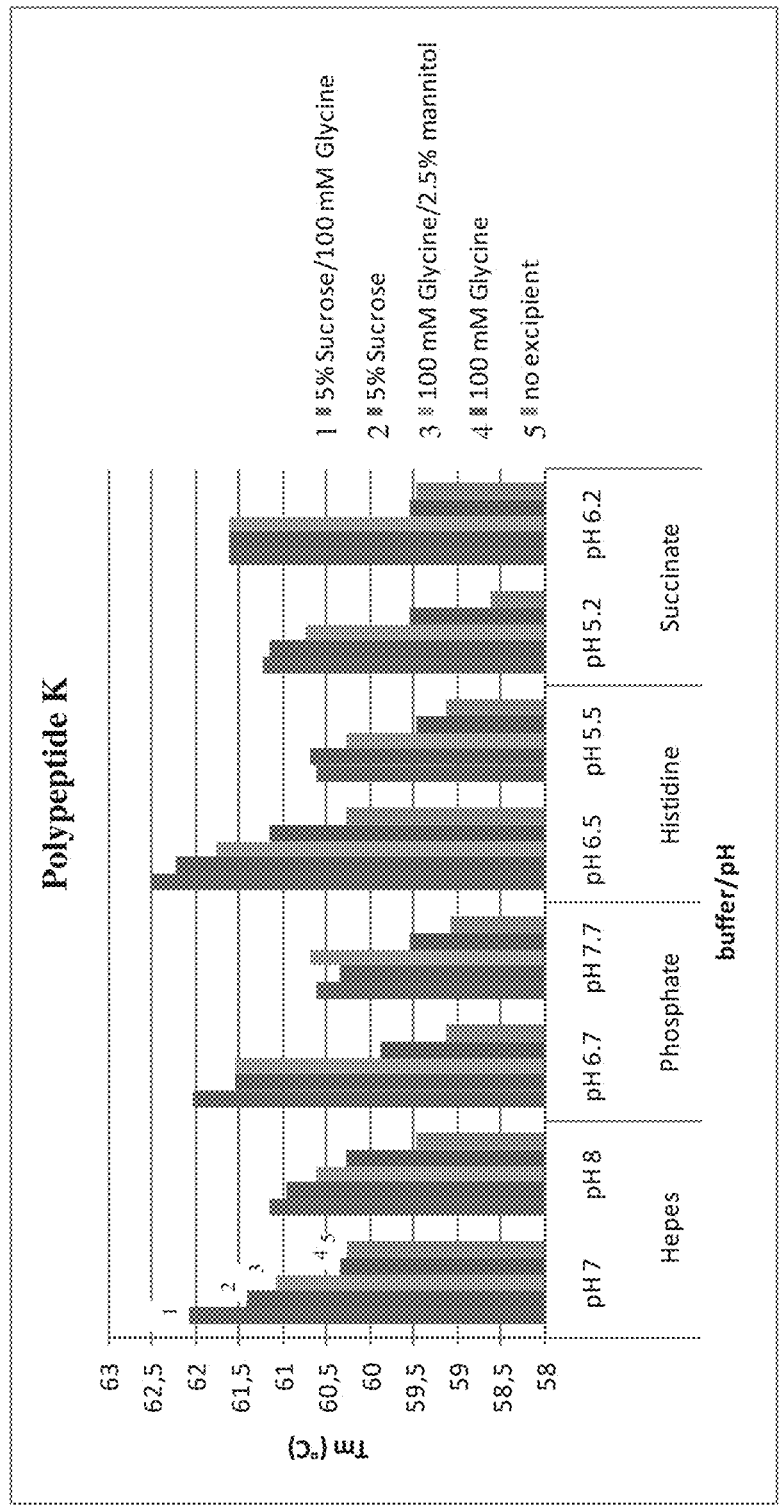
FIG. 28: Overview of the results obtained for thermal stability testing of Polypeptide K.
Figure 29:
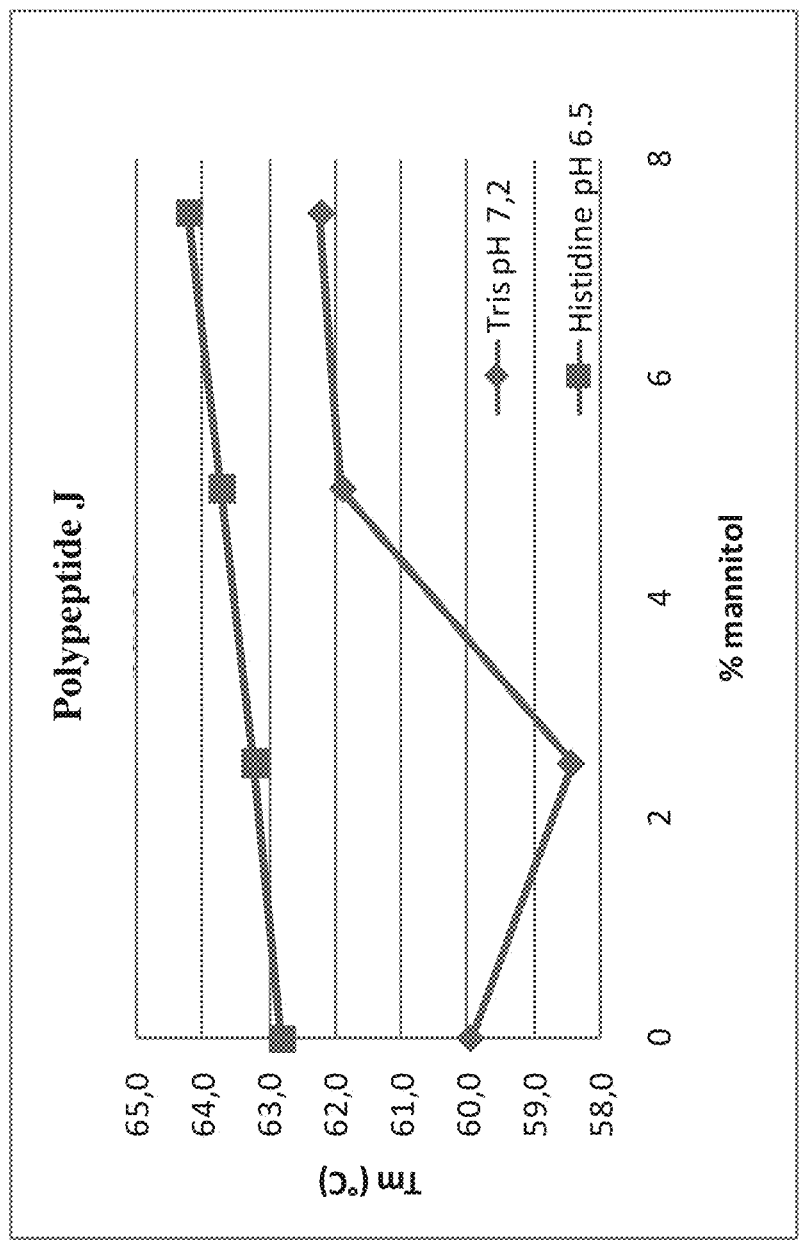
FIG. 29: Overview of the results obtained in thermal stability testing of Polypeptide in Tris buffer pH 7.2 or Histidine pH 6.5, with sucrose, glycine or mannitol added as excipient.

The prepeak represented the dimeric form of Polypeptide I. The peak surface area of the prepeak increased with storage time (Table 10) and was accompanied by a concomitant decrease in surface area of the main peak (Table 10). The propensity to form dimers was significantly lower in the formulations containing 10% mannitol, which seemed to have a positive effect in suppressing the dimerization process. Note the significant lower amounts of dimers observed in the Acetate and Histidine buffers (pH 5.5) containing 10% mannitol (Table 10 and FIGS. 24A-24B). FIG. 24A summarizes the % surface area for the main peak in the different buffers and at different time points when stored at 37° C. FIG. 24B summarizes the data for the % prepeak (dimer).

6.2 Biacore Potency Analysis of the Polypeptide I Stored at 37° C.

The RANKL and HSA binding of Polypeptide I in stability samples stored for 10 weeks at 37° C. was compared with the activity of the unstressed reference batch using Biacore analysis. RANKL or HSA was immobilized on the Biacore chip (amine coupling using the Biacore amine coupling kit). After a preconditioning step of 5 injections of Polypeptide I, all samples were diluted to 2.5 nM in triplicate and analyzed on the chip. Slopes were determined using the general fit method and the linear fit model (BIAevaluation software). To determine the initial binding rate (IBR), the slope between 5 s and 30 s was selected. The values of these slopes were transferred in excel and the percentage activity/potency compared to the Polypeptide II reference material was determined. Biacore potency is thus expressed as relative potency compared to the reference materials. The relative potencies are given in Table 11 and are expressed as % activity compared to reference batch.

After 10 weeks of storage at 37° C. the relative potency of Polypeptide I for binding RANKL had dropped to 70-80% in the different buffers (Table 11). In histidine, pH 6+10% mannitol, the activity remained the highest (87.4%). The higher the NaCl concentration in the buffer, the lower the relative potency in the sample (compare the values obtained in buffers with 50 mM NaCl and 1.00 nM NaCl in Table 11).

TABLE 11

Relative potencies of the HSA and RANKL binding moieties of Polypeptide I after 10 weeks at 37° C. as measured by Biacore analysis.

| | Relative potency | |
|---|---|---|
| Buffer | RANKL | HSA |
| Phosphate + 50 mM NaCl, pH 7 | 81.0 | 57.4 |
| Phosphate + 100 mM NaCl, pH 7 | 78.6 | 56.6 |
| Phosphate + 10% Mannitol, pH 7 | 76.3 | 66.8 |
| Acetate + 50 mM NaCl, pH 5.5 | 80.1 | 63.0 |
| Acetate + 100 mM NaCl, pH 5.5 | 78.0 | 59.0 |
| Acetate + 10% Mannitol, pH 5.5 | 80.9 | 79.4 |
| Histidine + 50 mM NaCl, pH 5.5 | 80.2 | 59.7 |
| Histidine + 100 mM NaCl, pH 5.5 | 73.1 | 55.0 |
| Histidine + 10% Mannitol, pH 5.5 | 75.2 | 73.6 |
| Histidine + 50 mM NaCl, pH 6 | 79.1 | 59.3 |
| Histidine + 100 mM NaCl, pH 6 | 78.3 | 57.5 |
| Histidine + 10% Mannitol, pH 6 | 87.4 | 83.4 |

The relative potency for HSA binding had dropped more compared to the activity for RANKL binding after 10 weeks storage at 37° C. This decrease in activity however was less significant in the mannitol-containing buffers than in the NaCl-containing buffers. As observed for RANKL binding, the percentage activity on HSA decreased with increasing concentrations of NaCl in the different buffers.

Example 7

Tm Determination of Polypeptides J and K

Polypeptide J (SEQ ID NO: 12) is a bispecific Nanobody consisting of two humanized variable domains of a heavy-chain llama antibody, one binding to IL-6R, the other one (Alb11) binding to HSA. The trivalent bispecific Polypeptide K (SEQ ID NO: 13) consists of two identical subunits that are specific for IL-6R while the third subunit binds to HSA.

The polypeptides were expressed in *Pichia pastoris*. Concentration of the polypeptide and buffer switch to PBS or other formulation buffer was done via UF/DF (Sartorius Hydrosart Sartocon Slice 200, 10 kDa) or dialysis. A final filtration was carried out at 0.22 μm.

The melting temperature (Tm) in different buffers was determined using the fluorescence-based thermal shift assay. The thermal shift assay or TSA can be performed in 96-well plate in a Q-PCR device to evaluate the effect of buffer couple, ionic strength, pH and excipients on the thermal stability of proteins. The assay results in a Tm value that is indicative for the thermal stability in the tested buffers. Briefly, the assay follows the signal changes of a fluorescence dye, such as Sypro Orange, while the protein undergoes thermal unfolding. When Sypro Orange is added to a properly folded protein solution, it is exposed in an aqueous environment and its fluorescence signal is quenched. When the temperature rises, the protein undergoes thermal unfolding and exposes its hydrophobic core region. Sypro Orange then binds to the hydrophobic regions, unquenches which results in the increase of the fluorescence signal.

The Tm was assessed for Polypeptide J and Polypeptide K in different buffers, excipients and combinations thereof using the TSA assay. The obtained Tm values are displayed graphically in FIG. 25, FIG. 26, FIG. 27, FIG. 28, and FIG. 29. In all conditions tested, the Tm values were slightly higher for Polypeptide J than Polypeptide K. The excipients tested (mannitol, sucrose and glycine) had a similar effect on the Tm values of Polypeptide J and Polypeptide K. All excipients tested appeared to have a stabilizing effect on Polypeptide J and Polypeptide K, since the melting temperatures increased with increasing excipient concentration. The highest Tm values were obtained in buffers containing 7.5% mannitol or 5% sucrose.

Example 8

Storage Stability Study of Polypeptides J and K at 37° C.

An initial storage stability study was performed to get a general understanding of the stability of Polypeptides J, K and L and to determine if adding mannitol in the formulation buffer has a beneficial effect in minimizing the formation of potential dimers, as was observed for Polypeptide I (see Example 6). The trivalent bispecific Polypeptide L (SEQ ID NO: 14) consists of two identical subunits that are specific for IL-6R while the third subunit binds to HSA.

The three Polypeptides were formulated in different buffers (Table 12) at a concentration of 10 mg/mL (Polypeptide J), 7.1 mg/mL (Polypeptide K) and 10.3 mg/mL (Polypeptide L).

TABLE 12

Overview of the different formulation buffers used in initial stability testing of Polypeptide J, Polypeptide K and Polypeptide L.

| Condition | Buffer | [NaCl] | Mannitol |
|---|---|---|---|
| 1 | PBS | 0 mM | 0% |
| 2 | PBS | 0 mM | 5% |
| 3 | 10 mM NaH$_2$PO$_4$•2H$_2$O, pH | 100 mM | 0% |
| 4 | 10 mM NaH$_2$PO$_4$•2H$_2$O, pH | 100 mM | 5% |
| 5 | 10 mM Na-acetate, pH 5.5 | 100 mM | 0% |
| 6 | 10 mM Na-acetate, pH 5.5 | 100 mM | 5% |
| 7 | 20 mM L-histidine, pH 6 | 100 mM | 0% |
| 8 | 20 mM L-histidine, pH 6 | 100 mM | 5% |

The stability of the different samples was assessed in accelerated stress conditions at 37° C. Samples were analyzed after 1 week using SE-HPLC. Selected samples of Polypeptides J and K were also analyzed after 3 weeks of storage. The SE-HPLC assay consisted of a pre-packed Phenomenex BioSep SEC S2000 column, a mobile phase consisting of KCl, NaCl and phosphate buffer pH 7.2 (D-PBS) and UV detection at 280 nm. The relative amount of specific protein impurity was expressed as area %, and was calculated by dividing the peak area corresponding to the specific protein or protein impurity by the total integrated area. The method can resolve and quantify the relative amounts of intact material and product related impurities such as aggregates and degradation fragments.

For both Polypeptides, prolonged storage at 37° C. resulted in the formation of prepeaks and some minor postpeaks. The postpeaks probably corresponded to degradation products (due to remaining proteolytic activity in sample). The surface area of these postpeaks remained very low, suggesting only minimal degradation after 3 weeks at 37° C.

Figure 30:
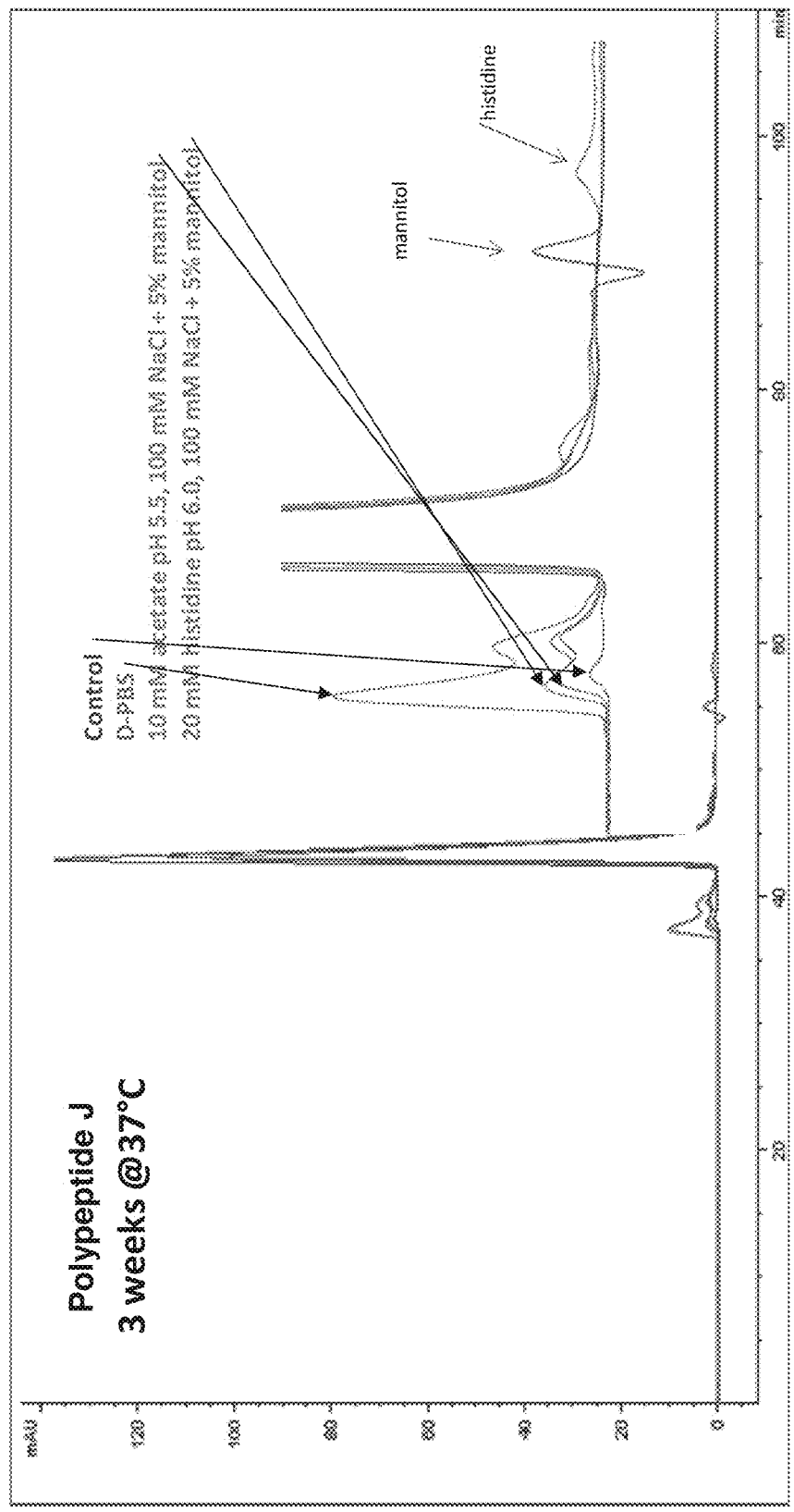
FIG. 30: Overlay of the SE-HPLC chromatograms of IL6R304 formulated at 10 mg/mL stored for 3 weeks at 37° C. Inset, zoom on the main peak to demonstrate the buffer-dependent differences in % aggregates.
Figure 31:
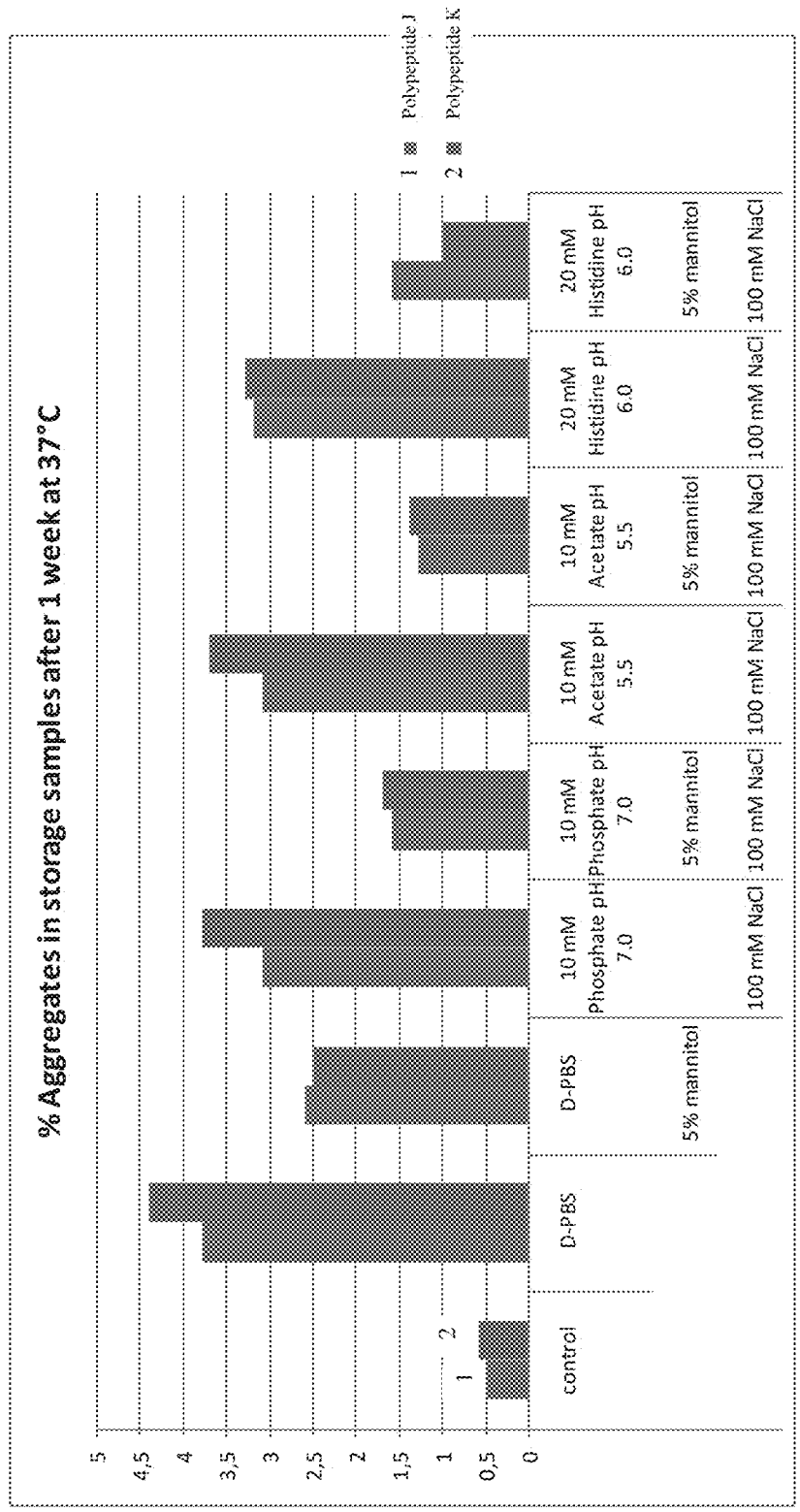
FIG. 31: Figure demonstrating the buffer-dependent differences in % aggregates (peak surface area in SE-HPLC) that were observed in the stability samples of Polypeptide J and Polypeptide K stored for 1 week at 37° C.

Both Polypeptides had a strong tendency to form dimers/oligomers (aggregates), which were visible as prepeak(s) in the chromatograms of the SE-HPLC analysis. An example chromatogram is shown in FIG. 30. The peak area of the prepeak increased significantly over time (represented as % aggregates in FIG. 31) and was accompanied by a concomitant decrease in surface area of the main peak. The lowest amounts of oligomers were observed in the mannitol-containing formulations.

Example 9

Storage Stability Study of Polypeptide J at 5° C. and 37° C.

An overview of the different formulation buffers and methods used in stability testing of Polypeptide J is given in Table 13 and Table 14, respectively.

TABLE 13

Overview of the different formulation buffers used in stability testing of Polypeptide J.

| Buffer | Concentration Polypeptide J | Buffer | % Tween 80 | % Mannitol | % Sucrose | mM Glycine |
|---|---|---|---|---|---|---|
| 1 | 10 mg/mL | 20 mM L-histidine pH 6.5 | / | / | / | / |
| 2 | 10 mg/mL | 20 mM L-histidine pH 6.5 | 0.01 | / | / | / |
| 3 | 10 mg/mL | 20 mM L-histidine pH 6.5 | 0.05 | / | / | / |
| 4 | 10 mg/mL | 20 mM L-histidine pH 6.5 | 0.05 | 5 | / | / |
| 5 | 10 mg/mL | 20 mM L-histidine pH 6.5 | 0.05 | 5 | / | 200 |
| 6 | 10 mg/mL | 20 mM L-histidine pH 6.5 | 0.05 | 2.5 | / | 100 |
| 7 | 10 mg/mL | 20 mM L-histidine pH 6.5 | 0.05 | / | 10 | / |
| 8 | 10 mg/mL | 20 mM L-histidine pH 6.5 | 0.05 | / | / | 200 |
| 9 | 10 mg/mL | 20 mM L-histidine pH 6.5 | 0.05 | / | 5 | 100 |
| 10 | 10 mg/mL | 20 mM L-histidine pH 6.5 | 0.05 | 2.5 | 5 | / |
| 11 | 10 mg/mL | 20 mM L-histidine pH 6.5 | / | 2.5 | 5 | 100 |
| 12 | 10 mg/mL | 20 mM L-histidine pH 6.5 | 0.05 | 2.5 | 5 | 100 |

TABLE 14

Methods used for assessing the stability of Polypeptide J at different time points (represented as x weeks or w) after storage at 5° C. and 37° C.

| Method | Purpose | Ref. material | Stress condition 5° C. | Stress condition 37° C. |
|---|---|---|---|---|
| A280 | Content | 0w | 1, 2 and 5w | 1, 2, 3 and 5w |
| Appearance | Precipitation | 0w | 1, 2 and 5w | 1, 2, 3 and 5w |
| RPC | Purity/variants | 0w | 1, 2 and 5w | 1, 2, 3 and 5w |
| SEC | Purity/aggregation/hydrolysis | 0w | 1, 2 and 5w 6 months | 1, 2, 3 and 5w 6 months |
| Biacore | Potency (HSA binding) | 0w | 5w | 5w |
| Osmolality | Characteristic | 0w | / | / |

Samples of the reference material (0 weeks) and samples stored for up to 6 months at 5° C. and 37° C. were analyzed using SE-HPLC. No differences were observed between the SE-HPLC profiles of the reference samples (at 0 weeks) and the samples stored for up to 5 weeks at 5° C. SE-HPLC analysis of die samples stored for 6 months at 5° C. did not show increase in area % of the prepeaks, meaning that no oligomers were formed under these storage conditions, not even in the formulation containing only 20 mM L-histidine, pH 6.5 i.e. without Tween-80 or any excipient (data not shown).

Prolonged storage at 37° C. resulted in the formation of prepeaks and some minor postpeaks. The postpeaks probably corresponded to degradation products (due to remaining proteolytic activity in sample). The relative area (%) of these peaks increased only slightly, implying that degradation was restricted to a minimum. The other peaks visible in the chromatograms were background peaks arising from the buffer components.

Figure 32:
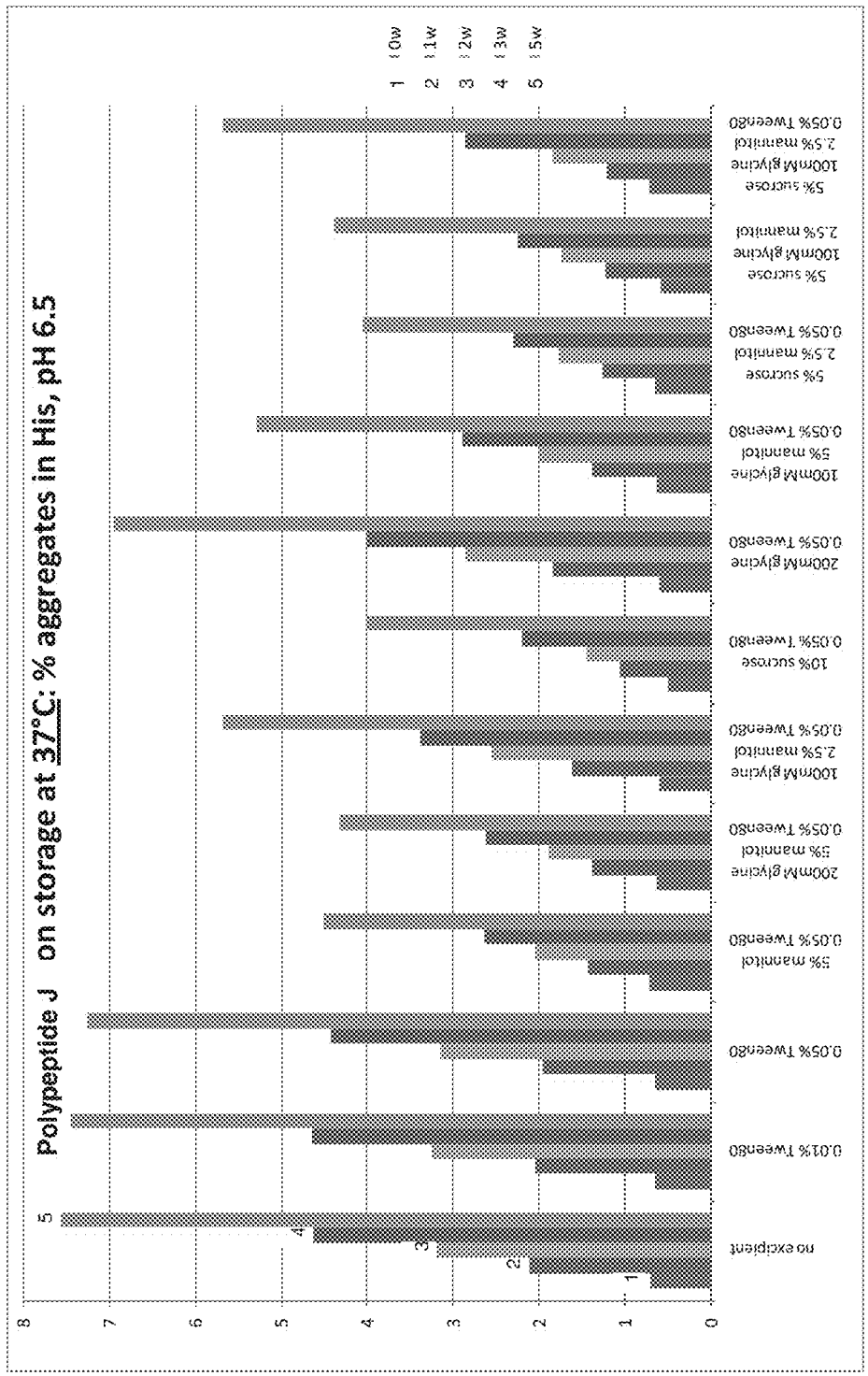
FIG. 32: Figure demonstrating the time-dependent increase of the % oligomers/aggregates (Y-axis) observed in SE-HPLC analysis of Polypeptide J stored for up to 5 weeks at 37° C. (A) in the buffers indicated in the graph. The % oligomers/aggregates is expressed as the sum of the % peak surface areas of prepeak 1a, prepeak 1b and prepeak 2 relative to the total peak surface area.
Figure 33:
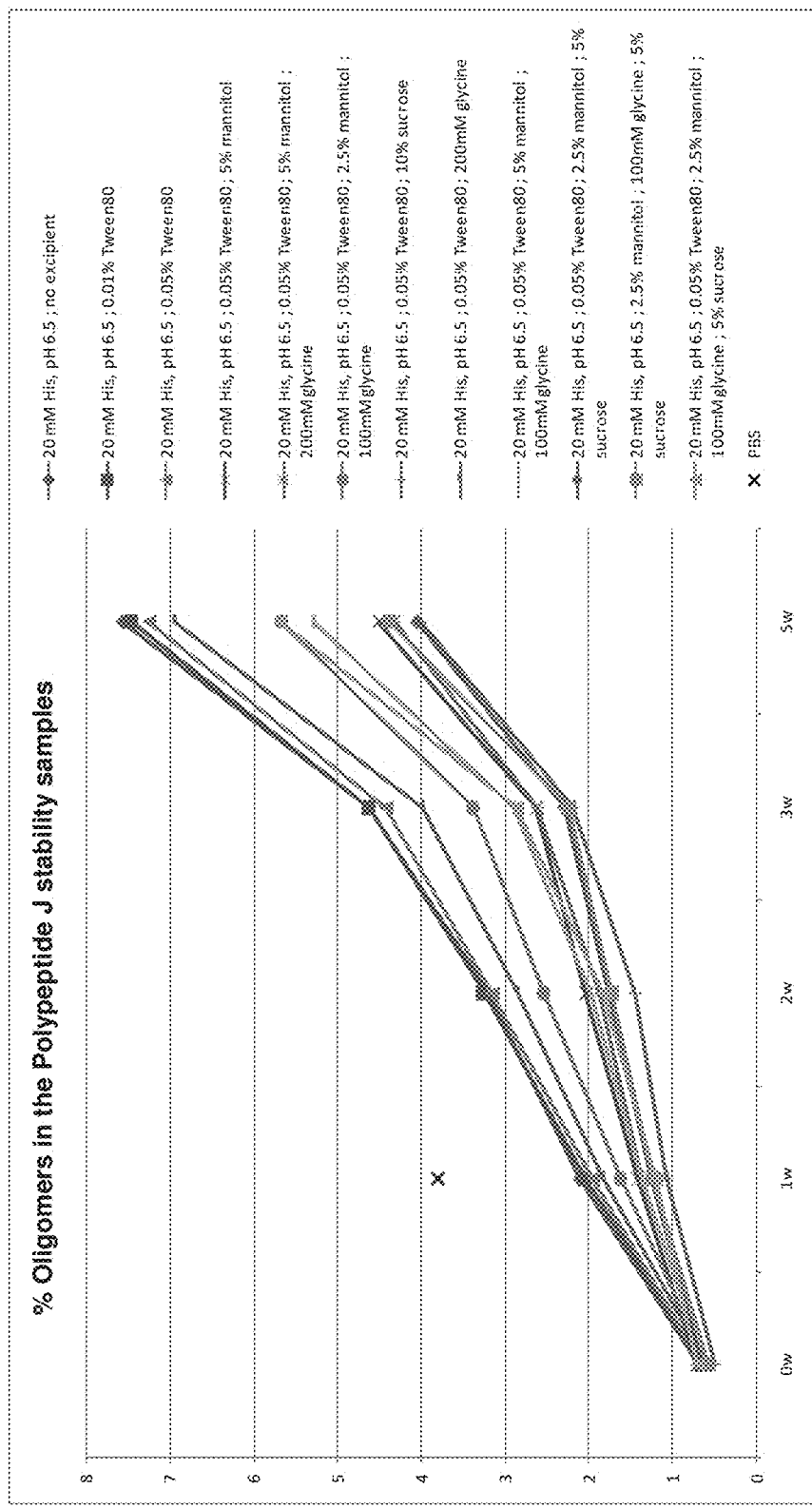
FIG. 33: Time-dependent and buffer-dependent increase in the % oligomers observed in the stability samples stored for up to 5 weeks at 37° C., at a concentration of 10 mg/mL in the buffers indicated in the graph.

The peak area of the prepeaks increased significantly over time (FIG. 32 and FIG. 33). Given the relative position of the prepeaks to the main peak, the prepeaks most likely represented dimeric or oligomeric forms (aggregates) of Polypeptide J. The peak surface area of the prepeak increased with storage time and was accompanied by a concomitant decrease in surface area of the main peak.

An important observation was that the propensity to form dimers/oligomers was buffer-dependent: the propensity to oligomerize was significantly lower in the mannitol- and sucrose-containing formulations. Glycine appeared not to have such a positive effect in preventing the oligomerization process. Tween 80 had no inhibitory effect on the formation of oligomers.

In the samples stored for 6 months at 37° C., the lowest % of oligomers was found in the formulation containing 10% sucrose, again corroborating the stabilizing effect of sucrose on Polypeptide J (Table 15).

Example 10

Storage Stability Study of Polypeptide J at −70° C., −20° C., 5° C. 25° C. and 37° C.

Polypeptide J was formulated at 1.0 mg/mL in the 10 different buffers shown in Table 16, stored at −70° C., −20° C., +5° C. and 37° C. for 8 weeks and for 1 week+25° C. Stability samples were analyzed using SE-HPLC. Selected samples were also analyzed using Biacore (HSA binding) and potency assays (HSA and IL-6R).

TABLE 15

Overview of the SE-HPLC integration results after storage for 6 months at 37° C.

| Buffer | % pre peak 1 | % pre peak 2 | % main peak | % post peak |
|---|---|---|---|---|
| Ref | 0.52 | 0.17 | 99.3 | 0 |
| Buffer 1 | ND | ND | ND | ND |
| Buffer 2 | 20.4 | 2.1 | 73.4 | 4.1 |
| Buffer 3 | ND | ND | ND | ND |

TABLE 15-continued

Overview of the SE-HPLC integration results after storage for 6 months at 37° C.

| Buffer | % pre peak 1 | % pre peak 2 | % main peak | % post peak |
|---|---|---|---|---|
| Buffer 4 | 18.1 | 1.7 | 76.0 | 4.2 |
| Buffer 5 | 22.2 | 2.0 | 71.4 | 4.4 |
| Buffer 6 | 21.4 | 1.7 | 72.7 | 4.2 |
| Buffer 7 | 15.1 | 0 | 80.5 | 4.4 |
| Buffer 8 | 21.1 | 2.4 | 72.0 | 4.5 |
| Buffer 9 | 16.7 | 2.7 | 76.3 | 4.3 |
| Buffer 10 | 15.8 | 1.9 | 77.9 | 4.4 |
| Buffer 11 | 17.5 | 2.0 | 76.4 | 4.2 |
| Buffer 12 | 16.8 | 3.3 | 75.7 | 4.2 |

TABLE 16

Overview of the different formulation buffers tested in the stability study.

| Nr. | Conc. | Buffer | Mannitol | Sucrose | Trehalose | Glycine | Tween-80 |
|---|---|---|---|---|---|---|---|
| 1 | 10 mg/mL | 15 mM L-histidine, pH 6.5 | 5% | | | | 0.01% |
| 2 | 10 mg/mL | 15 mM L-histidine, pH 6.5 | | 10% | | | 0.01% |
| 3 | 10 mg/mL | 15 mM L-histidine, pH 6.5 | | | 10% | | 0.01% |
| 4 | 10 mg/mL | 15 mM L-histidine, pH 6.5 | | 7.5% | | 0.35% | 0.01% |
| 5 | 10 mg/mL | 15 mM L-histidine, pH 6.5 | 2.5% | 5% | | | 0.01% |
| 6 | 10 mg/mL | 15 mM phosphate, pH 6.5 | 5% | | | | 0.01% |
| 7 | 10 mg/mL | 15 mM phosphate, pH 6.5 | | 10% | | | 0.01% |
| 8 | 10 mg/mL | 15 mM phosphate, pH 6.5 | | | 10% | | 0.01% |
| 9 | 10 mg/mL | 15 mM phosphate, pH 6.5 | | 7.5% | | 0.35% | 0.01% |
| 10 | 10 mg/mL | 15 mM phosphate, pH 6.5 | 2.5% | 5% | | | 0.01% |

10.1 Storage for 8 Weeks at −70° C., −20° C., 5° C. and 1 Week at 25° C.

Polypeptide J was shown to be stable after storage for 8 weeks at −70° C., −20° C., 5° C. and for 1 week at 25° C. in all 10 buffers tested. No significant differences were observed in potency, and SE-HPLC profiles between the reference material and the 10 different storage samples (data not shown).

10.2. Storage for 8 Weeks at 37° C.
SE-HPLC

Prolonged storage at 37° C. resulted in the time-dependent formation of a postpeak and prepeak. The postpeak has a retention time between 22 and 23 minutes and most likely corresponded to Polypeptide J degradation fragments. The surface area of this peak however remained low (approximately 2%), suggesting only minimal degradation after 8 weeks at 37° C. The other postpeaks visible in the chromatograms were background peaks arising from the buffer components.

Figure 34A:
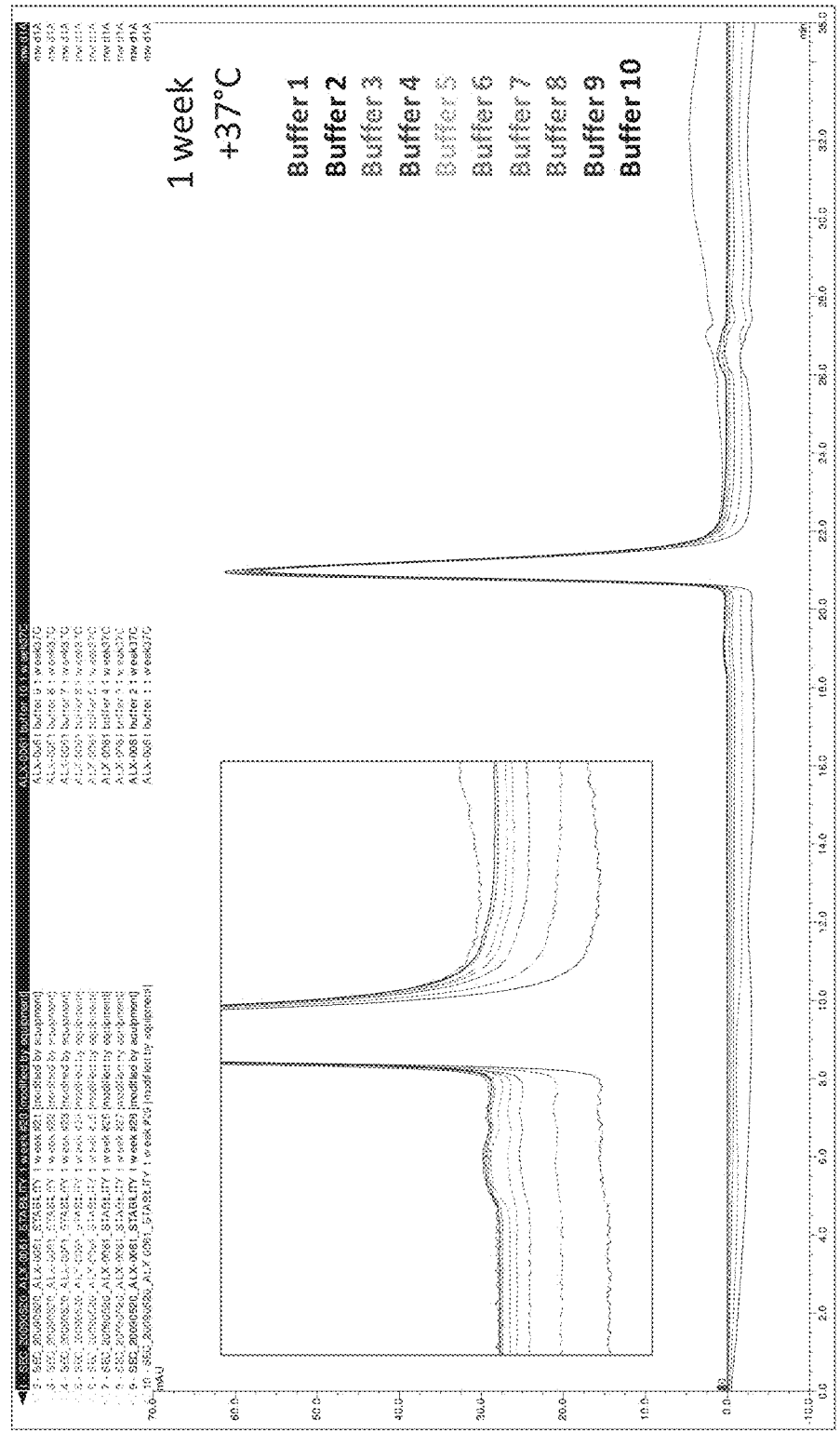
FIGS. 34A-34C: Overlay of the SE-HPLC chromatograms from Polypeptide J after storage for 1 week (FIG. 34A), 4 weeks (FIG. 34B, and 8 weeks (FIG. 34C) at +37° C. in 10 different formulation buffers. A zoom on the main peak (inset) demonstrates the time-dependent increase of the surface area of prepeaks and postpeak.
Figure 34B:
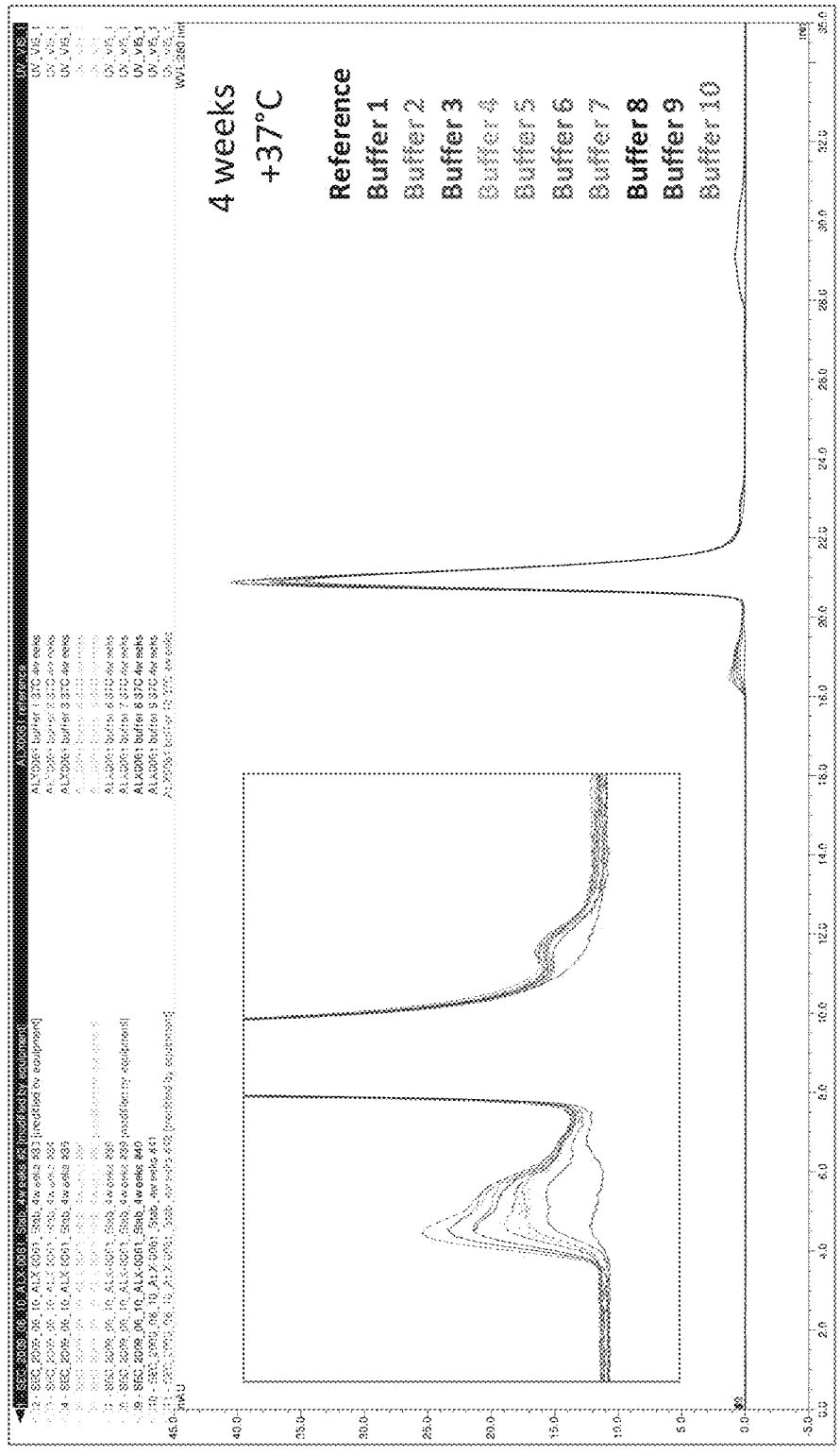
Figure 34C:
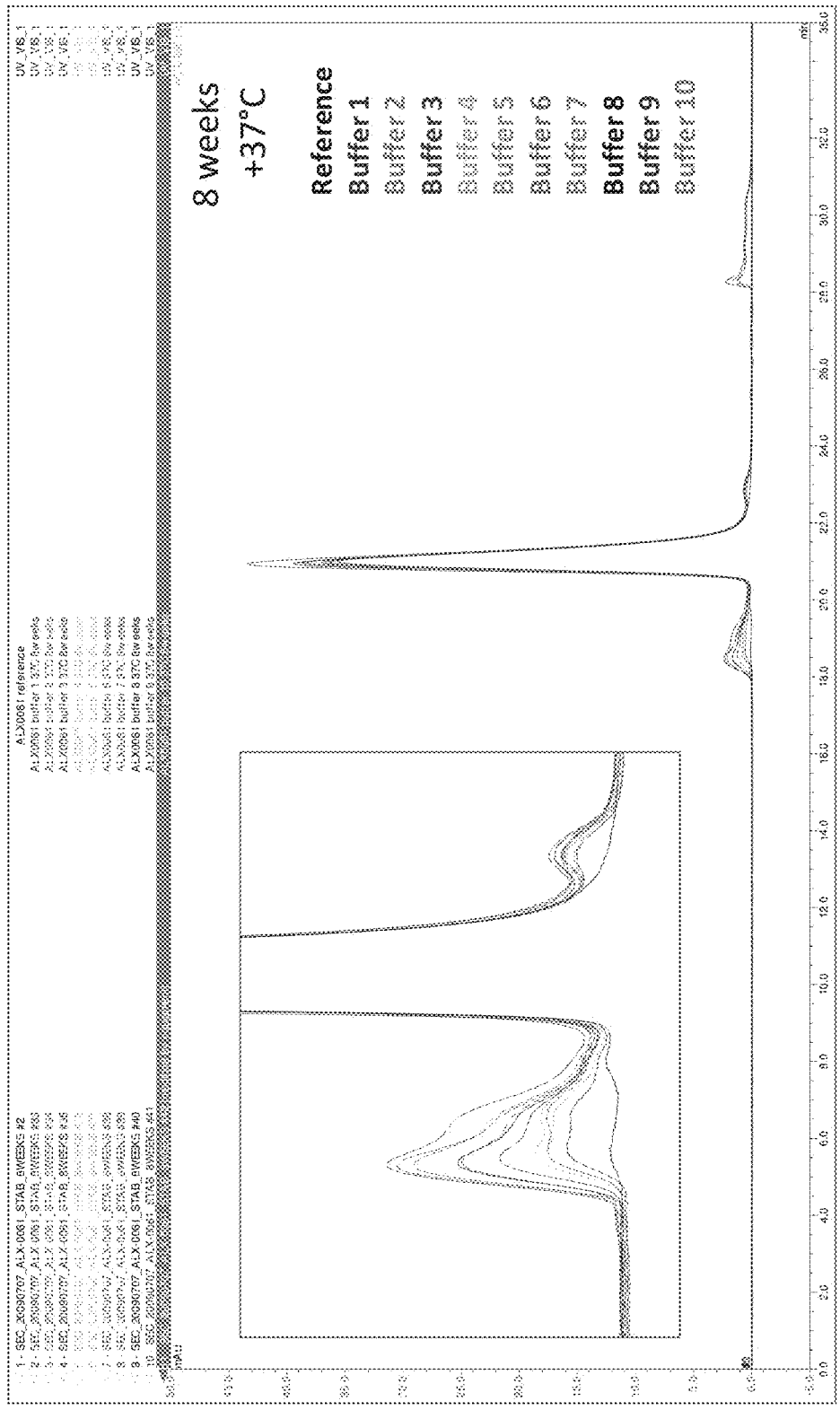

The SE-HPLC profile of Polypeptide J at time point 0 weeks included a main peak and two minor prepeaks, which were not completely baseline-resolved. The surface area of the prepeaks increased over time (FIGS. 34A-34C) and was accompanied by a concomitant decrease in surface area of the main peak. Given the relative position and heterogeneity of the prepeaks, they most likely represented dimeric and/or oligomeric forms of Polypeptide J. Because of this heterogeneity and the decreasing resolution between the prepeaks over time, the peaks were for simplicity integrated as a single peak.

Figure 35:
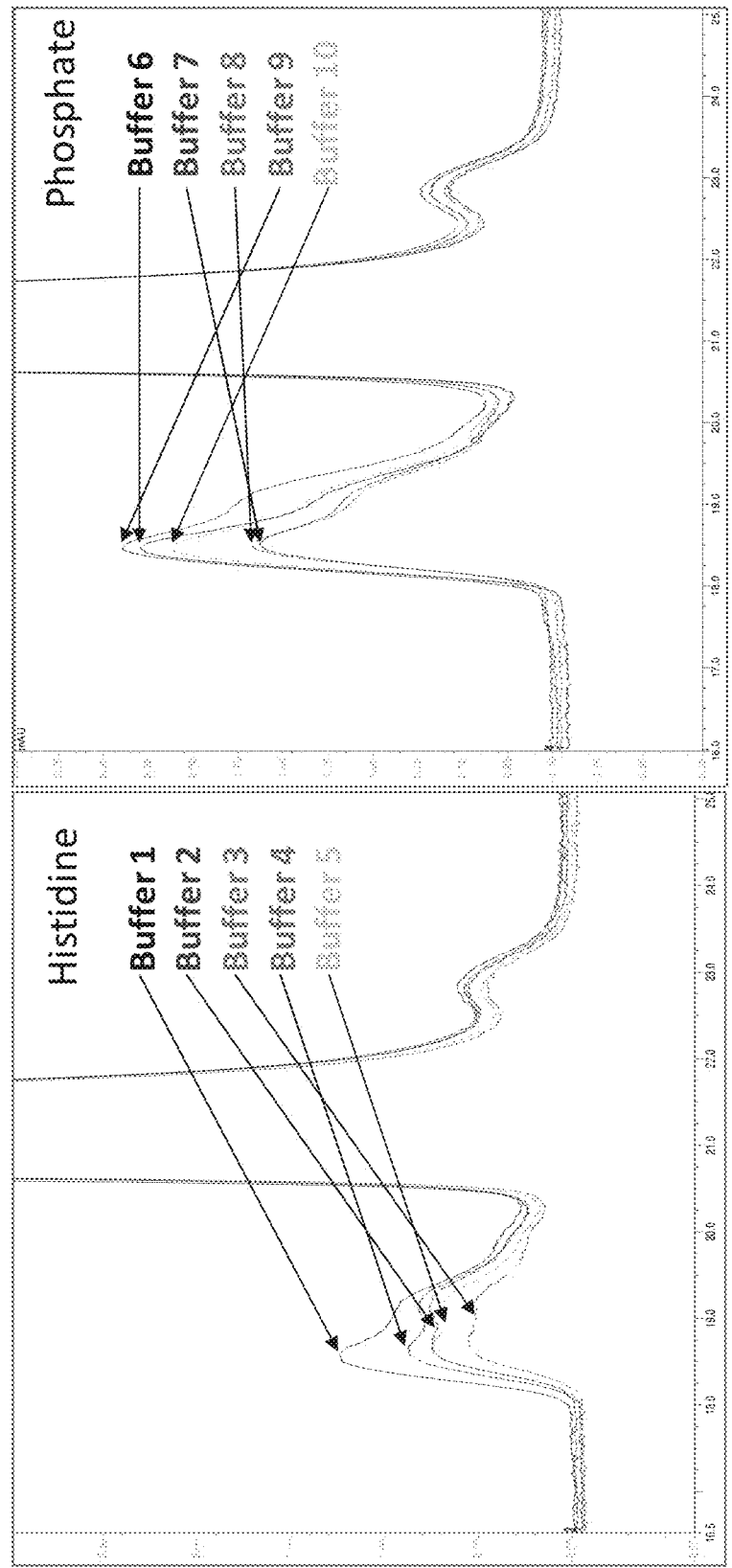
FIG. 35: SE-HPLC analysis of Polypeptide J samples stored for 8 weeks at 37° C. in L-histidine buffer (buffers 1-5) compared to phosphate buffer (buffers 6-10). The amount of oligomers was lowest in buffer 3.
Figure 36:
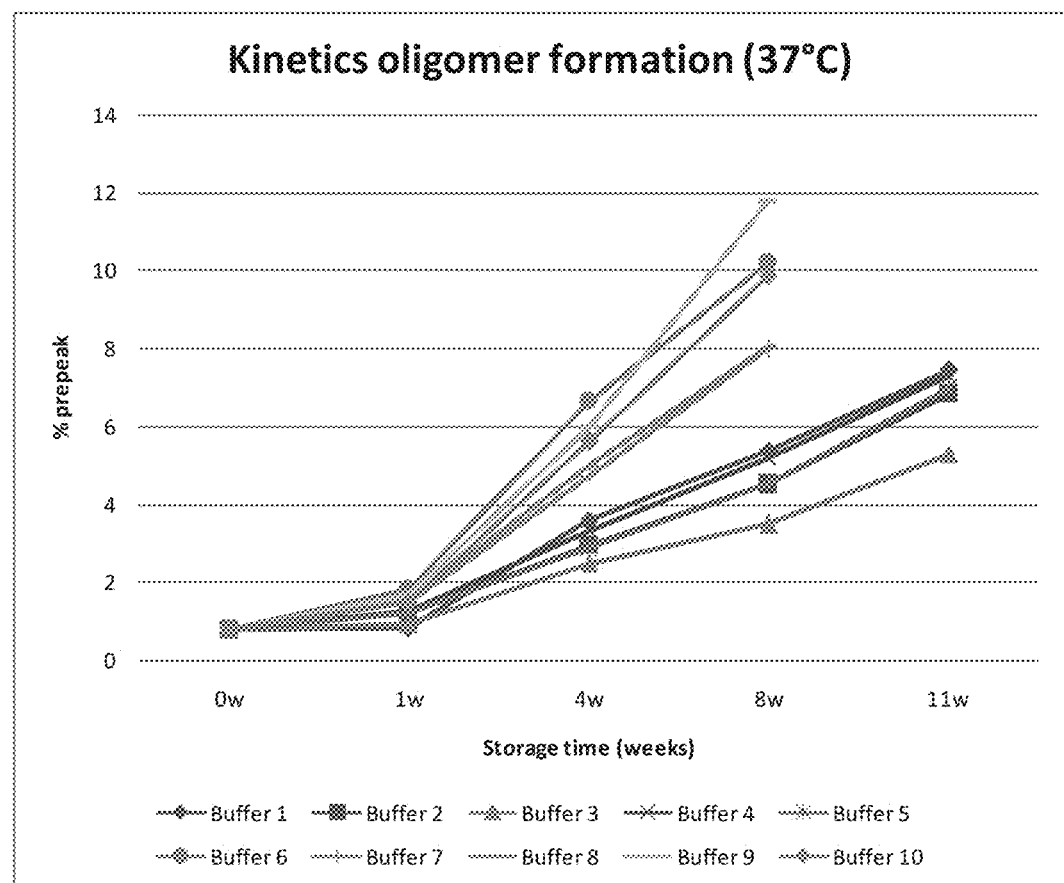
FIG. 36: Kinetics of oligomer formation upon storage of Polypeptide J in the different buffers.

An important observation was that the propensity to form dimers/oligomers was buffer-dependent: about 2-fold less oligomers were being formed in L-histidine buffer compared to phosphate buffer (FIG. 35, FIG. 36). The lowest amount of oligomers was observed in the trehalose-containing formulation, followed by the sucrose-containing formulation. The presence of a non-reducing sugar suppressed the extent of Polypeptide J oligomerization considerably.

Potency Assay and Biacore

The potency of the samples stored for 8 weeks at 37° C. in buffers 1-5 was determined relative to an unstressed reference batch using an HSA-binding ELISA and an inhibition ELISA for IL-6R (Table 17).

In the ELISA based potency assay for HSA binding, human serum albumin (HSA) was immobilized onto a multiwell Maxisorp ELISA plate by adsorption. After blocking excess binding sites on the plates with Superblock T20 (PBS) blocking buffer, a dilution series of test and reference samples was applied on the plate. Bound Polypeptide was subsequently detected using a bivalent anti-Nanobody Nanobody directly conjugated to horseradish peroxidase (HRP). In the presence of $H_2O_2$ HRP catalyzes a chemical reaction with Tetramethylbenzidine (es TMB) which results in the formation of a color. The reaction was stopped by adding 1N HCl. The optical density of the color was measured at 450 nm.

In the ELISA based potency assay for IL-6R binding, for the reference, control and test samples, different dilutions of the Polypeptides were prepared. These dilutions were pre-incubated with a constant amount of 100 ng/mL IL-6, followed by the addition of 4 ng/mL soluble IL-6R. Subsequently, this mixture was transferred to a microtiter plate coated with a non neutralizing anti-IL-6R Nanobody. After washing, residual bound IL-6 was detected with biotinylated anti-human IL-6 monoclonal antibody, followed by HRP-labeled streptavidin detection. In the presence of $H_2O_2$ HRP catalyzes a chemical reaction with Tetramethylbenzidine (es TMB) which results in the formation of a color. The reaction was stopped by adding 1N HCl. The optical density of the color was measured at 450 nm. The relative potency of the test samples compared to the reference sample was analyzed by use of PLA 2.0 Software.

The HSA binding functionality of the samples stored in buffers 1-10 was also analyzed using Biacore (Table 18). For the affinity measurement on Biacore, a chip was first immobilized with HSA (amine coupling using the Biacore amine coupling kit). After a preconditioning step of 5 injections of the Polypeptide 1, all samples were diluted to 2.5 nM in triplicate and analyzed on the chip. Quality control of the chips using the reference sample was included in the experiment to detect any loss of activity or decrease in response (deterioration of the chip). Slopes were determined using the general fit method and the linear fit model (BIAevaluation software). To determine the initial binding rate (IBR), the slope between 5 s and 30 s was selected. The values of these slopes were transferred in excel and the percentage activity compared to the reference was determined.

Samples formulated in the same buffers and stored at −70° C. were included as the reference molecules.

TABLE 17

Relative potency of Polypeptide J after 8 weeks at +37° C. compared to a reference sample.

| Buffer | HSA | IL-6R |
|---|---|---|
| 1 | 1.080 (0.954-1.223) | 1.153 (0.957-1.389) |
| 2 | 0.975 (0.887-1.072) | 0.980 (0.760-1.263) |
| 3 | 1.038 (0.952-1.132) | 1.117 (0.910-1.372) |
| 4 | 1.182 (1.074-1.300) | 1.061 (0.908-1.240) |
| 5 | 1.080 (1.004-1.161) | 1.082 (0.925-1.266) |

TABLE 18

Summary of the Biacore results for HSA binding of the stability samples stored for 8 weeks at 37° C., expressed as % activity compared to the equivalent sample stored at −70° C.

| Buffer | % activity compared to reference |
|---|---|
| 1 | 97.5 |
| 2 | 93.2 |

TABLE 18-continued

Summary of the Biacore results for HSA binding of the stability samples stored for 8 weeks at 37° C., expressed as % activity compared to the equivalent sample stored at −70° C.

| Buffer | % activity compared to reference |
|---|---|
| 3 | 92.5 |
| 4 | 83.9 |
| 5 | 101.9 |
| 6 | 92.2 |
| 7 | 89.4 |
| 8 | 99.0 |
| 9 | 84.3 |
| 10 | 89.6 |

Whereas the potency assays showed comparable HSA and IL-6R binding potencies between the stability samples and the reference material, Biacore analysis demonstrated some differences in HSA binding activities. A functionality loss of approximately 16% was observed in the buffers containing a combination of sucrose and glycine (buffer 4 and 9). Formulations containing either mannitol, sucrose or trehalose showed an activity between 90 and 100% after storage for 8 weeks at 37° C.

TABLE A

Sequence Listings

| Code | SEQ ID NO: | Sequence |
|---|---|---|
| Polypeptide A | 1 | EVQLVESGGGLVQPGGSLRLSCAASGRTFSYNPMGWFRQAPGKG RELVAAISRTGGSTYYPDSVEGRFTISRDNAKRMVYLQMNSLRAE DTAVYYCAAAGVRAEDGRVRTLPSEYTFWGQGTQVTVSSAAAE VQLVESGGGLVQPGGSLRLSCAASGRTFSYNPMGWFRQAPGKGR ELVAAISRTGGSTYYPDSVEGRFTISRDNAKRMVYLQMNSLRAED TAVYYCAAAGVRAEDGRVRTLPSEYTFWGQGTQVTVSS |
| Polypeptide B | 2 | EVQLVESGGGLVQPGNSLRLSCAASGFTFSSFGMSWVRQAPGKG LEWVSSISGSGSDTLYADSVKGRFTISRDNAKTTLYLQMNSLRPED TAVYYCTIGGSLSRSSQGTLVTVSS |
| Polypeptide C | 3 | EVQLVESGGGLVQPGGSLRLSCAASGFTFSDYDIGWFRQAPGKGR EGVSGISSSDGNTYYADSVKGRFTISRDNAKNTLYLQMNSLRPED TAVYYCAAEPPDSSWYLDGSPEFFKYWGQGTLVTVSSGGGGSGG GSEVQLVESGGGLVQPGNSLRLSCAASGFTFSSFGMSWVRQAPGK GLEWVSSISGSGSDTLYADSVKGRFTISRDNAKTTLYLQMNSLRPE DTAVYYCTIGGSLSRSSQGTLVTVSSGGGGSGGGSEVQLVESGGG LVQPGGSLRLSCAASGFTFSDYDIGWEFRQAPGKGREGVSGISSSDG NTYYADSVKGRFTISRDNAKNTLYLQMNSLRPEDTAVYYCAAEP PDSSWYLDGSPEFFKYWGQGTLVTVSS |
| Polypeptide D | 4 | EVQLVESGGGLVQPGGSLRLSCAASGFTFSDYDIGWFRQAPGKGR EGVSGISSSDGNTYYADSVKGRFTISRDNAKNTLYLQMNSLRPED TAVYYCAAEPPDSSWYLDGSPEFFKYWGQGTLVTVSSDAHKSEV AHRFKDLGEENFKALVLIAFAQYLQQCPFEDHVKLVNEVTEFAKT CVADESAENCDKSLHTLFGDKLCTVATLRETYGEMADCCAKQEP ERNECFLQHKDDNPNLPRLVRPEVDVMCTAFHDNEETFLKKYLY EIARRHPYFYAPELLFFAKRYKAAFTECCQAADKAACLLPKLDEL RDEGKASSAKQRLKCASLQKFGERAFKAWAVARLSQRFPKAEFA EVSKLVTDLTKVHTECCHGDLLECADDRADLAKYICENQDSISSK LKECCEKPLLEKSHCIAEVENDEMPADLPSLAADFVESKDVCKNY AEAKDVFLGMFLYEYARRHPDYSVVLLLRLAKTYETTLEKCCAA ADPHECYAKVFDEFKPLVEEPQNLIKQNCELFEQLGEYKFQNALL VRYTKKVPQVSTPTLVEVSRNLGKVGSKCCKHPEAKRMPCAEDY LSVVLNQLCVLHEKTPVSDRVTKCCTESLVNRRPCFSALEVDETY VPKEFNAETFTFHADICTLSEKERQIKKQTALVELVKHKPKATKEQ LKAVMDDFAAFVEKCCKADDKETCFAEEGKKLVAASQAALGL |
| Polypeptide E | 5 | EVQLVESGGGLVQPGGSLRLSCAASGFTFSDYDIGWFRQAPGKGR EGVSGISSSDGNTYYADSVKGRFTISRDNAKNTLYLQMNSLRPED TAVYYCAAEPPDSSWYLDGSPEFFKYWGQGTLVTVSSGGGGSGG GSEVQLVESGGOLVQPGNSLRLSCAASGFTFSSFGMSWVRQAPGK |

TABLE A-continued

Sequence Listings

| Code | SEQ ID NO: | Sequence |
|---|---|---|
| | | GLEWVSSISGSGSDTLYADSVKGRFTISRDNAKTTLYLQMNSLRPE<br>DTAVYYCTIGGSLSRSSQGTLVTVSS |
| Polypeptide F | 6 | AVQLVESGGGLVQPGNSLRLSCAASGFTFRSFGMSWVRQAPGKE<br>PEWVSSISGSGSDTLYADSVKGRFTISRDNAKTTLYLQMNSLKPED<br>TAVYYCTIGGSLSRSSQGTQVTVSS |
| Ligand A | 7 | DISEPPLHDFYCSRLLDLVFLLDGSSRLSEAEFEVLKAFVVDMMER<br>LRISQKWVRVAVVEYHDGSHAYIGLKDRKRPSELRRIASQVKYA<br>GSQVASTSEVLKYTLFQIFSKIDRPEASRIALLLMASQEPQRMSRNF<br>VRYVQGLKKKKVIVIPVGIGPHANLKQIRLIEKQAPENKAEVLSSV<br>DELEQQRDEIVSYLCDLAPEAPPPTHHHHHH |
| CDR3 and<br>FR4 of<br>polypeptide B | 8 | GGSLSRSSQGTLVTVSS |
| Polypeptide G | 9 | EVQLVESGGGLVQPGGSLRLSCAASGFTFRSFGMSWVRQAPGKEP<br>EWVSSISGSGSDTLYADSVKGRFTISRDNAKTTLYLQMNSLKPED<br>TAVYYCTIGGSLSRSSQGTQVTVSS |
| Polypeptide H | 10 | EVQLVESGGGLVQPGGSLRLSCAASGFTFRSFGMSWVRQAPGKG<br>LEWVSSISGSGSDTLYADSVKGRFTISRDNAKTTLYLMNSLKPE<br>DTAVYYCTIGGSLSRSSQGTQVTVSS |
| Polypeptide I | 11 | EVQLVESGGGLVQPGGSLRLSCAASGFTFSSYPMGWFRQAPGKG<br>REFVSSITGSGGSTYYADSVKGRFTISRDNAKNTLYLQMNSLRPED<br>TAVYYCAAYIRPDTYLSRDYRKYDYWGQGTLVTVSSGGGGSGG<br>GSEVQLVESGGGLVQPGNSLRLSCAASGFTFSSFGMSWVRQAPGK<br>GLEWVSSISGSGSDTLYADSVKGRFTISRDNAKTTLYLQMNSLRPE<br>DTAVYYCTIGGSLSRSSQGTLVTVSSGGGGSGGGSEVQLVESGGG<br>LVQPGGSLRLSCAASGFTFSSYPMGWFRQAPGKGREFVSSITGSG<br>GSTYYADSVKGRFTISRDNAKNTLYLQMNSLRPEDTAVYYCAAYI<br>RPDTYLSRDYRKYDYWGQGTLVTVSS |
| Polypeptide J | 12 | EVQLVESGGGLVQPGGSLRLSCAASGSVFKINVMAWYRQAPGKG<br>RELVAGIISGGSTSYADSVKGRFTISRDNAKNTLYLQMNSLRPEDT<br>AVYYCAFITTESDYDLGRRYWGQGTLVTVSSGGGGSGGGSEVQL<br>VESGGGLVQPGNSLRLSCAASGFTFSSFGMSWVRQAPGKGLEWV<br>SSISGSGSDTLYADSVKGRFTISRDNAKTTLYLQMNSLRPEDTAVY<br>YCTIGGSLSRSSQGTLVTVSS |
| Polypeptide K | 13 | EVQLVESGGGLVQPGGSLRLSCAASGSVFKINVMAWYRQAPGKG<br>RELVAGIIGGSTSYADSVKGRFTISRDNAKNTLYLQMNSLRPEDT<br>AVYYCAFITTESDYDLGRRYWGQGTLVTVSSGGGGSGGGSEVQL<br>VESGGGLVQPGGSLRLSCAASGSVFKINVMAWYRQAPGKGRELV<br>AGIISGGSTSYADSVKGRFTISRDNAKNTLYLQMNSLRPEDTAVY<br>YCAFITTESDYDLGRRYWGQGTLVTVSSGGGGSGGGSEVQLVES<br>GGGLVQPGNSLRLSCAASGFITSSFGMSWVRQAPGKGLEWVSSIS<br>GSGSDTLYADSVKGRFTISRDNAKTTLYLQMNSLRPEDTAVYYCT<br>IGGSLSRSSQGTLVTVSS |
| Polypeptide L | 14 | EVQLVESGGGLVQPGGSLRLSCAASGSVFKINVMAWYRQAPGKG<br>RELVAGIISGGSTSYADSVKGRFTISRDNAKNTLYLQMNSLRPEDT<br>AVYYCAFITTESDYDLGRRYWGQGTLVTVSSGGGGSGGGSEVQL<br>VESGGGLVQPGNSLRLSCAASGFTFSSFGMSWVRQAPGKGLEWV<br>SSISGSGSDTLYADSVKGRFTISRDNAKTTLYLQMNSLRPEDTAVY<br>YCTIGGSLSRSSQGTLVTVSSGGGGSGGGSEVQLVESGGGLVQPG<br>GSLRLSCAASGSVFKINVMAWYRQAPGKGRELVAGIISGGSTSYA<br>DSVKGRFTISRDNAKNTLYLQMNSLRPEDTAVYYCAFITTESDYD<br>LGRRYWGQGTLVTVSS |

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

All of the references described herein are incorporated by reference, in particular for the teaching that is referenced hereinabove.

The invention claimed is:

1. A liquid pharmaceutical formulation for parenteral administration comprising i) a polypeptide that comprises at least one immunoglobulin single variable domain that binds human serum albumin and consists of 4 framework regions (FR1 to FR4, respectively) and 3 complementary determining regions (CDR1-CDR3, respectively), wherein the CDR1 has the amino acid sequence SFGMS (amino acids 167-171 of SEQ ID NO: 3), the CDR2 has the amino acid sequence SISGSGSDTLYADSVKG (amino acids 186-202 of SEQ ID NO: 3), and the CDR3 has the amino acid sequence GGSLSR (amino acids 235-240 of SEQ ID NO: 3), and ii) sucrose or trehalose, wherein the addition of said sucrose or trehalose results in a reduction of the % of the polypeptides that forms dimers during storage of the liquid formulation at 37° C., the % dimers as measured by SE-HPLC, and wherein the polypeptide does not comprise an Fc fusion.

2. The pharmaceutical formulation according to claim 1, wherein the sucrose or trehalose is present at a concentration of 1% to 20%.

3. The pharmaceutical formulation according to claim 1, wherein the sucrose or trehalose is present at a concentration of 5% to 10%.

4. The pharmaceutical formulation according to claim 1, additionally comprising NaCl and/or amino acids.

5. A sealed container containing a formulation according to claim 1.

6. A pharmaceutical unit dosage form suitable for parenteral administration to a human, comprising a formulation according to claim 1 in a suitable container.

7. A kit comprising one or more of the sealed containers according to claim 5, and instructions for use of the formulation.

8. A kit comprising one or more of the pharmaceutical unit dosage forms according to claim 6, and instructions of use of the formulation.

9. The pharmaceutical formulation of claim 1, wherein the polypeptide is susceptible to dimerization.

* * * * *